(12) United States Patent
Cirillo et al.

(10) Patent No.: US 10,962,540 B2
(45) Date of Patent: Mar. 30, 2021

(54) BETA LACTAMASE AS BIOMARKER FOR THE SPECIFIC DETECTION OF TUBERCULOSIS-COMPLEX BACTERIA

(71) Applicant: The Texas A&M University System, College Station, TX (US)

(72) Inventors: Jeffrey D. Cirillo, College Station, TX (US); Michael T. Norman, Temple, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/218,193

(22) Filed: Dec. 12, 2018

(65) Prior Publication Data

US 2019/0101538 A1    Apr. 4, 2019

Related U.S. Application Data

(62) Division of application No. 15/504,633, filed as application No. PCT/US2015/045572 on Aug. 17, 2015, now Pat. No. 10,175,239.

(Continued)

(51) Int. Cl.
*G01N 33/573*    (2006.01)
*C07K 16/12*    (2006.01)
(Continued)

(52) U.S. Cl.
CPC ....... *G01N 33/573* (2013.01); *C07K 16/1289* (2013.01); *C07K 16/40* (2013.01); *C12N 9/86* (2013.01); *C12Q 1/04* (2013.01); *C12Q 1/689* (2013.01); *C12Y 305/02006* (2013.01); *G01N 33/5695* (2013.01); *G01N 33/6854* (2013.01); *C07K 2317/33* (2013.01);
(Continued)

(58) Field of Classification Search
CPC ........... A61K 49/0021; A61K 49/0028; A61K 49/0032; A61K 49/0041; A61K 49/0052; A61K 49/0013; G01N 21/6486; G01N 2333/986; C12Q 1/04; C12Q 1/34; C09B 57/02
USPC ....... 424/9.6; 435/18; 514/198, 254.11, 354; 536/55; 540/219
See application file for complete search history.

(56) References Cited

U.S. PATENT DOCUMENTS

| | | |
|---|---|---|
| 2005/0186197 A1 | 8/2005 | Palzkill et al. |
| 2013/0164221 A1 | 6/2013 | Cirillo et al. |
| 2014/0127712 A1 | 5/2014 | Cirillo et al. |

FOREIGN PATENT DOCUMENTS

| | | |
|---|---|---|
| EP | 0 300 923 A2 | 1/1989 |
| WO | 2011/119484 A1 | 9/2011 |

OTHER PUBLICATIONS

Wang et al., (Int. J. Environ Res Public Health. Jul. 2013; 10(7):2688-2698. Published online Jun. 28, 2013) (Year: 2013).*

(Continued)

*Primary Examiner* — Jana A Hines
(74) *Attorney, Agent, or Firm* — Christensen O'Connor Johnson Kindness PLLC

(57) ABSTRACT

The present disclosure provides methods, reagents, systems, and devices that target β lactamase as a biomarker for the sensitive and specific detection of tuberculosis-complex bacteria. Specifically, the present disclosure relates to methods and compositions for the detection of specific β-lactamase protein and nucleic acid sequences to indicate the presence of tuberculosis-complex bacteria.

16 Claims, 21 Drawing Sheets

Specification includes a Sequence Listing.

Related U.S. Application Data

(60) Provisional application No. 62/134,332, filed on Mar. 17, 2015, provisional application No. 62/038,736, filed on Aug. 18, 2014.

(51) Int. Cl.
    | | |
    |---|---|
    | *C12N 9/86* | (2006.01) |
    | *C12Q 1/04* | (2006.01) |
    | *G01N 33/569* | (2006.01) |
    | *C12Q 1/689* | (2018.01) |
    | *C07K 16/40* | (2006.01) |
    | *G01N 33/68* | (2006.01) |

(52) U.S. Cl.
    CPC ... *G01N 2333/35* (2013.01); *G01N 2333/986* (2013.01); *G01N 2469/10* (2013.01); *G01N 2800/52* (2013.01)

(56) References Cited

OTHER PUBLICATIONS

Hujer et al., (J of Clin Microbiol. Jun. 2002, vol. 40, No. 6;p. 1947-1957) i (Year: 2002).*
McDonough et al., (J. Bacteriol. Oct. 2008. 190(19):6428-6438) (Year: 2008).*
McDonough et al., (J. Bacteriol. 187:7667-7679). (Year: 2005).*
Of Xie et al., (Nat. Chem. Oct. 2012; 4(10):802-809) (Year: 2012).*
Flores, A.R., et al., "Genetic Analysis of the β-Lactamases of Mycobacterium tuberculosis and Mycobacterium Smegmatis and Susceptibility to β-Lactam Antibiotics," Microbiology 151(Pt. 2):521-532, Feb. 2005.
Fontán, P., et al., "Global Transcriptional Profile of Mycobacterium tuberculosis During THP-1 Human Macrophage Infection," Infection and Immunity 76(2):717-725, Feb. 2008.
Garnier, T., et al., "Mycobacterium bovis AF2122/97," Nucleic Acid Sequence Accession No. P0A517, submitted to UniProt Mar. 15, 2005, <http://www.ncbi.nlm.nih.gov/protein/6121996?sat=188 &satkey=3016131> [retrieved Oct. 21, 2015], 2 pages; reference location: "The Complete Genome Sequence of Mycobacterium bovis," Proceedings of the National Academy of Sciences of the USA (PNAS) 100(13):7877-7882, Jun. 2003.
International Search Report and Written Opinion dated Jan. 7, 2016, issued in corresponding International Application No. PCT/US15/45572, filed Aug. 17, 2015, 17 pages.
Invitation to Pay Additional Fees and, Where Applicable, Protest Fee, dated Oct. 28, 2015, issued in corresponding International Application No. PCT/US15/45572, filed Aug. 17, 2015, 4 pages.
Rodriguez, G.M., et al., "ideR, an Essential Gene in Mycobacterium tuberculosis: Role of IdeR in Iron-Dependent Gene Expression, Iron Metabolism, and Oxidative Stress Response," Infection and Immunity 70(70):3371-3381, Jul. 2002.
Talaat, A.M., et al., "The Temporal Expression Profile of Mycobacterium tuberculosis Infection in Mice," Proceedings of the National Academy of Sciences of the USA (PNAS) 101(13):4602-4607, Mar. 2004.
Voskuil, M.I., et al., "Mycobacterium tuberculosis Gene Expression During Adaptation to Stationary Phase and Low-Oxygen Dormancy," Tuberculosis 84(3-4):218-227, 2004.
Voskuil, M.I., et al., "The Response of Mycobacterium tuberculosis to Reactive Oxygen and Nitrogen Species," Frontiers in Microbiology 2(105):1-12, May 2011.
Wang, F., et al., "Crystal Structure and Activity Studies of the Mycobacterium tuberculosis β-Lactamase Reveal its Critical Role in Resistance to β-Lactam Antibiotics," Antimicrobial Agents and Chemotherapy 50(8):2762-2771, Aug. 2006.
Kurz, S.G., et al., "Can Inhibitor-Resistant Substitutions in the Mycobacterium tuberculosis β-Lactamase BlaC Lead to Clavulanate Resistance?: A Biochemical Rationale for the Use of β-Lactam—β-Lactamase Inhibitor Combinations," Antimicrobial Agents and Chemotherapy 57(12):6085-6096, Dec. 2013.
McDonough, J.A., et al., "Identification of Functional Tat Signal Sequences in Mycobacterium tuberculosis Proteins," Journal of Bacteriology 190(19):6428-6438, Oct. 2008.
Partial Supplementary European Search Report dated Dec. 19, 2017, issued in European Application No. 15834020.8, filed Aug. 17, 2015, 16 pages.
Wivagg, C.N., et al., "Mechanisms of β-Lactam Killing and Resistance in the Context of Mycobacterium tuberculosis," Journal of Antibiotics 67(9):645-654, Sep. 2014.
Xie, H., et al., "Rapid Point-of-Care Detection of the tuberculosis Pathogen Using a BlaC-Specific Fluorogenic Probe," Nature Chemistry 4(10):802-809, Oct. 2012.
Communication dated Jun. 19, 2019, issued in European Application No. 15834020.8, filed Aug. 17, 2015, 6 pages.
International Preliminary Report on Patentability dated Feb. 21, 2017, issued in corresponding International Application No. PCT/US15/45572, filed Aug. 17, 2015, 10 pages.
Extended European Search Report dated Apr. 3, 2018, issued in European Application No. 15834020.8, filed Aug. 17, 2015, 12 pages.

* cited by examiner

| | | |
|---|---|---|
| M.tuberculosis/1-307 | 1 | MRNRGFGRRELLVAMAMLVSVTGCARHASGARPASTTLPAGADLADRFAELERRYDARLGVYYPATGTT 69 |
| M.bovis/1-307 | 1 | MRNRGFGRRELLVAMAMLVSVTGCARHASGARPASTTLPAGADLADRFAELERRYDARLGVYYPATGTT 69 |
| M.canettii/1-307 | 1 | MRNRGFGRRELLVAMAMLVSVTGCARHASGARPASTTLPAGADLADRFAELERRYDARLGVYYPATGTT 69 |
| M.bovis(BCG)/1-307 | 1 | MRNRGFGRRELLVAMAMLVSVTGCARHASGARPASTTLPAGADLADRFAELERRYDARLGVYYPATGTT 69 |
| M.africanum/1-307 | 1 | MRNRGFGRRELLVAMAMLVSVTGCARHASGARPASTTLPAGADLADRFAELERRYDARLGVYYPATGTT 69 |

Motif I

| | | |
|---|---|---|
| M.tuberculosis/1-307 | 70 | AAIEYRADERFAFCSTFKAPLVAAVLHQNPLTHLDKLITYTSDDIRSISPVAQQHVQTGMTIGQLCDAA 138 |
| M.bovis/1-307 | 70 | AAIEYRADERFAFCSTFKAPLVAAVLHQNPLTHLDKLITYTSDDIRSISPVAQQHVQTGMTIGQLCDAA 138 |
| M.canettii/1-307 | 70 | AAIEYRADERFAFCSTFKAPLVAAVLHQNPLTHLDKLITYTSDDIRSISPVAQQHVQTGMTIGQLCDAA 138 |
| M.bovis(BCG)/1-307 | 70 | AAIEYRADERFAFCSTFKAPLVAAVLHQNPLTHLDKLITYTSDDIRSISPVAQQHVQTGMTIGQLCDAA 138 |
| M.africanum/1-307 | 70 | AAIEYRADERFAFCSTFKAPLVAAVLHQNPLTHLDKLITYTSDDIRSISPVAQQHVQTGMTIGQLCDAA 138 |

Motif II

| | | |
|---|---|---|
| M.tuberculosis/1-307 | 139 | IRYSDGTAANLLLADLGGPGGGTAAFTGYLRSLGDTVSRLDAEEPELNRDPPGDERDTTTPHAIALVLQ 207 |
| M.bovis/1-307 | 139 | IRYSDGTAANLLLADLGGPGGGTAAFTGYLRSLGDTVSRLDAEEPELNRDPPGDERDTTTPHAIALVLQ 207 |
| M.canettii/1-307 | 139 | IRYSDGTAANLLLADLGGPGGGTAAFTGYLRSLGDTVSRLDAEEPELNRDPPGDERDTTTPHAIALVLQ 207 |
| M.bovis(BCG)/1-307 | 139 | IRYSDGTAANLLLADLGGPGGGTAAFTGYLRSLGDTVSRLDAEEPELNRDPPGDERDTTTPHAIALVLQ 207 |
| M.africanum/1-307 | 139 | IRYSDGTAANLLLADLGGPGGGTAAFTGYLRSLGDTVSRLDAEEPELNRDPPGDERDTTTPHAIALVLQ 207 |

Motif III

| | | |
|---|---|---|
| M.tuberculosis/1-307 | 208 | QLVLGNALPPDKRALLTDWMARNTTGAKRIRAGFPADMKVIDKTGTGDYGRANDIAVWWSPTGVPYVVA 276 |
| M.bovis/1-307 | 208 | QLVLGNALPPDKRALLTDWMARNTTGAKRIRAGFPADMKVIDKTGTGDYGRANDIAVWWSPTGVPYVVA 276 |
| M.canettii/1-307 | 208 | QLVLGNALPPDKRALLTDWMARNTTGAKRIRAGFPADMKVIDKTGTGDYGRANDIAVWWSPTGVPYVVA 276 |
| M.bovis(BCG)/1-307 | 208 | QLVLGNALPPDKRALLTDWMARNTTGAKRIRAGFPADMKVIDKTGTGDYGRANDIAVWWSPTGVPYVVA 276 |
| M.africanum/1-307 | 208 | QLVLGNALPPDKRALLTDWMARNTTGAKRIRAGFPADMKVIDKTGTGDYGRANDIAVWWSPTGVPYVVA 276 |

| | | |
|---|---|---|
| M.tuberculosis/1-307 | 277 | VMSDRAGGGYDAEPREALLAEAATCVAGVLA 307 |
| M.bovis/1-307 | 277 | VMSDRAGGGYDAEPREALLAEAATCVAGVLA 307 |
| M.canettii/1-307 | 277 | VMSDRAGGGYDAEPREALLAEAATCVAGVLA 307 |
| M.bovis(BCG)/1-307 | 277 | VMSDRAGGGYDAEPREALLAEAATCVAGVLA 307 |
| M.africanum/1-307 | 277 | VMSDRAGGGYDAEPREALLAEAATCVAGVLA 307 |

```
M.tuberculosis/1-307   208 -------------------------------------QLVLG------NALPPDKRALL----TDMMARN 230
M.smegmatis/1-401      232 RHDVMGPPHVRPPSFCNAGGGLWSTADDYLRFVRLLLGDGTIDGVRVLSPESVRLMRTDRLSDEHKRH 299
M.marinum/1-311        208 -------------------------------------QVVLG------DALLPEKRDKL----IDWLQRS 230
E.coli/1-286           190 -------------------------------------KLLTG------ELLTLASRQQL----IDWMEAD 212
P.aeruginosa/1-262     172 ------------------------LAQGELPFFAP------VQSTVRAMTLLESGPGWELH-------GKTG 206
S.aureus/1-303         182 DLVWSDGPLGKTTYGDVFHQNEVEQSTY----NFEYADVDFLFTCFEQYEKEAQQLLA---LENPLPL 242
S.pneumoniae/1-422     247 DTTVKYVSAVNDFPGSYKPEGSGSLPKK-EDNKEYSLKDLITKVSKESDNVAHNLLGYYI---SNQSD 310
                                                                          Motif III
M.tuberculosis/1-307   231 TTGAKRIRAGFPADMKVIDKTGTODY--------GRANDIAVVWSPTGVPYVVAVMS----- 279
M.smegmatis/1-401      300 NFLGAPFWVGRGFGLNLSVVTDPAQSTPLFGPGGLGTFSMPGAYGTWWQADPGA--DLILLYLIQHCP 365
M.marinum/1-311        231 TTGAKRIRAGFPADMRVIDKTGSOEY--------GRANDVAVVWSPGGTPYVVAIMT----- 279
E.coli/1-286           213 KVAQPLLRSALPAGWFIADKSGAGER--------GSRGIIAALGPDGKPSRIVVIYT----- 261
P.aeruginosa/1-262     207 WCFDCTPELGWMVGWVKRNERLYGFALNIDMPG--------GEADIGKRVELQKASLKALGILP---- 262
S.aureus/1-303         243 PAYERILKAAHSFNLLDARKAISVTERQRYILRI---RTLTKAVAEAYYASREALGFPMC-NK 301
S.pneumoniae/1-422     311 ATFKSKMSAIMGDDWDPKEKLISSKMAGKFME---AIYNQNGFVLESLTKTDFDSQRIAKGVSVK-VA 374

M.tuberculosis/1-307   280 DRAGGGYDAEPREALLAEAATCVAGVLA------------------- 307 SEQ ID NO: 2
M.smegmatis/1-401      366 DLSVNAAAAVAGNPGLAKLRTAGPRFVRRTYRALGL----------- 401 SEQ ID NO: 31
M.marinum/1-311        280 DRVGGGPEAPWCDPLVADAAKCVADVLAQWSA--------------- 311 SEQ ID NO: 33
E.coli/1-286           282 --TGSQATMDERNRQIAEIGASLIKHW-------------------- 286 SEQ ID NO: 35
P.aeruginosa/1-262                                                                  SEQ ID NO: 37
S.aureus/1-303         302 DK-------------------------------------------- 303 SEQ ID NO: 39
S.pneumoniae/1-422     375 HKIGDADEFKHDTGVVYADSPFILSIFTKNSDYDTISKIAKDVYEVLK 422 SEQ ID NO: 40
```

```
M.tuberculosis/1-924   1 ------------------------------------------ATGCCAAC------------------------------    8
M.marinum/1-1206       1 ATGTCAGCCCGTTCGGCACCCTCCTAACGCCACGGCCGGAAAAACCGCTCCACGCCCCACCCGT   67
M.smegmatis/1-1521     1 ------------------------------------------AT----------------------------------    2
E.coli/1-861           1 ------------------------------------------------------------------------------
P.aeruginosa/1-789      
S.aureus/1-846

M.tuberculosis/1-924   10 --------------------AGAGGATTCGTCGTCGCGAAC--TGCTGGTAG---------    40
M.marinum/1-1206       1 ------------------------------------------GTGAATCTGACGCCAA   17
M.smegmatis/1-1521    68 CACCGCACGGCCGCCTACCGTCGACCGTCGAGGCTCGCGGTCTCGGCGTCTGCGCCAT  134
E.coli/1-861           1 --------------------GAGTATTCAACATTTCGTGTCGCCCTTATTC-------   34
P.aeruginosa/1-789      
S.aureus/1-846         1 ------------------------------------------TTGAAAAA----GTTAA------   13

M.tuberculosis/1-924   41 -----CGATGGCAATGCTGGTTCCGTGACGGGGTGTGCACGGCAT                     81
M.marinum/1-1206      18 CCAGGCTGATATCCGCCAGGGTCTGGCATC                                  46
M.smegmatis/1-1521   135 CGGTCCTGTTTCGCGCGGTGGCGCGGCCGACATCCTGCAGGCCGGCCCGCCTGAACCG    201
E.coli/1-861          35 ----CCTTTTTGCGCGCATTTTGCCTTCTCCTGTTTTTGCTCACCCA                  75
P.aeruginosa/1-789     1 ------------------------------ATGCCCCTCTCCTCTTCAGT-----        21
S.aureus/1-846        14 TATTTTTAATTGCAATTGCTTTAGTTTTAAGTGCATGTAAT                      54

M.tuberculosis/1-924 
M.marinum/1-1206     
M.smegmatis/1-1521  202 GCCCCGGCGACCGGCATTGCCGCCGCGCCCCCGGACCGCAGGTGACCCACC   268
E.coli/1-861         76 ----------------GCCCTTCTCCTGCTTCCGGG-C------ATACCCAGGGC    53
P.aeruginosa/1-789   22                                                               
S.aureus/1-846

M.tuberculosis/1-924  82 ----------------GCCAGCGGGGCCCGTCCGGCATCGACAACC---TTG   114
M.marinum/1-1206      47 ---------CCCG----ATTGCTCTCCGGCCGCCAGTGACCGTTTG          80
M.smegmatis/1-1521  269 CCGTGACCCGACGGGTGACTTCTCGGCCGTCACCCGGTCGACGACCCTCCGCACCCCC  335
E.coli/1-861          78 ----------------GAAACG---CTG                              84
P.aeruginosa/1-789    54 CAGCGAA---------TGGAACGACAGCCAGGCCGTGACAAGCTATTCGGCGCGGCGGG  104
S.aureus/1-846        55 ----------------TCAAACAGTCCACATGCCAAAGAGTTAAA----        83
```

```
M.tuberculosis/1-924    581 ------------------------------------------------GGATACCACAACACCGCACGCC----------CCCGCCGCACGTCGCGGC  603
M.marinum/1-1206        664 ATGTACCGCCCTCGACGCTGGACCAGCTACGGCACGACGTCATGG----GAGATACGCGCAACGCACTGGTTTCCGATCCGACGGACCGC  727
M.smegmatis/1-1521      907 GCGTGCGGACCGCAC-----------------------------------GTGACACCACGATGCCTGCAGCA------------------  964
E.coli/1-861            527 ----------------------------------------------------------------------------------C-------  549
P.aeruginosa/1-789      637 ---------------------------------------------------------------------------------------C--  638
S.aureus/1-846          508 ------------------------------------------------AAGATACTTCAACACCTGCTGCT-------------------  528

M.tuberculosis/1-924    604 ---------------------------ATCGC--CCTGGTGTTGCAGCAGCTTGTTCTCGGCAACGCGTT  644
M.marinum/1-1206        728 CTCCGTCG-----------------TTCTCAACGCCGCCG-GCGGATTCGTGGTC------------------  764
M.smegmatis/1-1521      965 GGACGAGCAACCGACTGCCGGCGGATTCCTGGAGCACGGCCTGCTGACCCGGTCGCTGAACCCGGTGCCCACCGGCTGCACCGGAACCGCT  1031
E.coli/1-861            550 ---ATGGC---AACAAGTTGCCAAACTATTAACTGGCGAACTACT  590
P.aeruginosa/1-789      639 GGAACTCG------G-------CTGGTCGGTGGCTGGCTGGGTGAACCG  671
S.aureus/1-846          529 ------------TTCGG---TAAGACTTTAAATAAACTTATCGCAAATGGAAAATT  569

M.tuberculosis/1-924    645 -----------------GCCGCCCGACAAGCGGGCACTGCTCACCGATTGGATGCGCCCAACACCACCGG  698
M.marinum/1-1206        765 -------AACCGCCGACGACTACCTGAGATTTGTCGGCGGCGAC------GGG  813
M.smegmatis/1-1521      1032 CGACGAGGACACCCGGCATCAGCTTCCCGGCAACAATTAATAGACTGGATGGAGGCGGATAAAGTTGC  1098
E.coli/1-861            591 ----------TACTCTAGCTTCGCCCTCGAACATCGAC------------------------------  644
P.aeruginosa/1-789      672 CAACGAGCCGCTCTACGGCTTCGCCCCCTGAACATCGAC------------------------------  708
S.aureus/1-846          570 -----AAGCAAAGAAAACAAAATTCTTACTTGATTTAATGTTAAATAATAAAAAGCGG  623

M.tuberculosis/1-924    699 A-GCCAAGC-----------------------GGCTCTCACCGGGAGTCGGTCGCGGCTGATGCGCACCGGCTGACCGGCTCA  706
M.marinum/1-1206        814 ACGATCGACGGCGCCTTCGG---GTGCTCTCACCGGGAGTCGGTCGCGGCTGATGCGCACCGGCTGACCGGCTCA  877
M.smegmatis/1-1521      1099 ACGGCCACGCACCCGGCATGGGCGGGTGGGTGCCGGAAGCGCGGGCGTGTTCACCGACGGTTCACCGACCTGGGCC  1165
E.coli/1-861            645 A-GGACCAC-----------------------------------------------------------------  652
P.aeruginosa/1-789      709 ---------------------------------------------------------------------------  
S.aureus/1-846          624 A-GATACTT-----------------------------------------------------------------  631

M.tuberculosis/1-924    707 --------GGATCCGAGCGGGCTTTCCCGCCGATTGGAAGGTGATCGACAAG  750
M.marinum/1-1206        878 GCGACGAGCGACAAGCGACACAACTTTCTCGGGGTGGGCGCGGGTTCGGGCTGAA  944
M.smegmatis/1-1521      1166 TGTTCCGCGAG----------GCGTTGCTCGACGACGGCCAACCGCCAGCACTTTCCGCTGCA  1223
E.coli/1-861            853 ---------------------TTCGCGCTCGGCGCCTTCGGGCTGGTTATTGCTGATAAA  896
P.aeruginosa/1-789      
S.aureus/1-846          832 ------------TAATTAAAGACGGTGTTCCAAAAGACTATAAGGTTGCTGATAAA  875
```

Gold Conjugated
Detection Reagent:
RabMab 22-12
6μg/ml
pH 8.4

Capture Reagent:
Goat anti-BlaC
PAC 8577
0.5mg/ml

CL   S   F   VF
TL   0   7   S

Gold Conjugated
Detection Reagent:
RabMab 27-11
6μg/ml
pH 8.4

Capture Reagent:
RabMab 20-8
1mg/ml

CL   7   7   7
TL   0   7   S

SEQUENCE LISTING

```
<160> NUMBER OF SEQ ID NOS: 40

<210> SEQ ID NO 1
<211> LENGTH: 924
<212> TYPE: DNA
<213> ORGANISM: Mycobacterium tuberculosis

<400> SEQUENCE: 1
atgcgcaaca gaggattcgg tcgtcgcgaa ctgctggtag cgatggcaat gctggtttcc      60
gtgacggggt gtgcacggca tgcgagcggg gcccgtccgg catcgacaac cttgccggcc     120
ggagcggatc tggcggatcg cttcgccgag ctggagcgca gatacgatgc ccggcttggg     180
gtgtatgtgc ccgccaccgg caccaccgcc gcgatcgaat accgcgccga tgagcggttc     240
gcattctgct ccacgttcaa ggcgccgctc gtggcggcgg tgctgcacca aaacccgctc     300
acgcatctgg acaaactgat cacctacacc agtgacgaca ttcggtcgat ctccccggtg     360
gcccaacaac acgttcagac cgggatgacg atcgggcagc tttgcgatgc ggcgatacgc     420
tatagcgacg gcaccgccgc caacctgttg ctggccgatc ttggcggtcc cgggggcggc     480
accgcggcat ttaccggcta cctccgcagc ttgggtgaca ccgtgagccg gttggacgcc     540
gaggaaccgg agttgaaccg cgatccgccc ggggacgaac gggataccac aacaccgcac     600
gccatcgccc tggtgttgca gcagcttgtt ctcggcaacg cgttgccgcc cgacaagcgg     660
gcactgctca ccgattggat ggcgcgcaac accaccggag ccaagcggat ccgagcgggc     720
tttcccgccg attggaaggt gatcgacaag accgggaccg gtgactacgg acgagcaaac     780
gacatcgcgg tcgtgtggtc accgaccggc gtgccctacg tggtggccgt catgtccgat     840
cgtgccggcg gcgggtatga cgccgagccc cgtgaggcgc tgctcgccga ggcggcgacg     900
tgcgttgccg gtgtgcttgc atag                                           924

<210> SEQ ID NO 2
<211> LENGTH: 307
<212> TYPE: PRT
<213> ORGANISM: Mycobacterium tuberculosis

<400> SEQUENCE: 2

Met Arg Asn Arg Gly Phe Gly Arg Arg Glu Leu Leu Val Ala Met Ala
1               5                   10                  15

Met Leu Val Ser Val Thr Gly Cys Ala Arg His Ala Ser Gly Ala Arg
            20                  25                  30

Pro Ala Ser Thr Thr Leu Pro Ala Gly Ala Asp Leu Ala Asp Arg Phe
        35                  40                  45

Ala Glu Leu Glu Arg Arg Tyr Asp Ala Arg Leu Gly Val Tyr Val Pro
    50                  55                  60

Ala Thr Gly Thr Thr Ala Ala Ile Glu Tyr Arg Ala Asp Glu Arg Phe
65                  70                  75                  80

Ala Phe Cys Ser Thr Phe Lys Ala Pro Leu Val Ala Ala Val Leu His
```

```
                       85                  90                  95
Gln Asn Pro Leu Thr His Leu Asp Lys Leu Ile Thr Tyr Thr Ser Asp
            100                 105                 110

Asp Ile Arg Ser Ile Ser Pro Val Ala Gln Gln His Val Gln Thr Gly
        115                 120                 125

Met Thr Ile Gly Gln Leu Cys Asp Ala Ala Ile Arg Tyr Ser Asp Gly
    130                 135                 140

Thr Ala Ala Asn Leu Leu Leu Ala Asp Leu Gly Gly Pro Gly Gly Gly
145                 150                 155                 160

Thr Ala Ala Phe Thr Gly Tyr Leu Arg Ser Leu Gly Asp Thr Val Ser
                165                 170                 175

Arg Leu Asp Ala Glu Glu Pro Glu Leu Asn Arg Asp Pro Pro Gly Asp
            180                 185                 190

Glu Arg Asp Thr Thr Thr Pro His Ala Ile Ala Leu Val Leu Gln Gln
        195                 200                 205

Leu Val Leu Gly Asn Ala Leu Pro Pro Asp Lys Arg Ala Leu Leu Thr
    210                 215                 220

Asp Trp Met Ala Arg Asn Thr Thr Gly Ala Lys Arg Ile Arg Ala Gly
225                 230                 235                 240

Phe Pro Ala Asp Trp Lys Val Ile Asp Lys Thr Gly Thr Gly Asp Tyr
                245                 250                 255

Gly Arg Ala Asn Asp Ile Ala Val Val Trp Ser Pro Thr Gly Val Pro
            260                 265                 270

Tyr Val Val Ala Val Met Ser Asp Arg Ala Gly Gly Gly Tyr Asp Ala
        275                 280                 285

Glu Pro Arg Glu Ala Leu Leu Ala Glu Ala Thr Cys Val Ala Gly
    290                 295                 300

Val Leu Ala
305

<210> SEQ ID NO 3
<211> LENGTH: 28
<212> TYPE: DNA
<213> ORGANISM: Artificial Sequence
<220> FEATURE:
<223> OTHER INFORMATION: Synthetic oligonucleotide probe

<400> SEQUENCE: 3
ttgccgagaa caagctgctg caacacca                                          28

<210> SEQ ID NO 4
<211> LENGTH: 29
<212> TYPE: DNA
<213> ORGANISM: Artificial Sequence
<220> FEATURE:
<223> OTHER INFORMATION: Synthetic oligonucleotide probe

<400> SEQUENCE: 4
tttgtccaga tgcgtgagcg ggttttggt                                         29

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide probe

<400> SEQUENCE: 5
ttgccgagaa caagctgctg caacacca                                          28
```

<210> SEQ ID NO 6
<211> LENGTH: 31
<212> TYPE: DNA
<213> ORGANISM: Artificial Sequence
<220> FEATURE:
<223> OTHER INFORMATION: Synthetic oligonucleotide probe

<400> SEQUENCE: 6
atcagtttgt ccagatgcgt gagcgggttt t                               31

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide probe

<400> SEQUENCE: 7
cgcgatccca gtgacgacat tcggtgatcg cg                              32

<210> SEQ ID NO 8
<211> LENGTH: 32
<212> TYPE: DNA
<213> ORGANISM: Artificial Sequence
<220> FEATURE:
<223> OTHER INFORMATION: Synthetic oligonucleotide probe

<400> SEQUENCE: 8
cgcgatcgct cacgcatctg gacaagatcg cg                              32

<210> SEQ ID NO 9
<211> LENGTH: 33
<212> TYPE: DNA
<213> ORGANISM: Artificial Sequence
<220> FEATURE:
<223> OTHER INFORMATION: Synthetic oligonucleotide probe

<400> SEQUENCE: 9
cgcgatcctc acgcatctgg acaaacgatc gcg                             33

<210> SEQ ID NO 10
<211> LENGTH: 32
<212> TYPE: DNA
<213> ORGANISM: Artificial Sequence
<220> FEATURE:
<223> OTHER INFORMATION: Synthetic oligonucleotide probe

<400> SEQUENCE: 10
cgcgatccaa aacccgctca cgcatgatcg cg                              32

<210> SEQ ID NO 11
<211> LENGTH: 31
<212> TYPE: DNA
<213> ORGANISM: Artificial Sequence
<220> FEATURE:
<223> OTHER INFORMATION: Synthetic oligonucleotide probe

<400> SEQUENCE: 11
cgcgatcgaa caagctgctg caacagatcg c                               31

<210> SEQ ID NO 12
<211> LENGTH: 20
<212> TYPE: DNA
<213> ORGANISM: Artificial Sequence
<220> FEATURE:

<223> OTHER INFORMATION: Synthetic oligonucleotide primer

<400> SEQUENCE: 12
gacgaacggg ataccacaac                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
cattctgctc cacgttcaag                                          20

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 14
cgaacgggat accacaaca                                           19

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 15
cattctgctc cacgttcaag g                                        21

<210> SEQ ID NO 16
<211> LENGTH: 11
<212> TYPE: DNA
<213> ORGANISM: Artificial Sequence
<220> FEATURE:
<223> OTHER INFORMATION: Synthetic oligonucleotide primer

<400> SEQUENCE: 16
catctggaca a                                                   11

<210> SEQ ID NO 17
<211> LENGTH: 11
<212> TYPE: DNA
<213> ORGANISM: Artificial Sequence
<220> FEATURE:
<223> OTHER INFORMATION: Synthetic oligonucleotide primer

<400> SEQUENCE: 17
ttcgcattct g                                                   11

<210> SEQ ID NO 18
<211> LENGTH: 10
<212> TYPE: DNA
<213> ORGANISM: Artificial Sequence
<220> FEATURE:
<223> OTHER INFORMATION: Synthetic oligonucleotide primer

<400> SEQUENCE: 18
tcgcattctg                                                     10

```
<210> SEQ ID NO 19
<211> LENGTH: 11
<212> TYPE: DNA
<213> ORGANISM: Artificial Sequence
<220> FEATURE:
<223> OTHER INFORMATION: Synthetic oligonucleotide primer

<400> SEQUENCE: 19
ttcgcattct g                                                        11

<210> SEQ ID NO 20
<211> LENGTH: 11
<212> TYPE: DNA
<213> ORGANISM: Artificial Sequence
<220> FEATURE:
<223> OTHER INFORMATION: Synthetic oligonucleotide primer

<400> SEQUENCE: 20
ataccacaac a                                                        11

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 21
atccaatcgg tgagcagtgc                                               20

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 22
atcgaccgaa tgtcgtcac                                                19

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 23
atccaatcgg tgagcagtgc                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 24
tcgaccgaat gtcgtcactg                                               20

<210> SEQ ID NO 25
<211> LENGTH: 11
<212> TYPE: DNA
<213> ORGANISM: Artificial Sequence
<220> FEATURE:
<223> OTHER INFORMATION: Synthetic oligonucleotide primer
```

```
<400> SEQUENCE: 25
atagcgtatc g                                                      11

<210> SEQ ID NO 26
<211> LENGTH: 11
<212> TYPE: DNA
<213> ORGANISM: Artificial Sequence
<220> FEATURE:
<223> OTHER INFORMATION: Synthetic oligonucleotide primer

<400> SEQUENCE: 26
actggtgtag g                                                      11

<210> SEQ ID NO 27
<211> LENGTH: 10
<212> TYPE: DNA
<213> ORGANISM: Artificial Sequence
<220> FEATURE:
<223> OTHER INFORMATION: Synthetic oligonucleotide primer

<400> SEQUENCE: 27
tgtcgtcact                                                        10

<210> SEQ ID NO 28
<211> LENGTH: 11
<212> TYPE: DNA
<213> ORGANISM: Artificial Sequence
<220> FEATURE:
<223> OTHER INFORMATION: Synthetic oligonucleotide primer

<400> SEQUENCE: 28
actggtgtag g                                                      11

<210> SEQ ID NO 29
<211> LENGTH: 10
<212> TYPE: DNA
<213> ORGANISM: Artificial Sequence
<220> FEATURE:
<223> OTHER INFORMATION: Synthetic oligonucleotide primer

<400> SEQUENCE: 29
gccatccaat                                                        10

<210> SEQ ID NO 30
<211> LENGTH: 1521
<212> TYPE: DNA
<213> ORGANISM: Mycobacterium smegmatis

<400> SEQUENCE: 30
atgtcagccg gttcggcacc gctcgtaacg ccacggcgga aaaacgcgct gcacgccgcc      60
accgcgtcac gcacggcgcg ctaccgtcga ccggtgaggc tgtcccggtc gcgcgtgccg     120
cggctctgcg ccatcggtgc tgttttcgcc gtggtggccg cgacatcgtg cagccggccc     180
gcacccgcgc ctcgtgaacc ggccccggcg accggcattg ccgccgcctc cccggccccg     240
accgcgcccc cgacgcaggt gacccagccc gtgaccccga cgggtgactt ctcggcggtc     300
acccggctcg tcgacgacgc cgtcgccgca cgccggctgc ccggtgcggt ggtccagatc     360
gggcacgcgg gcaagatcgt gttccgcgcg gcgttcggtg cgcgcaagct cgacggcgaa     420
ccgggcctgg acggttcccc gtcacccgcc gaaccgatga ccgaggacac cctgttcgac     480
ctggcgtccc tgacgaagag catcgcgacg acgacggccg tcctgcagct ctacgagcag     540
ggcaagatcc gcctcgacga gcccgtgcag acgtacctgc cggacttcaa ccccaccggc     600
```

```
gatccgcgcc gtgcccgggt gacgttgcgc atgttgctca cccacacatc gggtatcgcg      660
ggcgatctga gcctcgacgg gccgtggggg ctgaccgcgg ccgacaaggc cgagggcgtc      720
aagcgtgcgc tggccgcgtg ggtggtgttc gagcccggcg cgatgttcca ctactccgat      780
atcgggttca tcattctggg caccctggtc gagaagatca ccggacaatc cctggacggc      840
tacgtgcgcg agcatgtgtt cgcaccgctc ggcatgtccg acacgtacta cctgcccgcc      900
gcgaacgcgt gcgaccgcca cgagatacgc ggcaacgcac tggtttccga tccggacgga      960
ccgcggacga ccgactgccc ggccgattcc tggagcacgg gcctgctgac ccgggtcgcc     1020
cccaccgcgc tcgacgagga caccccgggc atcaacccgc atttcgggct gcccctgcgc     1080
ggaaccgtgc acgacccgac ggcacgccgc atgggcgggg tggccggaag cgcgggcgtg     1140
ttcacgacgg ttcacgacct gggcctgttc gcgcaggcgt tgctcgaccg acgggccaac     1200
cgccccagca cttttccgct gcagcaggcg acggtcgaac tgatgaccac accacagcag     1260
cccggcgccg accagatctg cgtggtctg ggctgggaca tcgacacgcc gcactcgcga     1320
ccacgcggca cggtgttccc ggtcggcagc ttcggccaca ccgggttcac cggggtctcg     1380
atgtggatgg accctggatc ggacacctac gtgatcgtcc tggcgaacgt catccatcag     1440
cgcggcggcc cgccgatcgc gacgctcagc ggtgacgtgg ccaccgaggc cgcgcgtgcg     1500
ctgcaccttt acgggacttg a                                               1521

<210> SEQ ID NO 31
<211> LENGTH: 401
<212> TYPE: PRT
<213> ORGANISM: Mycobacterium smegmatis

<400> SEQUENCE: 31

Met Asn Leu Asp Ala Asn Gln Ala Asp Ile Arg Glu Val Cys Asp Ala
1               5                   10                  15

Gly Leu Leu Ser Gly Ala Val Thr Val Val Trp Gln His Gly Glu Val
            20                  25                  30

Leu Gln Val Asn Glu Ile Gly Tyr Arg Asp Val Glu Ala Gly Leu Pro
        35                  40                  45

Met Gln Arg Asp Thr Leu Phe Arg Ile Ala Ser Met Thr Lys Pro Val
    50                  55                  60

Thr Val Ala Ala Ala Met Ser Met Val Asp Glu Gly Lys Met Ala Leu
65                  70                  75                  80

Arg Asp Pro Ile Thr Arg Trp Ala Pro Glu Leu Arg Asp Ile Arg Val
                85                  90                  95

Leu Asp Asp Pro His Gly Pro Leu Asp Arg Thr His Pro Thr Arg Arg
            100                 105                 110

Pro Ile Leu Ile Glu Asp Leu Leu Thr His Thr Ser Gly Leu Ala Tyr
        115                 120                 125

Ser Phe Ser Val Ser Gly Asp Ile Ser Arg Ala Tyr Met Arg Leu Pro
    130                 135                 140

Phe Gly His Gly Ser Asp Ala Trp Leu Ala Glu Leu Ala Ala Leu Pro
145                 150                 155                 160

Leu Val His Gln Pro Gly Glu Arg Val Thr Tyr Ser His Ala Ile Asp
                165                 170                 175

Leu Leu Gly Val Ile Met Ser Arg Ile Asp Asp Lys Pro Phe Tyr Gln
            180                 185                 190

Val Leu Asp Glu Arg Ile Leu Gly Pro Ala Gly Met Thr Asp Thr Gly
        195                 200                 205
```

```
Phe Phe Val Ser Thr Gln Ala Gln Arg Arg Ala Ala Thr Met Tyr Arg
    210                 215                 220
Leu Asp Glu Leu Asp Gln Leu Arg His Asp Val Met Gly Pro Pro His
225                 230                 235                 240
Val Arg Pro Pro Ser Phe Cys Asn Ala Gly Gly Gly Leu Trp Ser Thr
                245                 250                 255
Ala Asp Asp Tyr Leu Arg Phe Val Arg Leu Leu Leu Gly Asp Gly Thr
                260                 265                 270
Ile Asp Gly Val Arg Val Leu Ser Pro Glu Ser Val Arg Leu Met Arg
            275                 280                 285
Thr Asp Arg Leu Ser Asp Glu His Lys Arg His Asn Phe Leu Gly Ala
290                 295                 300
Pro Phe Trp Val Gly Arg Gly Phe Gly Leu Asn Leu Ser Val Val Thr
305                 310                 315                 320
Asp Pro Ala Gln Ser Thr Pro Leu Phe Gly Pro Gly Leu Gly Thr
                325                 330                 335
Phe Ser Trp Pro Gly Ala Tyr Gly Thr Trp Trp Gln Ala Asp Pro Gly
            340                 345                 350
Ala Asp Leu Ile Leu Leu Tyr Leu Ile Gln His Cys Pro Asp Leu Ser
            355                 360                 365
Val Asn Ala Ala Ala Val Ala Gly Asn Pro Gly Leu Ala Lys Leu
        370                 375                 380
Arg Thr Ala Gln Pro Arg Phe Val Arg Arg Thr Tyr Arg Ala Leu Gly
385                 390                 395                 400
Leu

<210> SEQ ID NO 32
<211> LENGTH: 1201
<212> TYPE: DNA
<213> ORGANISM: Mycobacterium marinum

<400> SEQUENCE: 32
gtgaatctcg acgccaacca ggctgatatc cgcgaggtct ccggattgct ctccggcgca     60
gtgaccgtgg tttggcagca cggagaagta ctgcaggtca cgaaatcgg ctaccgagac    120
gtcgaggcgg gcctgccgat gcagcgcgac acgctgtttc gcatcgcgtc catgaccaaa    180
cccgtcaccg ttgccgcggc catgagcatg gtcgacgagg caaaatggc cctgcgtgac    240
ccgatcacac gctgggcgcc cgagttgcgc gacatccggg tgcttgacga cccgcacggc    300
ccgttggacc gcacgcaccc cacccgacgg ccgatcctca tcgaggacct gctgacccac    360
accagcgggc tggcctacag ttttcggtg tccggagaca tttcgcgggc gtacatgcga    420
ttgccatttg gtcatggttc cgacgcctgg ctggccgaac tcgccgcgct gccactggtg    480
caccagcccg cgagcgggt cacctacagc cacgccatcg atctgctcgg cgtcatcatg    540
tcccgcatcg acgacaagcc tttctaccag gtgctcgacg agcgaatact gggcccggcc    600
ggcatgaccg acaccggctt cttcgtgtcg acacaggccc agcgccgcgc cgcaaccatg    660
taccgcctcg acgagctgga ccagctacgg cacgacgtca tgggcccgcc gcacgtgcgg    720
cctccgtcgt tctgcaacgc cggcggcgga ttgtggtcaa ccgccgacga ctacctgaga    780
tttgtccggc tactgctcgg cgacgggacg atcgacggcg ttcgggtgct ctcaccggag    840
tcggtgcggc tgatgcgcac cgaccggctc agcgacgagc acaagcgaca caactttctc    900
ggggcgccct ctgggtggg ccgcgggttc gggctgaacc tgtcggtggt gaccgacccg    960
```

-continued

```
gctcagtcca ctccactgtt cggcccgggc gggcttggca ccttcagctg gcccggtgcc    1020
tacgggacct ggtggcaggc cgatcctggc gccgacctga tcctgctgta tctgattcag    1080
cattgtcccg acttgtccgt gaacgcggcg gctgcggtcg cggggcaacc cggggctggc    1140
caagctgcgc acggcacaac cccggttcgt ccggcgcacc taccgcgcgc tcggactgta    1200
g                                                                    1201
```

<210> SEQ ID NO 33
<211> LENGTH: 311
<212> TYPE: PRT
<213> ORGANISM: Mycobacterium marinum

<400> SEQUENCE: 33

```
Met Arg Pro Ser Asn Pro Arg Ser Ala Val Asn Arg Arg Gln Leu Leu
1               5                   10                  15

Ala Ala Met Ala Ala Leu Leu Pro Leu Ser Ala Cys Ala Lys Ala Ala
            20                  25                  30

Ser Asp Gln His Met Ala Ser Thr Met Ala Val Pro Ser Pro Asp Leu
        35                  40                  45

Glu Ser Arg Phe Ala Glu Leu Glu Gln Lys Tyr Glu Ala Arg Leu Gly
    50                  55                  60

Val Tyr Val Pro Gly Thr Asp Ala Thr Ala Val Glu His Arg Gly
65                  70                  75                  80

Asp Glu Arg Phe Ala Phe Cys Ser Thr Phe Lys Gly Leu Leu Gly Ala
                85                  90                  95

Ala Val Leu His Arg Tyr Pro Ile Ala His Leu Gly Thr Val Ile Thr
            100                 105                 110

Tyr Asn Ser Ala Asp Ile Arg Ser Thr Ser Pro Ile Thr Glu Gln His
        115                 120                 125

Leu Ala Thr Gly Met Ser Ile Gly Gly Leu Cys Asp Ala Thr Ile Arg
    130                 135                 140

Tyr Ser Asp Gly Thr Ala Ala Asn Leu Leu Leu Gln Asp Ile Gly Gly
145                 150                 155                 160

Ile Ala Ala Phe Asn Glu Tyr Leu Arg Ser Leu Gly Asp Ser Val Ser
                165                 170                 175

Arg Leu Asp Gln Met Glu Pro Glu Leu Asn Arg Asn Pro Pro Gly Asp
            180                 185                 190

Val Arg Asp Thr Thr Thr Pro His Ala Ile Ala Met Asp Tyr Gln Gln
        195                 200                 205

Val Val Leu Gly Asp Ala Leu Leu Pro Glu Lys Arg Asp Lys Leu Ile
    210                 215                 220

Asp Trp Leu Gly Arg Ser Thr Thr Gly Ala Lys Arg Ile Arg Ala Gly
225                 230                 235                 240

Phe Pro Ala Asp Trp Arg Val Ile Asp Lys Thr Gly Ser Gly Glu Tyr
                245                 250                 255

Gly Arg Ala Asn Asp Val Ala Val Val Trp Ser Pro Gly Gly Thr Pro
            260                 265                 270

Tyr Val Val Ala Ile Met Thr Asp Arg Val Gly Gly Pro Glu Ala
        275                 280                 285

Pro Trp Cys Asp Pro Leu Val Ala Asp Ala Ala Lys Cys Val Ala Asp
    290                 295                 300

Val Leu Ala Gln Trp Ser Ala
305                 310
```

<210> SEQ ID NO 34
<211> LENGTH: 861
<212> TYPE: DNA
<213> ORGANISM: Escherichia coli

<400> SEQUENCE: 34

```
atgagtattc aacattttcg tgtcgccctt attcccttt ttgcggcatt ttgccttcct      60
gttttgctc acccagaaac gctggtgaaa gtaaagatg ctgaagatca gttgggtgca      120
cgagtgggtt acatcgaact ggatctcaac agcggtaaga tccttgagag ttttcgcccc      180
gaagaacgtt ttccaatgat gagcactttt aaagttctgc tatgtggtgc ggtattatcc      240
cgtgttgacg ccgggcaaga gcaactcggt cgccgcatac actattctca gaatgacttg      300
gttgagtact caccagtcac agaaaagcat cttacggatg catgacagt aagagaatta      360
tgcagtgctg ccataaccat gagtgataac actgctgcca acttacttct gacaacgatc      420
ggaggaccga aggagctaac cgcttttttg cacaacatgg gggatcatgt aactcgcctt      480
gatcgttggg aaccggagct gaatgaagcc ataccaaacg acgagcgtga caccacgatg      540
cctgcagcaa tggcaacaac gttgcgcaaa ctattaactg gcgaactact tactctagct      600
tcccggcaac aattaataga ctggatggag gcggataaag ttgcaggacc acttctgcgc      660
tcggcccttc cggctggctg gtttattgct gataaatctg gagccggtga gcgtgggtct      720
cgcggtatca ttgcagcact ggggccagat ggtaagccct cccgtatcgt agttatctac      780
acgacgggga gtcaggcaac tatggatgaa cgaaatagac agatcgctga gataggtgcc      840
tcactgatta agcattggta a                                              861
```

<210> SEQ ID NO 35
<211> LENGTH: 286
<212> TYPE: PRT
<213> ORGANISM: Escherichia coli

<400> SEQUENCE: 35

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
```

```
              180                 185                 190
Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
        210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 36
<211> LENGTH: 789
<212> TYPE: DNA
<213> ORGANISM: Pseudomonas aeruginosa

<400> SEQUENCE: 36
atgcgccctc tcctcttcag tgcccttctc ctgctttccg gcatacccca ggccagcgaa    60
tggaacgaca gccaggccgt ggacaagcta ttcggcgcgg ccggggtgaa aggcaccttc   120
gtcctctacg atgtgcagcg gcagcgctat gtcggccatg accggagcg cgcggaaacc   180 cgcttcgttc ccgcttccac ctacaaggtg gcgaacagcc tgatcggctt atccacaggg   240
gcggttagat ccgccgacga ggttcttccc tatggcggca agcccagcg cttcaaggcc   300 tgggagcacg acatgagcct gcgcgacgcg atcaaggcat cgaacgtacc ggtctaccag   360
gaactggcgc ggcgcatcgg cctggagcgg atgcgcgcca tgtctcgcg cctgggttac   420 ggcaacgcgg aaatcggcca ggttgtggat aacttctggt tggtgggacc gctgaagatc   480
agcgcgatgg aacagacccg ctttctgctc cgactggcgc aggagaatt gccattcccc   540 gccccggtgc agtccaccgt gcgcgccatg accctgctgg aaagcggccc gggctgggag   600
ctgcacggca agaccggctg tgtgcttcgac tgcacgccgg aactcggctg gtgggtgggc   660
tgggtgaagc gcaacgagcg gctctacggc ttcgccctga acatcgacat gcccggcggc   720
gaggccgaca tcggcaagcg cgtcgaactg ggcaaggcca gtctcaaggc tctcgggata   780
ctgccctga                                                           789

<210> SEQ ID NO 37
<211> LENGTH: 262
<212> TYPE: PRT
<213> ORGANISM: Pseudomonas aeruginosa

<400> SEQUENCE: 37

Met Arg Pro Leu Leu Phe Ser Ala Leu Leu Leu Ser Gly His Thr
1               5                   10                  15

Gln Ala Ser Glu Trp Asn Asp Ser Gln Ala Val Asp Lys Leu Phe Gly
            20                  25                  30

Ala Ala Gly Val Lys Gly Thr Phe Val Leu Tyr Asp Val Gln Arg Gln
        35                  40                  45

Arg Tyr Val Gly His Asp Arg Glu Arg Ala Glu Thr Arg Phe Val Pro
    50                  55                  60

Ala Ser Thr Tyr Lys Val Ala Asn Ser Leu Ile Gly Leu Ser Thr Gly
65                  70                  75                  80
```

```
Ala Val Arg Ser Ala Asp Glu Val Leu Pro Tyr Gly Gly Lys Pro Gln
                85                  90                  95

Arg Phe Lys Ala Trp Glu His Asp Met Ser Leu Arg Asp Ala Ile Lys
            100                 105                 110

Ala Ser Asn Val Pro Val Tyr Gln Glu Leu Ala Arg Arg Ile Gly Leu
        115                 120                 125

Glu Arg Met Arg Ala Asn Val Ser Arg Leu Gly Tyr Gly Asn Ala Glu
    130                 135                 140

Ile Gly Gln Val Val Asp Asn Phe Trp Leu Val Gly Pro Leu Lys Ile
145                 150                 155                 160

Ser Ala Met Glu Gln Thr Arg Phe Leu Leu Arg Leu Ala Gln Gly Glu
                165                 170                 175

Leu Pro Phe Pro Ala Pro Val Gln Ser Thr Val Arg Ala Met Thr Leu
            180                 185                 190

Leu Glu Ser Gly Pro Gly Trp Glu Leu His Gly Lys Thr Gly Trp Cys
        195                 200                 205

Phe Asp Cys Thr Pro Glu Leu Gly Trp Trp Val Gly Trp Val Lys Arg
    210                 215                 220

Asn Glu Arg Leu Tyr Gly Phe Ala Leu Asn Ile Asp Met Pro Gly Gly
225                 230                 235                 240

Glu Ala Asp Ile Gly Lys Arg Val Glu Leu Gly Lys Ala Ser Leu Lys
                245                 250                 255

Ala Leu Gly Ile Leu Pro
            260

<210> SEQ ID NO 38
<211> LENGTH: 830
<212> TYPE: DNA
<213> ORGANISM: Staphylococcus aureus

<400> SEQUENCE: 38
ttgaaaaagt taatattttt aattgcaatt gctttagttt taagtgcatg taattcaaac      60
agtccacatg ccaaagagtt aatgatttag aaaaaaaata taatgctcat attggtgttt     120
atgctttaga tactaaaagt ggtaaggaag taaaatttaa ttcagataag agatttgcct     180
atgcttcgac ttcaaaagcg ataaatagtg ctattttgtt agaacaagta ccttataata     240
agttaaataa aaaatacat attaacaaag atgatatagt tgcttattct cctattttag      300
aaaaatatgt aggaaaagat atcactttaa agaacttat tgaggcttca atgacatata     360
gtgataatac agcaaacaat aaaattataa aagaaatcgg tggaatcaaa aaagttaaac     420
aacgtctaaa agaactagga gataaagtaa caaatccagt tagatatgag atagaattaa     480
attactattc accaaagagc aaaaaagata cttcaacacc tgctgctttc ggtaagactt     540
taaataaact tatcgcaaat ggaaaattag aaaacaaaaa attcttactt gatttaatgt     600
taaataataa aagcggagat actttaatta aagacggtgt tccaaaagac tataaggttg     660
ctgataaaag tggtcaagca ataacatatg cttctagaaa tgatgttgct tttgtttatc     720
ctaagggcca atctgtttta gtcattttta cgaataaaga caataaaagt gataagccaa     780
atgataagtt gataagtgaa accgccaaga gtgtaatgaa ggaattttaa                830

<210> SEQ ID NO 39
<211> LENGTH: 303
<212> TYPE: PRT
<213> ORGANISM: Staphylococcus aureus

<400> SEQUENCE: 39
```

```
Met Gln Lys Phe Asp Thr Arg Thr Phe Gln Gly Leu Ile Leu Thr Leu
1               5                   10                  15

Gln Asp Tyr Trp Ala Arg Gln Gly Cys Thr Ile Val Gln Pro Leu Asp
            20                  25                  30

Met Glu Val Gly Ala Gly Thr Ser His Pro Met Thr Cys Leu Arg Ala
        35                  40                  45

Leu Gly Pro Glu Pro Met Ala Ala Tyr Val Gln Pro Ser Arg Arg
    50                  55                  60

Pro Thr Asp Gly Arg Tyr Gly Glu Asn Pro Asn Arg Leu Gln His Tyr
65                  70                  75                  80

Tyr Gln Phe Gln Val Val Ile Lys Pro Ser Pro Asp Asn Ile Gln Glu
                85                  90                  95

Leu Tyr Leu Gly Ser Leu Lys Glu Leu Gly Met Asp Pro Thr Ile His
                100                 105                 110

Asp Ile Arg Phe Val Glu Asp Asn Trp Glu Asn Pro Thr Leu Gly Ala
            115                 120                 125

Trp Gly Leu Gly Trp Glu Val Trp Leu Asn Gly Met Glu Val Thr Gln
    130                 135                 140

Phe Thr Tyr Phe Gln Gln Val Gly Gly Leu Glu Cys Lys Pro Val Thr
145                 150                 155                 160

Gly Glu Ile Thr Tyr Gly Leu Glu Arg Leu Ala Met Tyr Ile Gln Gly
                165                 170                 175

Val Asp Ser Val Tyr Asp Leu Val Trp Ser Asp Gly Pro Leu Gly Lys
            180                 185                 190

Thr Thr Tyr Gly Asp Val Phe His Gln Asn Glu Val Glu Gln Ser Thr
            195                 200                 205

Tyr Asn Phe Glu Tyr Ala Asp Val Asp Phe Leu Phe Thr Cys Phe Glu
    210                 215                 220

Gln Tyr Glu Lys Glu Ala Gln Gln Leu Leu Ala Leu Glu Asn Pro Leu
225                 230                 235                 240

Pro Leu Pro Ala Tyr Glu Arg Ile Leu Lys Ala Ala His Ser Phe Asn
                245                 250                 255

Leu Leu Asp Ala Arg Lys Ala Ile Ser Val Thr Glu Arg Gln Arg Tyr
            260                 265                 270

Ile Leu Arg Ile Arg Thr Leu Thr Lys Ala Val Ala Glu Ala Tyr Tyr
    275                 280                 285

Ala Ser Arg Glu Ala Leu Gly Phe Pro Met Cys Asn Lys Asp Lys
    290                 295                 300

<210> SEQ ID NO 40
<211> LENGTH: 421
<212> TYPE: PRT
<213> ORGANISM: Streptococcus pneumoniae

<400> SEQUENCE: 40

Met Arg Lys Phe Leu Ile Ile Leu Leu Pro Ser Phe Leu Thr Ile
1               5                   10                  15

Ser Lys Val Val Ser Thr Glu Lys Glu Val Val Tyr Thr Ser Lys Glu
            20                  25                  30

Ile Tyr Tyr Leu Ser Gln Ser Asp Phe Gly Ile Tyr Phe Arg Glu Lys
        35                  40                  45

Leu Ser Ser Pro Met Ala Tyr Gly Glu Val Pro Val Tyr Ala Asn Glu
    50                  55                  60

Asp Leu Val Val Glu Ser Gly Lys Leu Thr Pro Lys Thr Ser Phe Gln
```

```
            65                  70                  75                  80
Ile Thr Glu Trp Arg Leu Asn Lys Gln Gly Ile Pro Val Phe Lys Leu
                85                  90                  95

Ser Asn His Gln Phe Ile Ala Ala Asp Lys Arg Phe Leu Tyr Asp Gln
                100                 105                 110

Ser Glu Val Thr Pro Thr Ile Lys Lys Val Trp Leu Glu Ser Asp Phe
                115                 120                 125

Lys Leu Tyr Asn Ser Pro Tyr Asp Leu Lys Glu Val Lys Ser Ser Leu
            130                 135                 140

Ser Ala Tyr Ser Gln Val Ser Ile Asp Lys Thr Met Phe Val Glu Gly
145                 150                 155                 160

Arg Glu Phe Leu His Ile Asp Gln Ala Gly Trp Val Ala Lys Glu Ser
                165                 170                 175

Thr Ser Glu Glu Asp Asn Arg Met Ser Lys Val Gln Glu Met Leu Ser
                180                 185                 190

Glu Lys Tyr Gln Lys Asp Ser Phe Ser Ile Tyr Val Lys Gln Leu Thr
            195                 200                 205

Thr Gly Lys Glu Ala Gly Ile Asn Gln Asp Glu Lys Met Tyr Ala Ala
            210                 215                 220

Ser Val Leu Lys Leu Ser Tyr Leu Tyr Tyr Thr Gln Glu Lys Ile Asn
225                 230                 235                 240

Glu Gly Leu Tyr Gln Leu Asp Thr Thr Val Lys Tyr Val Ser Ala Val
                245                 250                 255

Asn Asp Phe Pro Gly Ser Tyr Lys Pro Glu Gly Ser Gly Ser Leu Pro
                260                 265                 270

Lys Lys Glu Asp Asn Lys Glu Tyr Ser Leu Lys Asp Leu Ile Thr Lys
            275                 280                 285

Val Ser Lys Glu Ser Asp Asn Val Ala His Asn Leu Leu Gly Tyr Tyr
            290                 295                 300

Ile Ser Asn Gln Ser Asp Ala Thr Phe Lys Ser Lys Met Ser Ala Ile
305                 310                 315                 320

Met Gly Asp Asp Trp Asp Pro Lys Glu Lys Leu Ile Ser Ser Lys Met
                325                 330                 335

Ala Gly Lys Phe Met Glu Ala Ile Tyr Asn Gln Asn Gly Phe Val Leu
                340                 345                 350

Glu Ser Leu Thr Lys Thr Asp Phe Asp Ser Gln Arg Ile Ala Lys Gly
            355                 360                 365

Val Ser Val Lys Val Ala His Lys Ile Gly Asp Ala Asp Glu Phe Lys
370                 375                 380

His Asp Thr Gly Val Val Tyr Ala Asp Ser Pro Phe Ile Leu Ser Ile
385                 390                 395                 400

Phe Thr Lys Asn Ser Asp Tyr Asp Thr Ile Ser Lys Ile Ala Lys Asp
                405                 410                 415

Val Tyr Glu Val Leu
                420
```

BETA LACTAMASE AS BIOMARKER FOR THE SPECIFIC DETECTION OF TUBERCULOSIS-COMPLEX BACTERIA

CROSS-REFERENCES TO RELATED APPLICATIONS

This application is a division of U.S. patent application Ser. No. 15/504,633, filed Feb. 16, 2017, which is the National Stage of International Patent Application No. PCT/US2015/045572, filed Aug. 17, 2015, which claims the benefit of U.S. Provisional Application No. 62/134,332, filed Mar. 17, 2015, and U.S. Provisional Application No. 62/038,736, filed Aug. 18, 2014, all of which applications are incorporated herein by reference in their entireties.

STATEMENT REGARDING SEQUENCE LISTING

The sequence listing associated with this application is provided in text format in lieu of a paper copy and is hereby incorporated by reference into the specification. The name of the text file containing the sequence listing is 54434_seq_ST25.txt. The text file is 16 KB; was originally created on Aug. 17, 2015; was previously submitted on Aug. 17, 2015, as part of International Application No. PCT/US2015/045572, and on Feb. 16, 2017, as part of U.S. patent application Ser. No. 15/504,633, and is being submitted via EFS-Web with the filing of this specification.

BACKGROUND

Tuberculosis (TB) is one of the most important infectious diseases in humans and animals worldwide. The World Health Organization currently estimates that roughly one-third of the world's population is infected with tuberculosis (TB), caused by the *Mycobacterium tuberculosis* (Mtb). In the year 2011 alone, 8.7 million people fell ill with TB and another 1.4 million died. While the risk of developing symptoms from the latent condition is only 10%, this number increases greatly if the individual is also infected with an immune compromising disease such as HIV. TB is a treatable and curable disease, typically combated with a six-month course of antimicrobial drugs, and the use of these treatments has significantly decreased the mortality rate for TB over the last quarter century. Despite this, multi-drug resistant TB strains generate concern among medical experts and demand the need for the development of new antimicrobial strategies. One important component to treatment strategies is the implementation of effective and accurate diagnosis and tracking of infections, including latent infections. Such diagnostic strategies could dramatically enhance the ability to detect infection and potentially prevent transmission, thus reducing the overall incidence of TB.

Early diagnosis is critical to the prevention and control of tuberculosis due to its airborne transmission. Standard diagnostic methods, such as an acid-fast stain on smears from sputum, do not become positive until after transmission can occur, allowing spread of disease. Culture-based techniques are more sensitive, but take weeks to obtain results, due to the extremely slow growth rate of TB bacteria. Thus, clinical diagnosis and disease control would be greatly facilitated by methods that can detect tubercle bacteria in a sensitive, rapid, specific and quantitative manner during disease.

In addition to this, the current vaccine, *Mycobacterium bovis Bacillus* Calmette Guerin (BCG), displays variable efficacy (0-80%) depending on the population being vaccinated. Currently, researchers typically rely on animal studies to help assess the effectiveness of new therapeutic agents. These studies employ sacrifice at discrete time points, tissue homogenization, and colony growth. These factors combine to greatly limit temporal and spatial resolution of the bacteria in tissue. Thus, the development of an experimental technique that could provide rapid feedback regarding the efficacy of a therapeutic agent in an animal model of a respiratory infection could greatly benefit the development of such vaccines.

Despite the advances in the development of diagnostic techniques for the diagnosis and monitoring of TB infections, a need remains for sensitive, rapid, and specific diagnostic reagents and methods that facilitate the rapid detection of tuberculosis. The present invention seeks to fulfill this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides an affinity reagent that specifically binds to a β-lactamase (BlaC), or a portion thereof, of a tuberculosis-complex bacteria.

In some embodiments, the BlaC has an amino acid sequence with at least 95% identity to the sequence set forth in SEQ ID NO:2. In some embodiments, the BlaC has an amino acid sequence set forth in SEQ ID NO:2. In some embodiments, the affinity reagent is capable of specifically binding to a portion of BlaC.

In some embodiments, the affinity reagent is an antibody, an enzyme substrate, a modified enzyme substrate, and the like. In some embodiments, the affinity reagent is a polyclonal or monoclonal antibody.

In some embodiments, the tuberculosis-complex bacteria are from one or more of the species selected from the group consisting of: *Mycobacterium tuberculosis, Mycobacterium bovis, Mycobacterium bovis-Bacillus* Calmette-Guerin (BCG), *Mycobacterium africanum, Mycobacterium microti, Mycobacterium canettii, Mycobacterium pinnipedii,* and *Mycobacterium mungi.*

In another aspect, the disclosure provides a method of detecting the presence of tuberculosis-complex bacteria in a biological sample, the method comprising 1) contacting the sample with an affinity reagent that specifically binds to a β-lactamase (BlaC) of a tuberculosis-complex bacterium, and 2) detecting the formation of a complex between the BlaC and the affinity reagent. The formation of a complex is indicative of the presence of tuberculosis-complex bacteria in the sample.

In some embodiments, the BlaC has an amino acid sequence with at least 95% identity to the sequence set forth in SEQ ID NO:2. In some embodiments, the BlaC has an amino acid sequence set forth in SEQ ID NO:2. In some embodiments, the affinity reagent is capable of specifically binding to a portion of the BlaC.

In some embodiments, the affinity reagent comprises a detectable label. In some embodiments, the method further comprises contacting the biological sample with an immobilized BlaC protein or affinity reagent. In some embodiments, the affinity reagent is attached to a substrate. In some embodiments, the formation of a complex between the BlaC and the affinity reagent is detected by further contacting the complex with a second affinity reagent that contains a detectable label and that specifically binds to the complex.

In some embodiments, the biological sample is obtained from a subject suspected of having tuberculosis-complex bacteria, and wherein the presence of tuberculosis-complex bacteria in the biological sample is indicative of a tuberculosis infection in the subject. In some embodiments, the biological sample comprises blood, serum, sputum, saliva, breath, feces, urine, spinal fluid, mucus, tissue sample, and the like. In some embodiments, the subject is a mammal, such as a human.

In another aspect, the disclosure provides a method of detecting the presence of tuberculosis-complex bacteria in a biological sample obtained from a subject, the method comprising determining the presence or amount of anti-β-lactamase (BlaC) antibody in a biological sample, wherein the presence or amount of anti-BlaC antibody in the biological sample is indicative of the presence of tuberculosis-complex bacteria in the subject.

In some embodiments, the presence of anti-BlaC antibody in the biological sample is determined by an assay comprising the following steps:

(a) contacting the biological sample with at least one polypeptide with an amino acid sequence that has at least 90% sequence identity to any six or more contiguous amino acids of SEQ ID NO:2; and (b) detecting the formation of a complex between the antibody in the sample and the polypeptide.

In some embodiments, the method further comprises comparing the determined amount of anti-BlaC antibody to a reference standard, where an amount of anti-BlaC antibody detected in the biological sample greater than the reference standard is indicative of the presence of tuberculosis-complex bacteria in the subject. In some embodiments, the reference standard is an analogous biological sample from a subject that does not have tuberculosis-complex bacteria.

In another aspect, the present disclosure provides a method for detecting the presence of tuberculosis-complex bacteria in a test sample, the method comprising:

(a) contacting the sample with a polynucleotide probe with a detectable label capable of specifically hybridizing to a target region of a nucleic acid molecule that encodes a β-lactamase (BlaC) with an amino acid sequence set forth in SEQ ID NO:2, and (b) detecting the hybridization of the probe to the nucleic acid molecule encoding BlaC, wherein detected hybridization is indicative of the presence of tuberculosis-complex bacteria in the test sample.

In some embodiments, the polynucleotide probe has a polynucleotide sequence selected from the group consisting of SEQ ID NO:3, 4, 5, 6, 7, 8, 9, 10, and 11.

In some embodiments, the method further comprises contacting the sample with a forward polynucleotide primer and a reverse primer to form a reaction mixture, wherein each primer capable of specifically hybridizing to a different portion of the target region, and subjecting the reaction mixture to amplification conditions suitable to amplify at least a portion of the target region. In some embodiments, the forward primer has a polynucleotide sequence selected from the group consisting of SEQ ID NO:12, 13, 14, 15, 16, 17, 18, 19, and 20. In some embodiments, the reverse primer has a polynucleotide sequence selected from the group consisting of SEQ ID NO:21, 22, 23, 24, 25, 26, 27, 28, and 29. In some embodiments, the test sample is obtained from a subject suspected of having tuberculosis-complex bacteria, and wherein the presence of tuberculosis-complex bacteria in the biological sample is indicative of a tuberculosis infection in the subject.

In another aspect, the present disclosure provides a method for determining the presence of tuberculosis complex bacteria in a test sample, the method comprising the steps of:

(a) contacting the test sample with a composition comprising at least one primer pair comprising a forward and reverse primer capable of specifically hybridizing to a target region of tuberculosis complex blaC gene, to form a reaction mixture;

(b) subjecting said reaction mixture to amplification conditions suitable to amplify at least a portion of the target region; and (c) detecting amplification of the at least a portion of the target region, wherein amplification of the at least a portion of the target region is indicative of the presence of tuberculosis complex bacteria in a test sample.

In some embodiments, the primer pair is selected from the group consisting of SEQ ID NOS:12 and 21, SEQ ID NOS:13 and 22, SEQ ID NOS:14 and 23, SEQ ID NOS:15 and 24, SEQ ID NOS:16 and 25, SEQ ID NOS:17 and 26, SEQ ID NOS:18 and 27, SEQ ID NOS:19 and 28, and SEQ ID NOS:20 and 29.

In another aspect, the present disclosure provides a method for monitoring the efficacy of treatment of a tuberculosis infection, comprising:

(a) determining the presence or amount of BlaC protein, nucleic acid encoding BlaC protein, or anti-BlaC antibodies in a biological sample obtained from a subject receiving treatment for tuberculosis; and (b) comparing the amount of BlaC protein, nucleic acid encoding BlaC protein, or anti-BlaC antibodies in the biological sample as determined in step (a) to a reference standard, thereby determining the efficacy of treatment.

In some embodiments, the reference standard in step (b) is the amount of BlaC protein, nucleic acid encoding BlaC protein, or anti-BlaC antibodies determined in an analogous biological sample obtained from the subject at or after diagnosis with the tuberculosis infection but prior to the obtaining of the biological sample from the subject in step (a), whereby a lower amount of anti-BlaC antibodies in the biological sample determined in step (a) compared to the biological sample in step (b) is indicative of a positive response to the treatment.

In another aspect, the present disclosure provides an isolated polynucleic acid molecule comprising a detectable label, wherein the polynucleic acid molecule has a polynucleotide sequence set forth in a sequence selected from the group consisting of SEQ ID NOS:3-29, or homologs thereof.

In another aspect, the present disclosure provides a kit comprising in one or more containers DNA polymerase enzyme, deoxynucleoside triphosphates, buffer solution, and an isolated polynucleic acid molecule comprising a detectable label, as described herein. In some embodiments, the kit comprises a polynucleotide primer pair selected from the group consisting of SEQ ID NOS:12 and 21, SEQ ID NOS:13 and 22, SEQ ID NOS:14 and 23, SEQ ID NOS:15 and 24, SEQ ID NOS:16 and 25, SEQ ID NOS:17 and 26, SEQ ID NOS:18 and 27, SEQ ID NOS:19 and 28, and SEQ ID NOS:20 and 29, or homologs thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 5 illustrates an amino acid sequence alignment of BlaC protein from several TB-complex species. The BlaC protein in the TB-complex is highly conserved (100% identity). The three signature motifs are shown in green ("Motif I"), red ("Motif II") and blue ("Motif III"). The illustrated amino acid sequence for *M. tuberculosis* BlaC protein, and the identical consensus sequence for the BlaC protein of the indicated TB-complex bacteria, is set forth herein as SEQ ID NO:2.

FIG. 6 illustrates an amino acid sequence alignment of BlaC of *M. tuberculosis* with that of other pathogenic bacteria that are not part of the TB complex. The BlaC protein of *M. tuberculosis* displays low similarity to the other β-lactamases. Sequence identifiers for each amino acid sequence are indicated in the figure. The sequences for the three signature motifs (i.e., I, II, and III) of the *M. tuberculosis* BlaC sequence are indicated.

FIG. 7 illustrates a sequence alignment of the β-lactamase gene from various relevant pathogenic bacteria, including *M. tuberculosis*. The alignment demonstrates that the blaC gene of *M. tuberculosis* (set forth herein as SEQ ID NO:1) has low similarity with other β-lactamase genes.

DETAILED DESCRIPTION

Figure 1A:
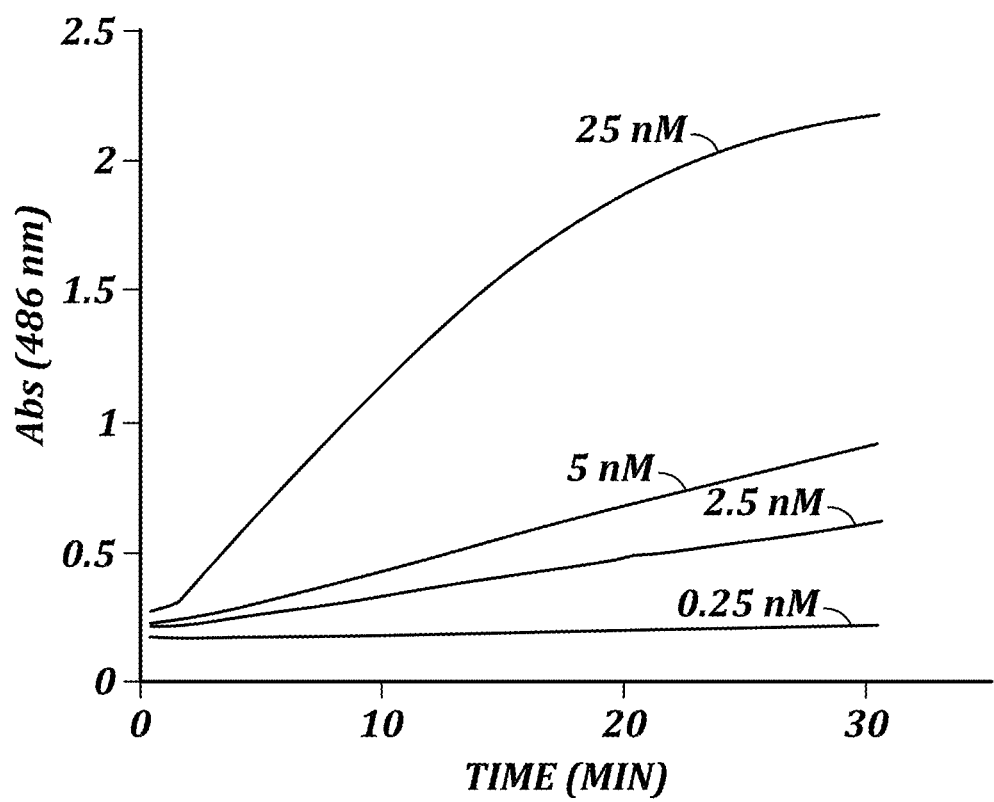
FIG. 1A graphically illustrates the hydrolysis of nitrocefin by BlaC over time. Hydrolyzed nitrocefin products demonstrate a maximum absorption at 485 nm. The formation of the hydrolyzed product was monitored by absorbance at 486 nm ($A_{486}$) as a function of time using difference concentrations of purified BlaC enzyme (concentrations indicated with arrows).

The present disclosure generally relates to the specific detection of tuberculosis-complex bacteria using β-lactamase as a biomarker. Specifically, the present disclosure relates to methods and compositions for the detection of specific β-lactamase protein and nucleic acid sequences to indicate the presence of tuberculosis-complex bacteria.

As used herein, the term "tuberculosis-complex bacteria" refers to bacteria from any species of a closely related group of *Mycobacterium* that can cause tuberculosis (TB). The tuberculosis complex, or TB-complex, can include bacteria from at least the following recognized species: *Mycobacterium tuberculosis* (Mtb), *Mycobacterium africanum*, *Mycobacterium bovis*, *Mycobacterium bovis Bacillus* Calmette Guerin (BCG), *Mycobacterium microti*, *Mycobacterium canettii*, *Mycobacterium pinnipedii*, and *Mycobacterium mungi*. These and other mycobacteria species are generally considered to be Gram-positive. However, because they lack the typical outer cell membrane, they do not retain the crystal violet Gram stain very well. Because they can be imaged with an acid-fast technique, they are often referred to as acid-fast Gram positive.

As used herein, the term "tuberculosis" ("TB") refers to the common, and often lethal, disease. TB is currently in the top-ten causes of death for humans worldwide. A TB infection is generally classified as being either latent or active. Latent TB occurs when the bacteria are present in the body, but in an inactive state. The inactivity might be the result of immune mechanisms that prevent bacterial growth and spreading. For example, scar tissue or fibrosis can form around the TB bacteria to isolate the bacteria and to prevent the infection from spreading. Latent infections typically present no symptoms and are not contagious. In contrast, active TB is contagious and is the condition that is associated with various symptoms. Active TB can affect almost any tissue or organ in the body, but the most common site of disease is in the lungs. With reference to lung infections, when the bacteria multiply, they can cause pneumonia along with chest pain, coughing up blood, and a prolonged cough. TB is infectious because TB-complex bacteria can be passed through the air in water droplets when subjects with active infections cough, sneeze, or otherwise eject fluids into the air. Additionally, lymph nodes near the heart and lungs often become enlarged during infection. The disease can progress, causing pneumonia and damage to kidneys, bones, and the meninges that line the spinal cord and brain. Classic symptoms of active TB infections include unexplained weight loss, tiredness, fatigue, shortness of breath, fever, night sweats, chills, and a loss of appetite. Symptoms specific to the lungs include coughing that lasts for 3 or more weeks, coughing up blood, chest pain, and pain with breathing or coughing. Various antibiotics are used to treat TB infections, depending on whether the infection is latent or active. Because treatments tend to require prolonged administration of antibiotics, many patients do not complete the entire course, which can lead to antibiotic resistance and disease management challenges.

As used herein, the term "β-lactamase" refers to an enzyme produced by various bacteria known to confer resistance to certain β-lactam antibiotics, such as penicillins, cephamycins, and some carbapenems. β-lactamases are known to be secreted, and in some gram-negative bacteria an increase in secreted levels occurs when antibiotics are in the environment. β-lactamases are classified based on the amino acid (and encoding nucleic acid) sequences of the enzymes. Currently, four classes (A-D) have been characterized. TB-complex bacteria naturally express β-lactamase (BlaC) that belongs to "class A" of the β-lactamase family.

The present disclosure is based, in part, on the discovery that unlike various other bacteria, the blaC gene is constitutively expressed at high levels by TB-complex bacteria under almost all growth conditions. The BlaC protein specifically localizes on the surface of the bacteria and is also constitutively secreted under various growth conditions. As described in more detail below, comparative analyses revealed numerous differences between the BlaC amino acid sequence, and their encoding nucleic acid blaC sequence, of TB-complex bacteria and the β-lactamase sequences from other, non-TB-complex bacteria (i.e., other bacteria, even including mycobacterial species that do not cause tuberculosis in humans or animals). Thus, reagents and methods that specifically detect BlaC protein or blaC nucleic acid sequences from the TB-complex bacteria have utility for the specific and sensitive detection and diagnosis of TB-complex bacteria.

Accordingly, in one aspect, the present disclosure provides an affinity reagent that specifically binds to a β-lactamase (BlaC) of a TB-complex bacterium.

As used herein, the term "specifically binds" refers to the ability of the affinity reagent to bind to the BlaC protein, without significant binding to other molecules, such as β-lactamase (Bla) protein of non-TB-complex bacteria, under standard conditions known in the art. The affinity reagent can bind to other peptides, polypeptides or proteins, but with lower affinity as determined by, e.g., immunoassays, BIAcore, or other assays known in the art. Affinity reagents preferably do not cross-react with other proteins, such as β-lactamase (Bla) protein of non-TB-complex bacteria. For example, the affinity reagent preferably binds to the BlaC protein in a manner that is detectable over background binding.

As used herein, the term "affinity reagent" refers to any molecule having an ability to bind to a specific molecule with a specific affinity (i.e., detectable over background). More specifically, in the context of the present disclosure, the term generally refers to a molecule having the ability to specifically bind to a β-lactamase (BlaC) of a TB-complex bacterium. The affinity reagent can be an antibody, an enzyme substrate, a modified enzyme substrate, and the like.

In some embodiments, the affinity reagent is an antibody. As used herein, the term "antibody" encompasses antibodies and antibody fragments thereof, derived from any antibody-producing mammal (e.g., mouse, rat, rabbit, and primate including human), that specifically bind to a polypeptide target of interest, such as BlaC, or portions thereof. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

An antibody fragment is a portion derived from or related to a full-length antibody, preferably including the antigen binding or variable region thereof. Illustrative examples of antibody fragments useful in the present disclosure include Fab, Fab', F(ab)$_2$, F(ab')$_2$ and Fv fragments, scFv fragments, diabodies, linear antibodies, single-chain antibody molecules, multispecific antibodies formed from antibody fragments, and the like. A "single-chain Fv" or "scFv" antibody fragment comprises the $V_H$ and $V_L$ domains of an antibody, wherein these domains are present in a single polypeptide chain. The Fv polypeptide can further comprise a polypeptide linker between the $V_H$ and $V_L$ domains, which enables the scFv to form the desired structure for antigen binding. Antibody fragments can be produced recombinantly, or through enzymatic digestion.

Antibodies can be further modified to suit various uses. For example, a "chimeric antibody" is a recombinant protein that contains the variable domains and complementarity-determining regions (CDRs) derived from a non-human species (e.g., rodent) antibody, while the remainder of the antibody molecule is derived from a human antibody. A "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions (CDRs) are of non-human origin.

Production of antibodies can be accomplished using any technique commonly known in the art. For example, the production of a polyclonal antibody described herein can be generated by administering an immunogen containing the target antigen, such as BlaC or a fragment thereof, to an antibody-producing animal. For example, the target antigen can be administered to a mammal (e.g., a rat, a mouse, a rabbit, a chicken, cattle, a monkey, a pig, a horse, a sheep, a goat, a dog, a cat, a guinea pig, a hamster) or a bird (e.g., a chicken) so as to induce production of a serum containing an antigen-specific polyclonal antibody. The target antigen can be administered in combination with other components known to facilitate induction of a B-cell response, such as any appropriate adjuvant known in the art. For example, as described below in more detail below, recombinant BlaC was administered to rabbits to obtain a population of polyclonal antibodies that were demonstrated as useful reagents in the detection of BlaC (and TB-bacteria expressing BlaC) in sputum. Furthermore, the polyclonal antibody reagent can be further processed to remove any antibody members that have unacceptable affinity for non-BlaC antigen. For example, to ensure specificity of a polyclonal antibody reagent for BlaC over any particular β-lactamase protein(s) from non-TB complex bacteria, the polyclonal antibody can be contacted to immobilized β-lactamase protein(s) under conditions that permit binding. In this way, antibodies from the polyclonal reagent that bind can be removed from the reagent when the unbound antibodies are collected. The resulting polyclonal antibody reagent will exhibit enhanced specificity for BlaC and are useful for detection of BlaC and/or TB-complex bacteria. Many approaches for adsorption of polyclonal antibody reagents to reduce cross-reactivity exist, are familiar to persons of ordinary skill in the art, and are encompassed by the present disclosure.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art. An illustrative strategy for producing monoclonal antibodies is described below.

Antibody fragments that recognize specific epitopes can be generated by any technique known to those of skill in the art. For example, Fab and $F(ab')_2$ fragments of the invention can be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CHI domain of the heavy chain. Further, the antibodies of the present invention can also be generated using various phage display methods known in the art.

In some embodiments, the BlaC protein comprises at least 5, 6, 7, 8, 9, 10, 11, 12, 13, 14, 15, 16, 17, 18, 19, 20, 21, 22, 23, 24, 25, or more consecutive amino acid residues with a sequence that is at least 95%, 96%, 97%, 98%, or 99% identical to a sequence fragment of the amino acid sequence set forth in SEQ ID NO:2. In some embodiments, the BlaC protein has an amino acid sequence that is at least 95%, 96%, 97%, 98%, or 99% identical to the amino acid sequence set forth in SEQ ID NO:2. As used herein, the terms indicating "percent identity" or "percent identical" refer to the percentage of amino acid residues in a polypeptide sequence that are identical with the nucleic acid sequence or amino acid sequence of a specified molecule, after aligning the sequences to achieve the maximum percent identity. For example, the Vector NTI Advance™ 9.0 may be used for sequence alignment. An exemplary BlaC is provided in the GenBank database under accession number WP_003410677.1. In some embodiments, the BlaC protein comprises an amino acid sequence set forth in SEQ ID NO:2, or a fragment thereof with at least 5, 6, 7, 8, 9, 10, 11, 12, 13, 14, 15, 16, 17, 18, 19, 20, 21, 22, 23, 24, 25 or more amino acids. In some embodiments, the fragment comprises amino acids corresponding to amino acids within positions 75-87 of SEQ ID NO:2, within amino acids at positions 142 to 144 of SEQ ID NO:2, and/or within amino acids at positions 249 to 252 of SEQ ID NO:2. Such regions are known to participate in structural motifs that are important for enzymatic activity (see FIG. 5).

In some embodiments, the affinity reagent is capable of specifically binding to the BlaC protein or any antigenic fragment or portion thereof. Antigenic fragments can be predicted using known methods.

In some embodiments, the affinity reagent is detectably labeled to facilitate detection of complex formation between the target BlaC protein, or a fragment thereof, and the affinity reagent. The detectable labels are described in more detail below.

The affinity reagents described above are useful for the specific capture and/or detection of BlaC protein to indicate the presence of TB-complex bacteria. Accordingly, in one aspect, the present disclosure provides a method of detecting the presence of tuberculosis-complex bacteria in a sample, comprising contacting the sample with an affinity reagent described herein. As described, the affinity reagent specifically binds to a BlaC protein of a TB-complex bacterium, or a fragment thereof. The method further comprises detecting the formation of a complex between the BlaC protein and the affinity reagent, wherein the formation of a complex is indicative of the presence of tuberculosis complex bacteria in the sample.

According to this aspect, the detection of a complex between the BlaC protein and the affinity reagent can be performed according to any known assay format for this purpose. Such assays for the detection and/or quantification of the BlaC protein typically involve incubation of the sample that potentially contains the target BlaC protein with the affinity reagent, and detection via the formation of a complex between the affinity reagent and the target BlaC protein. In various embodiments, either the components of the biological sample (including the target BlaC protein) or the affinity reagents are immobilized. In some embodiments, either the affinity reagent or some component of target BlaC protein is modified in a manner that it provides a detectable signal. Exemplary techniques include immunoassays, such as in situ hybridization, western blots, immunoprecipitation followed by SDS-PAGE electrophoresis, immunocytochemistry, ELISA, and the like, some of which are described in more detail below.

Immunoassays encompassed by the present disclosure can be organized in a number of different formats recognized in the art. For example, in competitive immunoassays, unlabeled analyte from a biological sample competes with a labeled version of the analyte, such as BlaC protein, for binding to an affinity reagent. The amount of labeled, unbound analyte is then measured. The more unlabeled analyte in the biological sample results in more labeled analyte that is displaced or competed off of the affinity reagent. Thus, the amount of labeled, unbound analyte that can be rinsed away is proportional to the amount of unlabeled analyte present in the biological sample. In a variation of this embodiment, the amount of labeled, bound analyte is measured, which is inversely proportional to the amount of unlabeled analyte present in the biological sample. In some embodiments, the affinity reagent is immobilized to facilitate the rinsing of the reagent, without losing the bound analytes.

Some formats are non-competitive. In one example, in situ hybridization utilizes a combination of immunofluorescence and microscopy techniques. A labeled affinity reagent can be employed on a biological or histological sample obtained from a subject. The affinity reagent is preferably applied by overlaying the labeled affinity reagent onto the biological sample and allowing the affinity reagent to contact any target BlaC protein that may be present. The sample is visualized under the appropriate microscopy conditions to visualize the affinity reagent through its detectable label. Through this technique, it is possible to determine not only the presence of the BlaC protein, but also its distribution within the sample. A wide variety of well-known histological methods can be utilized in order to achieve such in situ detection.

In another exemplary non-competitive immunoassay, the biological sample can be brought in contact with, and immobilized onto, a solid phase support or a carrier, such as nitrocellulose, a plastic well, beads, magnetic particles, and the like. The solid phase support or carrier is capable of immobilizing cells, cell particles or soluble proteins. The solid phase support or carrier can then be washed with suitable buffers followed by treatment with the detectably labeled affinity reagent. The solid phase support or carrier can then be washed with the buffer a second time to remove unbound affinity reagent. The amount of bound label on solid phase support or carrier can then be detected by conventional means and is directly proportional to the amount of the target analyte, such as BlaC protein.

The term "solid phase support or carrier" is intended to mean any support or carrier capable of binding a cell or protein such as BlaC, or an affinity reagent. Well-known supports or carriers include glass, polystyrene, polypropylene, polyethylene, dextran, nylon, amylases, natural and modified celluloses, polyacrylamides, gabbros, and magnetite. A substrate that acts as a carrier can be either soluble to some extent or insoluble for the purposes of the present invention. The support or carrier material can have virtually any possible structural configuration to conform to any assay format so long as the coupled target or affinity reagent is capable of binding to the corresponding affinity reagent or target molecule, respectively. Thus, the support or carrier configuration can be substantially spherical, as in a bead or magnetic particle, or cylindrical, as in the inside surface of a test tube, or well in a multi-well plate. Alternatively, the surface can be flat such as a sheet, test strip, etc., that would be appropriate in a lateral flow assay format. Those skilled in the art will recognize that many other suitable carriers are available for binding affinity reagents or the target BlaC protein (or cells displaying the BlaC protein), or will be able to ascertain the same by use of routine experimentation.

In some embodiments, the target protein/cell or affinity reagent is immobilized directly to the solid phase support or carrier according to standard protocols in the art. In other embodiments, the target protein/cell or affinity reagent is indirectly immobilized on the solid phase support or carrier. For example, as described in more detail below, antibodies can be "captured" and immobilized by protein A/G that is bound to the solid support. Sometime it is preferable to utilize known blocking reagents to prevent spurious or elevated background binding.

For example, an illustrative format for the detection of BlaC in sputum is provided in the Snap Valve™ (Medical Packaging Corporation, CA, USA) that incorporates a flocked swab in a lateral flow device. The device can contain a matrix that can allow migration of the biological sample, including the target BlaC, past a region with immobilized affinity reagent. Detection of binding can be visualized as a result of any of the assay formats described herein, such as sandwich assays, competitive assays, and the like.

In some embodiments, the target protein/cell or affinity reagent is conjugated onto a particle, such as a bead or magnetic particle, to facilitate collection or immobilization for further analysis.

Another exemplary non-competitive immunoassay format is referred to as a "sandwich" assay. In a sandwich assay, one affinity reagent is typically immobilized on a solid support or carrier. The biological sample is captured by the immobilized affinity reagent (thus, also referred to as the "capture reagent"). A second affinity reagent (also referred to as the "detection reagent") that is detectably labeled is also added. The capture affinity reagent can be the same as the detection affinity reagent. For example, as described below, the same polyclonal antibody population can be used for both the immobilization/capture and for the labeled detection of the target BlaC protein. In other embodiments, the capture affinity reagent can be different from the detection affinity reagent.

As used herein, the term "labeled" can refer to direct labeling of the affinity reagent or target BlaC protein via, e.g., coupling a detectable substance to the affinity reagent or target protein. The term can also refer to indirect labeling of the affinity reagent by reactivity with another affinity reagent that is directly labeled. For example, an antibody affinity reagent specific for BlaC protein can itself be specifically bound by a second antibody that is detectably labeled.

In some embodiments, the detectable label comprises the coupling of an enzyme that is capable of producing a detectable signal when it acts upon a specific substrate. Some embodiments of enzyme-based immunoassays are referred to as enzyme linked immunosorbent assays (ELISAs) and are well-known in the art. See e.g., Voller, A., "The Enzyme Linked Immunosorbent Assay (ELISA)," 1978, *Diagnostic Horizons* 2:1-7, Microbiological Associates Quarterly Publication, Walkersville, Md.; Voller, A. et al., 1978, *J. Clin. Pathol.* 31:507-520; Butler, J. E., 1981, *Meth. Enzymol.* 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The substrates for these illustrative enzymes are commonly known in the art. The detection can be accomplished by colorimetric methods which employ a chromogenic substrate for the enzyme. Detection can also be accomplished by visual comparison of the extent of enzymatic reaction of a substrate in comparison with similarly prepared standards.

An exemplary protocol for a sandwich ELISA format in a multi-well plate is as follows: 1) coat plate with anti-BlaC capture antibody; 2) block (and optionally preserve and dry) the coated plate; 3) add biological sample in buffer to the plate and incubate for approximately 30 minutes; 4) wash; 5) add anti-BlaC-HRP affinity reagent to plate; 6) wash; 7) add HRP substrate to plate and incubate for approximately 15 minutes; and 8) add stop solution and read signal to determine amount of bound target BlaC on the plate. It will be readily recognized that various alterations to the above protocol can be made. One variation in the assay format includes pre-incubating the detection affinity reagent and biological sample before adding to the plate. Other variations are known and commercially available. For instance, one illustrative assay format is the Simoa™ assay (Quanterix, MA, USA), which incorporates the ELISA approach on a nanoscale using affinity reagents attached to paramagnetic particles. The particles are then loaded individually into femtoliter-scale wells and read for signal.

In other embodiments, the target protein or affinity reagent can be directly coupled to detectable moieties. For example, in a radioimmunoassay (RIA) the target protein or affinity reagent can be radioactively labeled, allowing detection of the target protein through any of the described formats. The radioactive isotope (e.g., 125I, 131I, 35S or 3H) can be detected by such means as the use of a gamma counter or a scintillation counter or by autoradiography.

In other embodiments, the target BlaC protein or affinity reagent is coupled to a fluorescent compound. When the fluorescently labeled antibody is exposed to light of the proper wavelength, its presence can then be detected due to fluorescence. A non-limiting, illustrative list of fluorescent compounds includes fluorescein isothiocyanate, rhodamine, phycoerythrin, phycocyanin, allophycocyanin, o-phthaldehyde and fluorescamine.

In other embodiments, the target BlaC protein or affinity reagent is coupled to a fluorescence emitting metal such as 152Eu, or others of the lanthanide series. These metals can be attached to the antibody using such metal chelating groups as diethylenetriaminepentacetic acid (DTPA) or ethylenediaminetetraacetic acid (EDTA).

In other embodiments, the target BlaC protein or affinity reagent is conjugated to a chemiluminescent compound. The presence of the chemiluminescent-tagged target BlaC protein or affinity reagent is then determined by detecting the presence of luminescence that arises during the course of a chemical reaction. Illustrative, non-limiting examples of particularly useful chemiluminescent labeling compounds are luminol, isoluminol, theromatic acridinium ester, imidazole, acridinium salt and oxalate ester.

In other embodiments, the target BlaC protein or affinity reagent is conjugated to a bioluminescent compound. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. The protein can also be detected by monitoring its catalytic activity (such as in ELISA), if the protein is an enzyme. The protein can also be detected using coupled enzymatic assays.

In other embodiments, the affinity reagent contains a fluorescent protein domain. Such fluorescent protein domains are known in the art, and include GFP, dtTomato, and mCherry. The affinity reagent with a fluorescent protein domain can be produced according to any commonly known techniques, such as the recombinant expression of a fusion protein that includes the fluorescent domain.

According to this aspect of the disclosure, the presence of BlaC in the biological sample, as determined according to any recognized method including those described above, is indicative of a TB-complex bacterium in the sample. As used herein, the term "sample" refers to any sample that can harbor bacteria or bacterial secretions, and can include fluids, pharmaceutical compositions, or consumable products, which could potentially be contaminated with mycobacteria. In some embodiments, the sample is a biological sample, such as comprising nutrients and/or media sufficient to support sustenance or growth of living mycobacteria. In some embodiments, the biological sample is a tissue culture sample.

In a further aspect of the disclosure, the sample is a biological sample obtained from a subject. According to this aspect, the presence of BlaC in the biological sample obtained from a subject, as determined according to any recognized method including those described above, is indicative of a tuberculosis infection in the subject.

As used herein, the term "subject" refers to any animal that can harbor a tuberculosis infection by any of the described bacteria in the TB-complex. In some embodiments, the subject is a vertebrate animal. In some embodiments, the subject is a mammal. In some embodiments the subject is a human.

Suitable biological samples include sputum, pleural fluid, spinal fluid, blood, urine, saliva, stool/feces, mucus, tissue biopsies, tissue homogenates, directly in live animals or human patients, or a sample obtained by swabbing an area of interest on a subject. For example, illustrative examples of BlaC and/or bacteria expressing BlaC detection using the disclosed reagents were performed in sputum and saliva samples, as described in more detail below.

In another aspect, the disclosure provides a method for detecting the presence or amount of anti-β-lactamase (BlaC) antibody in a biological sample obtained from a subject. A determined presence of anti-β-lactamase (BlaC) antibody in the sample is indicative of the presence of BlaC in the subject, and hence, is indicative of a TB-complex bacterial infection in the subject. In some embodiments, such an assay can incorporate the use of the antigen/epitope unique to BlaC over somewhat similar β-lactamase antigens. For example, as well-understood in the art, such BlaC antigen/epitopes can be immobilized to a solid substrate whereby the antigen/epitopes are contacted with the biological sample. Binding of any antibody from the sample can be detected, for example, using a labeled antibody specific for antibodies from the subject.

It will be recognized that the subject's antibody can form a complex with antigenic fragments of the BlaC protein. Antigenic portions will typically comprise at least six amino acids of the BlaC protein. Specifically, the antigenic portions typically comprise the amino acids that are exposed to the exterior environment of the expressed protein, such that they are accessible to the B-cells of the subject's immune system. Accordingly, in some embodiments, the method comprises (a) contacting the biological sample with at least one polypeptide with an amino acid sequence that has at least 90% sequence identity to any six or more amino acids of SEQ ID NO:2; and (b) detecting the formation of a complex between the antibody in the sample and the polypeptide. In some embodiments, the at least one polypeptide has an amino acid sequence with at least 90% sequence identity to at least six to 20, or more amino acids of SEQ ID NO:2. In further embodiments, the amino acids are contiguous. It will also be appreciated that the polypeptide will preferably have a unique sequence, or a low sequence identity to other bacterial β-lactamases, so as to avoid forming a complex under the standard conditions. In some embodiments, the polypeptide, or fragment thereof, comprises amino acids corresponding to amino acids within positions 75 to 87 of SEQ ID NO:2, within amino acids at positions 142 to 144 of SEQ ID NO:2, and/or within amino acids at positions 249 to 252 of SEQ ID NO:2. Such regions are known to participate in structural motifs that are important for the unique enzymatic activity of BlaC (see FIG. 5).

Detection of a complex between the antibody and the polypeptide can be accomplished with any method known in the art for this purpose, including those described herein above. For example, antibodies in the biological sample can be immobilized on a substrate and BlaC (or BlaC fragment) with a detectable label attached thereto can be added. Conversely, the BlaC (or BlaC fragment) can be immobilized on the substrate and the biological sample contacted thereto. A detection affinity reagent specific for human antibodies can be applied after a wash cycle. The retention of a detectable signal after a wash cycle is indicative that the subject has produced an anti-β-lactamase antibody.

In some embodiments, the method further comprises comparing a determined amount of anti-BlaC antibody (by virtue of detectable signal intensity) to a reference standard to establish the level of binding with respect to background signal. An amount of anti-BlaC antibody detected in the biological sample greater than the reference standard is indicative of the presence or relative amount of tuberculosis-complex bacteria in the subject. It is preferred that the reference standard is a biological sample-type that is the same as the biological sample obtained from the subject.

In another aspect, the present disclosure provides an assay kit comprising the affinity reagent described herein. In some embodiments, the assay kit also includes buffers and requisite reagents as described herein to analyze a biological sample for the presence of BlaC. In some embodiments, the kit includes a device that provides a solid support. In some embodiments, the kit can comprise a lateral flow device. In some embodiments, the kit can comprise an ELISA format plate.

As described herein, the blaC gene encoding the β-lactamase in the TB-complex bacteria of *M. tuberculosis* has unique domains that are dissimilar to the homologous bla genes encoding β-lactamase in other pathogenic bacteria, including non TB-complex bacteria in the genus Mycobacteria. Accordingly, in another aspect, the present disclosure provides a method for presence of TB-complex bacteria in a test sample by virtue of the detection of the unique, TB-complex specific β-lactamase sequence at the nucleic acid level.

In one embodiment, the method comprises contacting the sample with a polynucleotide probe capable of specifically hybridizing to a target region of a nucleic acid molecule that encodes a β-lactamase (BlaC) with an amino acid sequence set forth in SEQ ID NO:2. The method further comprises detecting the hybridization of the probe to the nucleic acid molecule encoding BlaC, wherein detected hybridization is indicative of the presence of tuberculosis complex bacteria in the test sample. In some embodiments, the probe comprises a detectable label.

As used herein, the terms "nucleic acid, polynucleic acid, or polynucleotide" refer to a deoxyribonucleotide polymer (i.e., DNA) or ribonucleotide polymer (i.e., RNA) in either single- or double-stranded form. Unless otherwise limited, encompasses known analogs of natural nucleotides that hybridize to nucleic acids in a manner similar to naturally occurring nucleotides, such as peptide nucleic acids (PNAs) and phosphorothioate DNA. Unless otherwise indicated, a particular nucleic acid sequence includes the complementary sequence thereof. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolo-pyrimidine triphosphate, and 2-thiocytidine, as well as the alphathiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

As used herein, the term "polynucleotide probe" refers to a nucleic acid with a plurality of nucleotide subunits in a contiguous polymer chain. The term "capable of specifically hybridizing" with respect to the polynucleotide probe refers to the ability of the polynucleotide probe, by virtue of its nucleotide sequence, to form and maintain non-covalent bonds between the nucleotides of opposing polymer strands. For example, in DNA the pyrimidines base structures thymine (T) and cytosine (C) typically pair with the purine base structures adenine (A) and guanine (G), respectively. It is recognized that some mismatch in sequence between the probe and the template polynucleic probe is permitted. However, the sequences must be sufficiently complementary to permit hybridization ("annealing") under standard conditions. Standard hybridization conditions are known in the art. Thus, the term "specifically hybridize" as used herein refers to the ability of a nucleic acid to hybridize detectably and specifically to a second nucleic acid. Polynucleotides specifically hybridize with target nucleic acid strands under standard hybridization and wash conditions that minimize appreciable amounts of detectable binding to non-specific nucleic acids (i.e., without corresponding sequence similarity). In this aspect, the probe specifically hybridizes to a target region of a nucleic acid molecule that encodes a β-lactamase (BlaC) with an amino acid sequence set forth in SEQ ID NO:2. Skilled artisans knowing the redundancy of the genetic code will understand the scope of nucleic acids (e.g., DNA and RNA molecules) that can encode the amino acid sequence in SEQ ID NO:2. In one embodiment, the nucleic acid molecule that encodes a β-lactamase (BlaC) is set forth in SEQ ID NO:1.

In some embodiments, the target region is at least 10 contiguous nucleotides of the encoding nucleic acid.

It will be appreciated that the sequence of the target region will have low sequence identity with any nucleic acid sequence appearing in non-TB-complex bacteria. As used herein with respect to nucleic acid molecules, the term "sequence identity" or "percent identical" is the percentage of nucleic acid residues in a candidate nucleic acid molecule sequence that are identical with a subject nucleic acid molecule sequence (such as the nucleic acid molecule sequence set forth in SEQ ID NO:2), after aligning the sequences to achieve the maximum percent identity, and not considering any nucleic acid residue substitutions as part of the sequence identity. No gaps are introduced into the candidate nucleic acid sequence in order to achieve the best alignment. Nucleic acid sequence identity can be determined in the following manner. The subject polynucleotide molecule sequence is used to search a nucleic acid sequence database, such as the Genbank database, using the program BLASTN version 2.1 (based on Altschul et al., *Nucleic Acids Research* 25:3389-3402 (1997)). The program is used in the ungapped mode. Default filtering is used to remove sequence homologies due to regions of low complexity as defined in Wootton, J. C., and S. Federhen, *Methods in Enzymology* 266:554-571 (1996). The default parameters of BLASTN are utilized. It will be appreciated that "low sequence identity" will result in a failure of the probe to hybridize under standard conditions with the non-target region of the nucleic acid from non-TB-complex sources.

In some embodiments, the polynucleotide probe comprises a polynucleotide sequence selected from the group consisting of SEQ ID NO:3, 4, 5, 6, 7, 8, 9, 10, and 11. In some embodiments, the polynucleotide probe encompasses homologs of the polynucleotides selected from the group consisting of SEQ ID NO:3, 4, 5, 6, 7, 8, 9, 10, and 11. As used herein, the term "homologs" refers to nucleic acids having one or more alterations in the primary sequence set forth in any one of SEQ ID NO:3, 4, 5, 6, 7, 8, 9, 10, and 11, that does not destroy the ability of the polynucleotide to specifically hybridize with a target sequence, as described above. A primary sequence can be altered, for example, by the insertion, addition, deletion or substitution of one or more of the nucleotides. Thus, in some embodiments, the polynucleotide probe comprises a polynucleotide sequence that is at least about 90%, 95%, or 99% identical to a sequence selected from the group consisting of SEQ ID NO:3, 4, 5, 6, 7, 8, 9, 10, and 11.

Detection of hybridization of the probe to the nucleic acid molecule encoding BlaC can be accomplished through any commonly known technique. For example, the probe may be configured to emit a detectable signal only upon specific binding to the nucleic acid target sequence. In one illustrative probe configuration, known as a molecular beacon probe, the probe maintains a hairpin/loop shape. The internal loop domain comprises the sequence that is complementary to the target nucleic acid sequence. The stem of the hairpin structure is formed by complementary oligonucleotide sequences that are at the 5' and 3' end of the linear probe sequence. A fluorophore is covalently attached to the end of one of the stem oligonucleotide sequences, whereas a quencher dye is covalently attached to the end of the other stem oligonucleotide. When in the intact hairpin configuration, the probe does not emit a detectable signal because of the close proximity of the quencher and fluorophore. However, when annealing to the target sequence, the probe linearizes permitting a sufficient distance to form between the fluorophore and quencher dyes, thus allowing a detectable signal. Such a probe can be incorporated into extension or amplification-based assays, such as PCR-based amplification assays, as described in more detail below.

In another embodiment of this aspect, the disclosure provides a method for determining the presence of tuberculosis-complex bacteria in a test sample, which generally comprises the following steps: (a) contacting the test sample with a composition comprising at least one primer pair comprising a forward and reverse primer capable of specifically hybridizing to a target region of tuberculosis-complex blaC gene, to form a reaction mixture; (b) subjecting said reaction mixture to amplification conditions suitable to amplify at least a portion of the target region; and (c) detecting amplification of the at least a portion of the target region, wherein amplification of the at least a portion of the target region is indicative of the presence of tuberculosis-complex bacteria in a test sample.

As used herein, the term "primer" means a polynucleotide which can serve to initiate a nucleic acid chain extension reaction. Typically, primers have a length of 5 to about 50 nucleotides, although primers can be longer than 50 nucleotides. Accordingly, in some embodiments, additional conditions and reagents are provided to facilitate the extension reaction using the probe as a primer. In some embodiments, the probe is one of a primer pair, such as used in the polymerase chain reaction. When employed as part of a primer pair, the probe can facilitate successive rounds of extension of the nucleic acid molecule sequence. Each successive round produced an increase of template nucleic acid template, thus leading to the amplification of the sequence. In such embodiments, a detectable label can include moieties or chemicals that are not linked to the probe. For example, dyes such as ethidium bromide or SYBR green intercalate in double stranded DNA and can serve as an indicator of successful amplification.

It will be appreciated that certain selection criteria are preferably employed when selecting primers (and optional probes). For example, for primer pairs for use in the amplification reactions, the primers are selected such that the likelihood of forming 3' duplexes is minimized, and such that the melting temperatures (Tm) are sufficiently similar to optimize annealing to the target sequence and minimize the amount of non-specific annealing. In this context, the polynucleotides according to the present invention are provided in combinations that can be used as primers in amplification reactions to specifically amplify target nucleic acid sequences. Furthermore, it will be appreciated that to specifically hybridize with the target region of the nucleic acid molecule, the sequence identity with other non-TB-complex bla gene sequences will be low.

In some embodiments, the forward primer has a polynucleotide sequence selected from the group consisting of SEQ ID NO:12, 13, 14, 15, 16, 17, 18, 19, 20, and any homologue thereof. Thus, in some embodiments, the polynucleotide probe comprises a polynucleotide sequence that is at least 90% identical to a sequence selected from the group consisting of SEQ ID NO:12, 13, 14, 15, 16, 17, 18, 19, and 20.

In some embodiments, the reverse primer has a polynucleotide sequence selected from the group consisting of SEQ ID NO:21, 22, 23, 24, 25, 26, 27, 28, 29, and any homologue thereof. Thus, in some embodiments, the polynucleotide probe comprises a polynucleotide sequence that is at least 90% identical to a sequence selected from the group consisting of SEQ ID NO:21, 22, 23, 24, 25, 26, 27, 28, and 29.

In some embodiments, the primer pair has sequences selected from the group consisting of SEQ ID NOS:12 and 21 (or homologs thereof), SEQ ID NOS:13 and 22 (or homologs thereof), SEQ ID NOS:14 and 23 (or homologs thereof), SEQ ID NOS:15 and 24 (or homologs thereof), SEQ ID NOS:16 and 25 (or homologs thereof), SEQ ID NOS:17 and 26 (or homologs thereof), SEQ ID NOS:18 and 27 (or homologs thereof), SEQ ID NOS:19 and 28 (or homologs thereof), and SEQ ID NOS:20 and 29 (or homologs thereof).

Extension and amplification procedures are well-known in the art and include, but are not limited to, polymerase chain reaction (PCR), TMA, rolling circle amplification, nucleic acid sequence based amplification (NASBA), and strand displacement amplification (SDA). One skilled in the art will understand that for use in certain amplification techniques the primers may need to be modified, for example, for SDA the primer comprises additional nucleotides near its 5' end that constitute a recognition site for a restriction endonuclease. Similarly, for NASBA the primer comprises additional nucleotides near the 5' end that constitute an RNA polymerase promoter. Polynucleotides thus modified are considered to be within the scope of the present invention.

Nucleic acid amplification reagents include reagents, which are well known and may include, but are not limited to, an enzyme having at least polymerase activity, enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

Amplification conditions are conditions that generally promote annealing and extension of one or more target nucleic acid sequences. It is well known that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures that are about 10° C. (e.g., 2° C. to 18° C.) below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Specific amplicons produced by amplification of target nucleic acid sequences using the polynucleotides of the present invention, as described above, can be detected by a variety of methods known in the art. For example, one or more of the primers used in the amplification reactions may be labeled such that an amplicon can be directly detected by conventional techniques during or subsequent to the amplification reaction. In another embodiment, total amplified product can be ascertained by inclusion of specific dyes, such as SYBR green, or an antibody that specifically detects the amplified nucleic acid sequence. In yet another embodiment, a third polynucleotide distinct from the primer sequences that has been labeled and is complementary to a region of the amplified sequence, can be added during or after the amplification reaction is complete. This third polynucleotide can be the probe as described above.

As indicated, the amplification products produced as described above can be detected during or subsequently to the amplification of the target sequence. Methods for detecting the amplification of a target sequence during amplification are outlined above, and described, for example, in U.S. Pat. No. 5,210,015. Gel electrophoresis can be employed to detect the products of an amplification reaction after its completion. Alternatively, amplification products are hybridized to probes, then separated from other reaction components and detected using microparticles and labeled probes. However, it will be readily appreciated both amplification and detection of target nucleic acid sequences can also take place concurrently in a single unopened reaction vessel. This type of procedure allows "real-time" monitoring of the amplification reaction, "end-point" monitoring, and can avoid contamination by reducing the handling steps.

For embodiments in which both amplification with polynucleotide primers and distinct detection probes are included concurrently during the amplification reaction, the polynucleotide probe preferably possesses certain properties. For example, since the probe will be present during the amplification reaction, it should not interfere with the progress of this reaction and should also be stable under the reaction conditions. In addition, for real-time monitoring of reactions, the probe should be capable of binding its target sequence under the conditions of the amplification reaction and to emit a signal only upon binding this target sequence. Examples of probe molecules that are particularly well-suited to this type of procedure include molecular beacon probes and probes comprising a fluorophore covalently attached to the 5' end of the probe and a quencher at the 3' end (e.g., TaqMan® probes).

Figure 12:
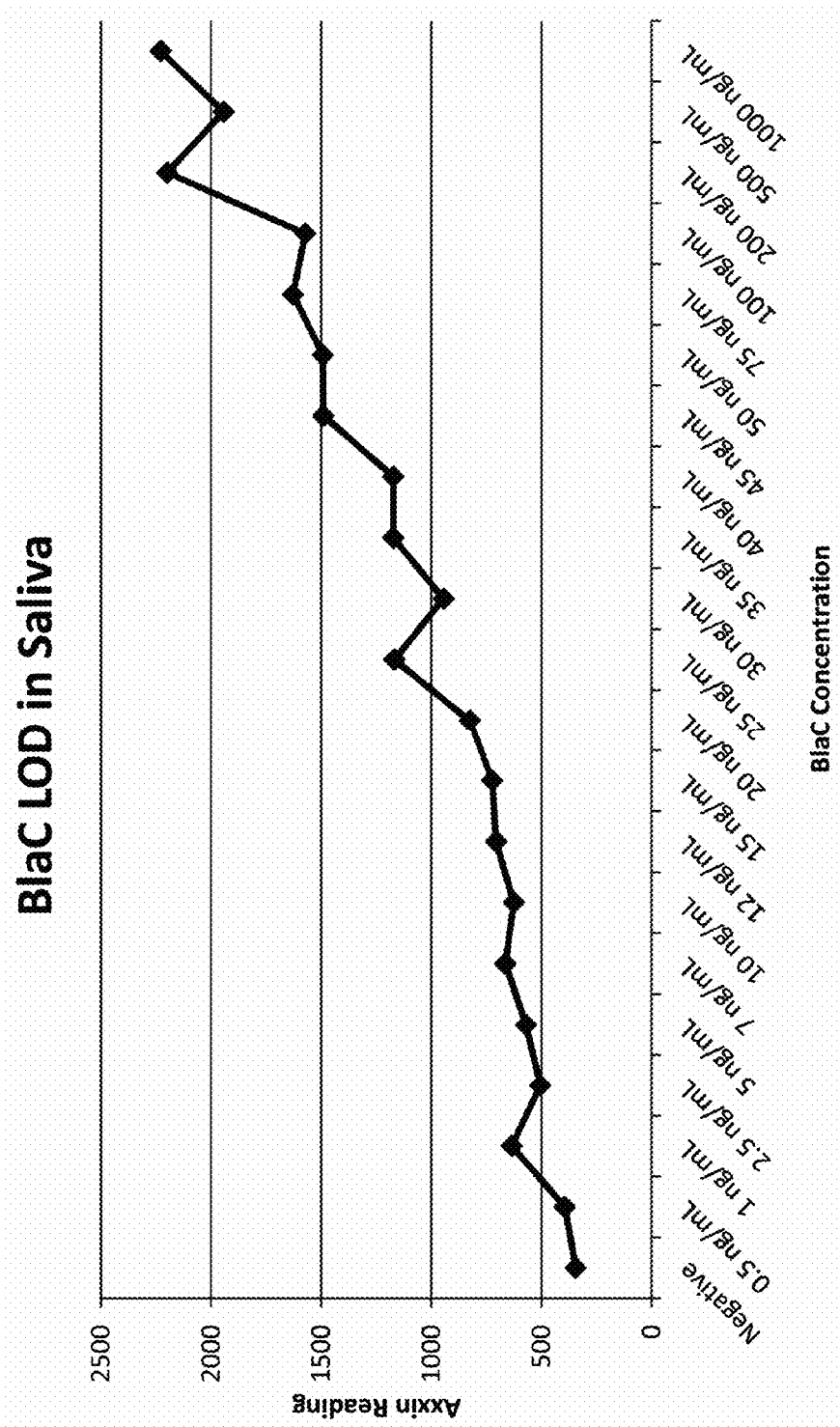
FIG. 12 graphically illustrates the Axxin readings of BlaC present in saliva sample.

The present invention, therefore, contemplates the use of the polynucleotides as TaqMan® probes as demonstrated below and illustrated in FIG. 12. As is known in the art, TaqMan® probes are dual-labeled fluorogenic nucleic acid probes composed of a polynucleotide complementary to the target sequence that is labeled at the 5' terminus with a fluorophore and at the 3' terminus with a quencher. TaqMan® probes are typically used as real-time probes in amplification reactions. In the free probe, the close proximity of the fluorophore and the quencher ensures that the fluorophore is internally quenched. During the extension phase of the amplification reaction, the probe is cleaved by the 5' nuclease activity of the polymerase and the fluorophore is released. The released fluorophore can then fluoresce and thus produces a detectable signal.

The term "detectable label" as used herein with reference to polynucleic acids refers to a molecule or moiety having a property or characteristic which is capable of detection and, optionally, of quantitation. Similar to labels described above in the context of detectably labeled proteins, a label can be directly detectable, as with, for example (and without limitation), radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate." A conjugate is typically a specific binding member that has been attached or coupled to a directly detectable label. Methods of labeling nucleic acid sequences are well known in the art (see, for example, Ausubel et al. (1997 & updates), *Current Protocols in Molecular Biology*, Wiley & Sons, New York). For example, coupling chemistries for synthesizing a conjugate are well known in the art and can include, for example, any chemical means and/or physical means that does not destroy the specific binding property of the specific binding member or the detectable property of the label.

Suitable fluorophores quenchers for use with various embodiments of polynucleotides of the present invention can be readily determined by one skilled in the art (see also Tyagi et al., *Nature Biotechnol.*, 16:49-53 (1998); Marras et al., *Genet. Anal. Biomolec. Eng.*, 14:151-156 (1999)). Many fluorophores and quenchers are available commercially, for example from Molecular Probes (Eugene, Oreg.) or Biosearch Technologies, Inc. (Novato, Calif.). Examples of fluorophores that can be used in the present invention include, but are not limited to, fluorescein and fluorescein derivatives such as carboxy fluorescein (FAM®), a dihalo-(C1 to C8)dialkoxycarboxyfluorescein, 5-(2'-aminoethyl) aminonaphthalene-1-sulphonic acid (EDANS), coumarin and coumarin derivatives, *Lucifer* yellow, Texas red, tetramethylrhodamine, tetrachloro-6-carboxyfluoroscein, 5-carboxyrhodamine, cyanine dyes and the like. Quenchers include, but are not limited to, DABCYL, 4'-(4-dimethylaminophenylazo)benzoic acid (DABSYL), 4-dimethylaminophenylazophenyl-4-dimethylaminophenylazophenyl-4'-maleimide (DABMI), tetramethylrhodamine, carboxytetramethylrhodamine (TAMRA), dihydrocyclopyrroloindole tripeptide minor groover binder (MGB®) dyes and the like.

In some embodiments that combine the use of primers and probes, the primer pair/probe combination has sequences selected from the group consisting of SEQ ID NOS:3, 12, and 21 (or homologs thereof), SEQ ID NOS:4, 13, and 22 (or homologs thereof), SEQ ID NOS:5, 14, and 23 (or homologs thereof), SEQ ID NOS:6, 15, and 24 (or homologs thereof), SEQ ID NOS:7, 16, and 25 (or homologs thereof), SEQ ID NOS:8, 17, and 26 (or homologs thereof), SEQ ID NOS:9, 18, and 27 (or homologs thereof), SEQ ID NOS:10, 19, and 28 (or homologs thereof), and SEQ ID NOS:11, 20, and 29 (or homologs thereof). Such combinations of primer pair/probes are set forth below in Tables 1 and 2.

Any polynucleotide according to the present invention can be prepared by conventional techniques well known to those skilled in the art. For example, the polynucleotides can be prepared using conventional solid-phase synthesis using commercially available equipment, such as that available from Applied Biosystems USA Inc. (Foster City, Calif.), DuPont (Wilmington, Del.), or Milligen (Bedford, Mass.). Modified polynucleotides, such as phosphorothioates and alkylated derivatives, can also be readily prepared by similar methods known in the art. See, for example, U.S. Pat. Nos. 5,464,746; 5,424,414; and 4,948,882.

In some embodiments, the test sample is obtained from a subject, as described above. In these embodiments, the presence of TB-complex bacteria in the test sample is indicative of a TB-complex bacterium in the subject. The subject can be a human or animal suspected of having a latent or active TB infection. Alternatively, the subject can be a laboratory model for infection with TB and TB-complex bacteria. Thus, the method is useful for studying the progression and transmission of TB-complex bacteria. In other embodiments, the test sample is from a culture, such as tissue or cell culture. The disclosed method is useful for establishing contamination, or for monitoring the in vitro culturing of the TB-complex bacteria.

In another aspect, the present disclosure provides a method for monitoring the efficacy of treatment of a tuberculosis infection. The method comprises (a) determining the presence or amount of BlaC protein, nucleic acid encoding BlaC protein, or anti-BlaC antibodies in a biological sample obtained from a subject receiving treatment for tuberculosis according to the above descriptions; and (b) comparing the amount of BlaC protein, nucleic acid encoding BlaC protein, or anti-BlaC antibodies in the biological sample as determined in step (a) to a reference standard.

In some embodiments, the reference standard in step (b) is the amount of BlaC protein, nucleic acid encoding BlaC protein, or anti-BlaC antibodies determined in an analogous biological sample obtained from the subject at or after diagnosis with the tuberculosis infection but prior to the obtaining of the biological sample from the subject in step (a). A lower amount of anti-BlaC antibodies in the biological sample determined in step (a) compared to the biological sample in step (b) is indicative of a positive response to the treatment. In some embodiments, the reference standard is determined from a biological sample obtained from the subject at or prior to the commencement of treatment for the tuberculosis infection.

It will be appreciated that the applicable subjects and biological samples described above are equally applicable to the present aspects of the invention directed to detection of blaC sequence.

In another aspect, the present disclosure provides an isolated polynucleic acid with a detectable label covalently coupled thereto, wherein the isolated polynucleic acid is capable of hybridizing to a target region of a blaC gene encoding the amino acid sequence set forth in SEQ ID NO:2. In some embodiments, the isolated polynucleic acid comprises a nucleic acid sequence set forth in any one of SEQ ID NOS:3-29, or a homolog or variant thereof with about at least 90%, 95%, 96%, 97%, 98%, or 99% sequence identity thereto.

In some embodiments, the isolated polynucleotide further comprises a quencher moiety covalently coupled thereto.

In another aspect, the present disclosure provides a kit that comprises at least one of the isolated polynucleic acid molecules described immediately above. In some embodiments, the kit further comprises additional reagents to facilitate hybridization of the isolated polynucleic acid molecules to the target region of a blaC gene encoding the amino acid sequence set forth in SEQ ID NO:2, as described herein. In some embodiments, the kit includes primer oligonucleotides, as described herein, that are capable of amplifying a portion of the blaC gene encoding the amino acid sequence set forth in SEQ ID NO:2 under the conditions described herein.

In conclusion, the compositions, methods and systems described herein are useful to detect and monitor TB-bacteria. Many illustrative embodiments have been described, but the disclosure is not so limited. It will be appreciated by persons of skill in the art that many of the compounds, reagents, methods, systems, and kits described and contemplated herein can be incorporated with a variety of commonly recognized assay formats and their integral components, such as microfluidic systems, mass spectrometry systems, nanoparticle systems, microscopy systems, and the like. For example, microfluidics systems can be used to trap the protein and facilitate detection with antibodies or probes, mass spectroscopy, or other detection methods. Nanoparticle or nanopore systems can be developed using mirror thin films or particles that can be made to specifically detect proteins with structural and electrostatic properties similar to BlaC followed by mass spectroscopy, colorimetric, electronic or antibody-based detection of the protein. Microscopy could be used in combination with antibodies against BlaC to detect individual or clumps of bacteria augmenting smear microscopy already used and enhancing detection or improving specificity of current tests. These approaches can be used in combination with fluorescent or colorimetric antibody methods to detect the protein or intact bacteria in samples on slides. Magnetic bead separation can be used to allow more sensitive detection of BlaC in nearly any clinical material. Detection can be performed using FACS, microscopy, plate reader, MS, and the like.

Similarly, the described nucleic acid-based methods reagents can be developed and incorporated into a variety of known DNA or RNA analysis systems, such as qRT-PCR assays, molecular beacon assays, solid support systems, nanoparticles or thin films that carry at least a portion of the specific primers. Other strategies can be incorporated into a test system, including RNA primers, antibodies directed against nucleotide complexes, and hybridization complexes that produce colorimetric, fluorescent or luminescent output. Microfluidics systems can be used to trap the specific DNA or RNA for blaC and detection could be through PCR-like systems, hybridization to indicator probes or other automated strategies, including imaging techniques, FISH, scanning-tunneling microscopy, and electronic detection of hybridization. Magnetic bead separation could be used to improve yields of the target and increase the sensitivity of PCR, qRT-PCR or other detection methods. Detection of the blaC sequence can be accomplished using FACS, microscopy, plate reader, MS, and the like. An RNA-based test could have the advantage that it would allow measurement of viability due to the half-life of the blaC RNA transcript, which could be applied to evaluate therapeutic outcome and as the basis of a drug-susceptibility test (DST).

Unless specifically defined herein, all terms used herein have the same meaning as they would to one skilled in the art of the present invention. Practitioners are particularly directed to Sambrook et al., (1989) *Molecular Cloning: A Laboratory Manual*, 2d ed., Cold Spring Harbor Press, Plainsview, N.Y.; and Ausubel et al., *Current Protocols in Molecular Biology*, John Wiley & Sons, New York (1999) for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

The following disclosures provide illustrations of various aspects of the present disclosure. These disclosures are illustrative only and are understood to not be limiting to the spirit and scope of the disclosure.

I. The following disclosure describes a study demonstrating the specific and sensitive detection of *Mycobacterium tuberculosis* β-lactamase (BlaC) and TB complex bacteria expressing β-lactamase protein in biological samples using antibody-based immune-assay techniques.

β-Lactamase (BlaC) Protein Generation

*Escherichia coli* harboring an expression plasmid for *Mycobacterium tuberculosis* β-lactamase (BlaC) was cloned from *M. tuberculosis* genomic DNA. The gene, as set forth Gene ID: 888742 of GenBank genome accession no. NC_000962.3, was amplified using the polymerase chain reaction under normal conditions (see description of the original cloning of the gene in Wang, F. et al., "Crystal structure and activity studies of the *Mycobacterium tuberculosis* β-lactamase reveal its critical role in resistance to β-lactam antibiotics," Antimicrobial Agents and Chemotherapy 50(8):2762-2771 (2006), incorporated herein by reference in its entirety). The amplified blaC gene was subsequently inserted into the pET28b vector using NdeI and HindIII restriction sites. The resultant plasmid was transformed into *E. coli* BL21 strain. The transformed *E. coli* cells were validated and used for expression and purification of BlaC.

The *E. coli* strain was cultured in Luria-Bertani-Miller (LB) media (BD Biosciences, California, USA) containing 50 µg/ml of kanamycin, at 37° C. to obtain an optical density ($OD_{600}$) of 0.6. Expression of BlaC was then induced by the addition of isopropyl β-D-thiogalactopyranoside (IPTG, Gold Biotechnology, MO, USA) at 4° C. for 16 h. The cells were then harvested by centrifugation at 10,000 g and 4° C. for 10 minutes. The pellets were re-suspended in 25 mM Tris-HCl (pH 8.0) and lysed using three repetitive cycles of freeze-thaw followed by the addition of 2.5 unit/ml of benzonase (Novagen®, Darmstadt, Germany). The lysate was loaded onto a His-Prep™ column (GE Health Care, Buckinghamshire, UK), purification of BlaC was carried out according to the previously described protocol (Wang, F. et al., "Crystal structure and activity studies of the *Mycobacterium tuberculosis* β-lactamase reveal its critical role in resistance to β-lactam antibiotics," Antimicrobial Agents and Chemotherapy 50(8):2762-2771 (2006), incorporated herein by reference in its entirety), using the AKTA pure system (GE Health Care, Buckinghamshire, UK). Purified BlaC concentration of 4 mg/ml was finally achieved by dialysis with Spectra/Por® dialysis tubes (Spectrum Labs, TX, USA).

To validate the expression of BlaC from *E. coli* and the quality of the purified protein, samples were collected at various stages during the purification and run on a 12% SDS-polyacrylamide gel. It was observed that the amount of BlaC in the *E. coli* culture increased substantially following IPTG induction. Further, it is illustrated that upon lysis of the cells, maximal protein was retained in solution and not in the cell debris.

Characterization of recombinant β-lactamase (BlaC) As described, the purified BlaC protein was run on a 12% SDS-PAGE to check for purity and molecular weight. A single band was observed corresponding to molecular weight 32 kDa, indicating successful purification of the protein. The β-lactamase activity of BlaC was measured using nitrocefin (Calbiochem, MA, USA) as the substrate. When nitrocefin is hydrolyzed by β-lactamase, a hydrolyzed product is produced with a maximum absorption at 485 nm. Accordingly, the formation of the hydrolyzed product was monitored by absorbance at 486 nm ($A_{486}$) as an indicator of enzyme activity. Varying concentrations of the purified protein (0.25 to 25 nM) were added to 1×MES buffer in a 96 well plate, and the assay was initiated by the addition of 500 µM nitrocefin. The enzyme activity was monitored in EnVision® Multilabel reader (Perkin Elmer, MA, USA) with intermittent shaking for a period of 30 minutes. The resulting absorbance of hydrolysis product resulting from the varying concentrations of purified protein over time is illustrated in FIG. 1A. This demonstrates that enzyme activity is proportional to the concentration of the concentration of the purified protein.

Figure 1B:
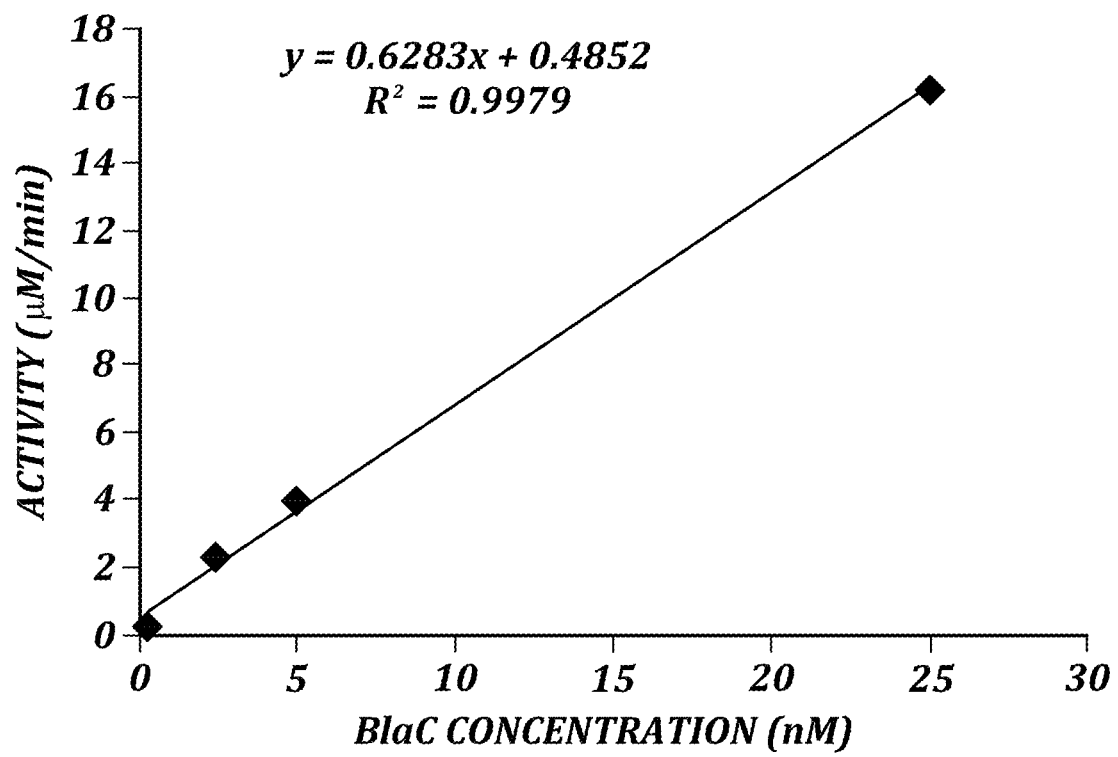
FIG. 1B graphically illustrates the enzyme activity of BlaC as a function of enzyme concentration. The observed rate of change at $A_{486}$ was converted to units of enzyme activity (μM product formed per minute) using the molar extinction coefficient of the hydrolyzed product of BlaC β-lactamase activity, which exhibits maximum absorption at 485 nm.

The observed rate of change in $A_{486}$ was converted to units of enzyme activity (µM product formed per minute) by using the molar extinction coefficient of the hydrolyzed product (20,500 $M^{-1}$ $cm^{-1}$) and the path length of 0.29 cm. As illustrated in FIG. 1B, the enzyme activity was found to increase linearly as a function of enzyme concentration ($R^2=0.99$), as expected. The purified BlaC was found to have an activity of 797±114 U/µM.

Generation of Anti-β-Lactamase (BlaC) Antibody

Antibody against purified protein was raised in rabbit (Bio Synthesis Inc., TX, USA). Briefly the rabbits were immunized with purified protein and a total of 100-150 ml of serum were collected with five boosts and four bleeds. Eighth and 10th week bleeds were tested by ELISA and used for further experiments, as described below.

Western Blot Analysis

To determine whether the antibodies generated using the recombinant BlaC protein could detect the protein in a biologically-relevant environment, a western blot analysis was conducted.

1) Sample Preparation

BlaC protein dilutions were made in phosphate buffered saline (PBS, pH 7.4). 50 µL of the diluted protein was added to 450 µL of sputum sample and mixed by pipetting. 500 µL of Transport Stabilization Solution (TSS), which primarily comprises MES buffer at pH 6.0, was added to the sample and further mixed to attain the best possible homogeneity. To each sample, 250 µL of Blue Sepharose™ 6 Fast Flow (Cibacron Blue) (washed and re-suspended in 1×MES) (GE Health Care, Buckinghamshire, UK) was added and mixed again to obtain optimal albumin removal. Various BlaC concentrations from 4 to 4000 ng were loaded onto the gels.

2) Detection

Ten µL of the BlaC samples (in sputum) were mixed with 10 µL of the loading dye, heated at 95° C. for 5 minutes and loaded onto 12% SDS poly-acrylamide gels. 400 ng of BlaC (in PBS) was also loaded as a positive control. The gels were run in duplicates at a voltage of 150 V until proper separation of the ladder was visually achieved. One of the two gels was coomassie stained to visually gauge protein levels and migration. The other gel was transferred to a pre-treated PVDF membrane. Pre-treatment involved submersion in 100% methanol for 5 minutes or until the membrane was translucent, followed by equilibration in the transfer buffer (3.03 g of Tris base, 14.4 g Glycine, 200 ml Methanol, and 800 ml dd$H_2O$) until the membrane no longer floated on the surface. The transferred membrane was immersed in blocking buffer (5 g non-fat milk in 100 ml of PBS buffer) and blocked overnight at 4° C. on a shaking platform.

After overnight blocking, the blot was immersed in primary antibody (i.e., the polyclonal anti-BlaC antibody from rabbit) diluted 1:5000 in primary antibody dilution buffer (i.e., wash buffer: 0.5 ml Tween 20 and 1000 ml PBS buffer). The blot was incubated for 1 hour at 37° C. on a shaking platform. Incubation with primary antibody was followed by washes with wash buffer (0.5 ml Tween 20 and 1000 ml PBS buffer) at room temperature for 10 minutes on a shaking platform. The washing step was repeated three times for a total of four washes. After the washes, the blot was immersed in secondary antibody (HRP-conjugated anti-rabbit IgG) diluted 1:10,000 in blocking buffer. The blot was incubated for 1 hour at 37° C. on a shaking platform. The blot was then washed again as described above. The blot was processed with SperSignal® West Pico Chemi-luminescent kit (Thermoscientific, IL, USA) according to the manufacturer's instructions and imaged after a 2 minute exposure.

Results: The western blot analysis demonstrated that BlaC concentrations of 400 ng and above in sputum could be detected using the rabbit anti-BlaC antibodies (not shown). The concentration threshold for detection could be attributed to the complexity of the sputum matrix obscuring detection of lower BlaC concentrations.

Enzyme-Linked Immunosorbent Assay (ELISA)

It is demonstrated above that western blot analysis using the generated antibodies can detect BlaC protein in a biological sample (i.e., sputum). To demonstrate the broader applicability of the anti-BlaC antibodies in other detection assays, an ELISA approach was explored.

One hundred µL of protein A/G (ProSpec, Ness-Ziona, Israel) (10 µg/ml in coating buffer: 1.59 g $Na_2CO_3$, 2.93 g $NaHCO_3$, 0.1 g Thimerosal, fill to 1000 ml with dd$H_2O$) was dispensed in 96 well plates. The plates were incubated at 4° C. overnight on a shaking platform. After the overnight incubation, the wells were washed with 200 µL of wash buffer (0.5% BSA and 0.05% Tween 20 in 1×PBS) at room temperature on a shaking platform for 5 minutes. The wash was repeated twice for a total of three washes. The wells were then blocked using the blocking buffer containing BSA (3% BSA in 1×PBS) for 1 hour at 37° C. on a shaking platform.

BlaC samples were processed similar to the western samples with the exception that primary antibody (i.e., the rabbit polyclonal anti-BlaC antibody) was added at a concentration of 1:2500 into the sputum to facilitate primary antibody binding with BlaC. The sample was incubated for 1 hour. 100 µL of sputum sample was dispensed into each well and incubated for 1 hour at 37° C. on a shaking platform. For bacterial samples, BCG was incubated in 10 ml M-OADC-Tw at 37° C., 5% $CO_2$ until an $OD_{600}$ of 0.5 was achieved. Appropriate volume of this culture was centrifuged and the pellet was re-suspended in 7H9 (BD Biosciences, California, USA). Bacterial suspension was further diluted in 7H9 media and instead of adding purified BlaC, bacterial dilutions were added to the sputum and incubated for 4 hours. The samples were processed here after as in step 4.

After incubation with sputum samples, the wells were washed with wash buffer as described above and re-blocked with non-specific mouse IgG diluted 1:5000 in blocking buffer to saturate the unbound protein A/G. The blocking was carried out for 1 hour at 37° C. on a shaking platform. After blocking, the wells were washed as described above. A 1:5000 dilution of primary antibody (i.e., the rabbit polyclonal anti-BlaC antibody) was added to the wells in wash solution. The wells were incubated for 1 hour at 37° C. on a shaking platform.

After incubation with primary antibody, the wells were washed as in step 1. 100 µL of secondary antibody (i.e., horseradish peroxidase (HRP)-conjugated goat anti-rabbit IgG) diluted in wash buffer was dispensed in each well. The wells were incubated for 1 hour at 37° C. on a shaking platform. The wells were washed again as describe above and 100 µL of 2, 2'-azino-bis (3-ethylbenzothiazoline-6-sulphonic acid) (ABTS) solution in citrate buffer was added to each well to serve as the HRP substrate. The plate was observed for development of color. Once discernible color was observed in the negative control (i.e., a well with no blocking buffer or secondary antibody) the reaction was stopped using 5% SDS. The formation of reduced ABTS as a measure of the amount HRP-labeled secondary antibody was read at 415 nm after approximately incubating for 5-10 minutes in EnVision® Multilabel reader (Perkin Elmer, MA, USA).

Statistical analysis and data plotting was performed using Excel (Microsoft Corp., WA, USA). Standard deviations and p-values were calculated.

Figure 2:
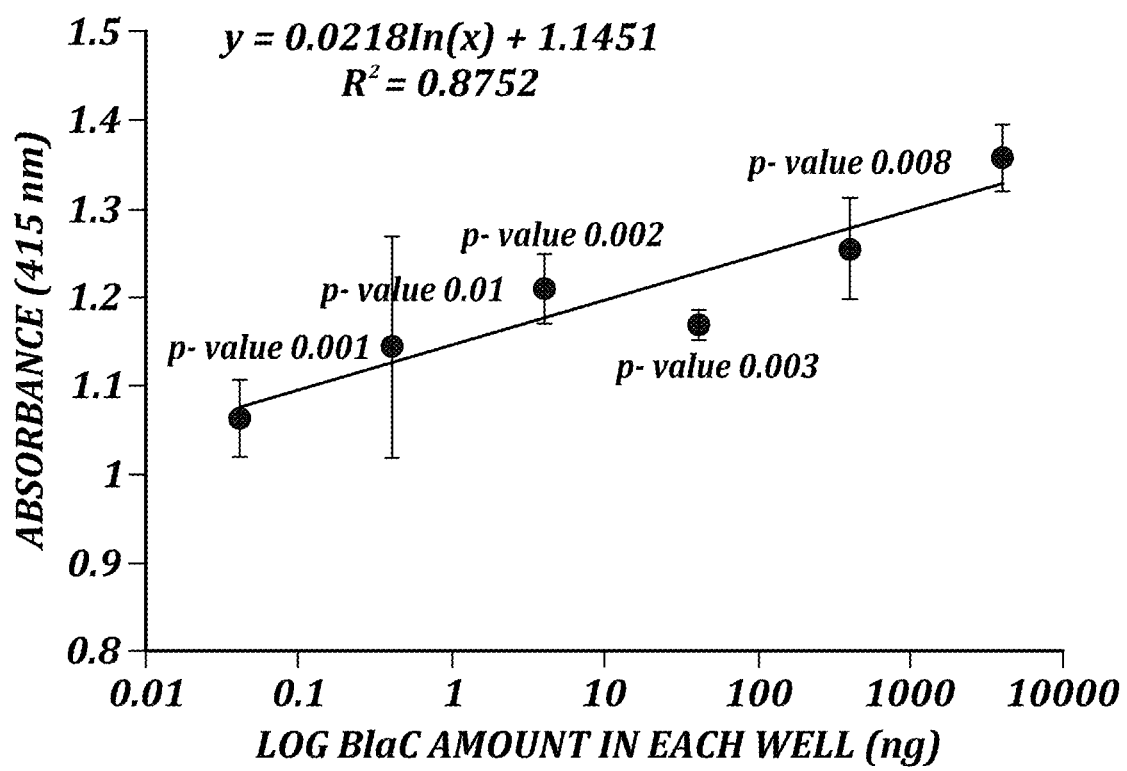
FIG. 2 graphically illustrates a standard plot of BlaC in sputum as determined using ELISA. Absorbance at 415 nm demonstrated a linear increase with the increase in BlaC concentration in sputum. The standard deviations and p-values are indicated.

Results: A standard plot of HRP activity was generated using BlaC dilutions in sputum. As illustrated in FIG. 2, the absorbance at 415 nm (i.e., indicating reduced ABTS) was found to linearly increase with the increase in BlaC concentration in sputum ($R^2$=0.87). The threshold for detection of BlaC in sputum was calculated at 0.04 ng, beyond which the detection was not linear and, hence, the absorption values were not included in the standard curve calculation.

Western Blot Analysis Using Bacteria

It is demonstrated above that standard western blot techniques using anti-BlaC antibodies can detect the presence of BlaC in biological samples (i.e., sputum). Accordingly, a preliminary assay was performed to ascertain whether whole bacteria are similarly detectable with the same reagents and techniques.

A preliminary western blot was carried out with bacteria (i.e., *M. bovis* (BCG)) diluted in sputum using the general protocol described above. BlaC from bacterial dilutions could not be detected in the preliminary western blots, suggesting that the amount or specific configuration of BlaC in live bacteria is not readily detectable by this basic method. The inability to detect BlaC from sputum sample by simple western blot analysis could largely be due to the fact that BlaC is associated with the bacterial cells, and a preliminary bacterial lysis might be required to obtain a more reliable estimate of BlaC presence. Prospective experiments will examine lysed cells to better localize the protein under these conditions. The intensity and duration of lysis will be standardized. Additionally the shortest incubation period of the bacteria in sputum resulting in reliable BlaC detection will be established. This refined assay will facilitate better understanding of BlaC production in sputum and the utility of western blot analysis to detect tuberculosis in infected patients.

ELISA Analysis Using Bacteria

It is demonstrated above that ELISA techniques using anti-BlaC antibodies can detect the presence of BlaC in biological samples (i.e., sputum). Accordingly, a preliminary ELISA was performed to ascertain whether whole bacteria are similarly detectable with similar reagents and techniques.

Figure 3:
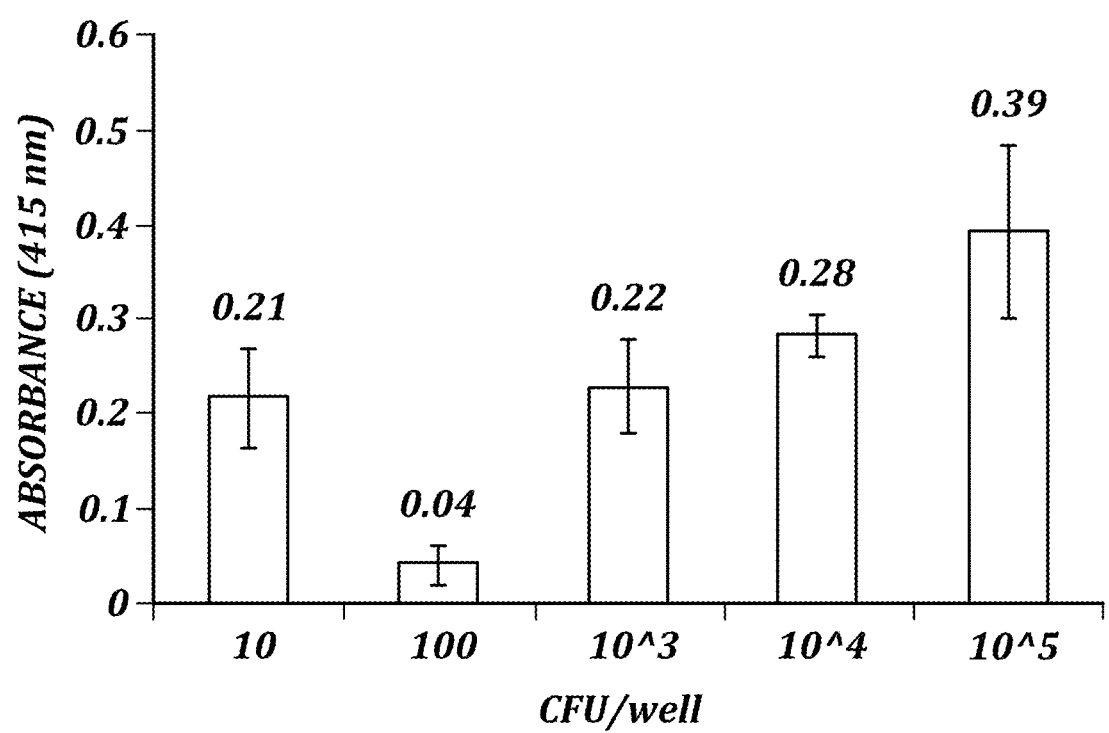
FIG. 3 graphically illustrates the detection of BlaC in *M. bovis* (BCG) bacterial dilutions in sputum using ELISA. The absorbance values (at 415 nm) for various CFU/well are indicated at the top of the bars.

A series of dilutions of bacteria (i.e., *M. bovis* (BCG)) were generated in sputum and assayed according to the general protocol described above. The absorbance values (i.e., indicating reduced ABTS and, thus, the presence of HRP-labeled secondary antibody) for the various bacterial concentrations sputum are illustrated in FIG. 3. A significant increase in signal was observed that correlated well with bacterial numbers. This correlation indicates the ability to detect whole bacteria in sputum using this method. Ultimately, the present results demonstrate that the amount of BlaC was increasing with the increase in CFU, as expected.

However, it is noted that the levels of bacterial BlaC detected by ELISA were low suggesting that the amount of BlaC produced less than the amount tested above to generate the standard curve. Thus, the present results were not extrapolated directly onto the current standard curve (as described above and illustrated in FIG. 2).

Surprisingly, the 10 CFU/well dilution of *M. bovis* (BCG) gave an unexpectedly high absorbance reading. This result is consistent with the inventor's observations that levels of BlaC activity are higher than expected when at low concentrations, such as 10 CFU of *M. bovis* (BCG) or Mtb. These observations were measured using custom BlaC substrates. Overall, this is an approximately 100-fold increase in BlaC activity above the expected level for this concentration, which is highly significant. Without being bound to any particular theory, these observations suggest that some aspect of the sputum environment increases the measurable BlaC activity, possibly as a result of increased expression, transport, activity or release of the protein. All of these possibilities warrant further investigation to better control for expression and perhaps increase the sensitivity of BlaC diagnostic strategies.

CONCLUSION

It is demonstrated that BlaC protein is detectible in sputum samples using antibodies generated against recombinant BlaC in rabbits. The antibodies were demonstrated as useful diagnostic reagents when used in both western blot analyses of sputum samples (incorporating the protein), and ELISA-based analyses of sputum samples (incorporating the protein or bacterial cultures).

II. The following describes an analysis of the β-lactamase DNA and protein sequences and the design of a specific and sensitive detection assay of tuberculosis-complex bacteria using β-lactamase nucleic acid as a biomarker.

BACKGROUND

A key first step in the development of specific and sensitive detection techniques for any pathogen is identifying unique aspects (e.g., sequences) that can reliably differentiate between the target pathogen and non-target organisms. Additionally, an ideal sequence target will be reliably expressed under a variety of conditions such as to provide ample nucleic acid template for sensitive detection at all stages of infection.

As described herein, the blaC gene of tuberculosis-complex bacteria is demonstrated to contain specific sequence domains that are not present in any other bacterial species. These unique domains present the opportunity to generate very specific probes. Furthermore, there is extensive evidence that blaC is constitutively expressed in tuberculosis-complex bacteria under nearly any condition at high levels, which makes it likely that detection reagents specific to the blaC RNA transcript will be highly sensitive and applicable to nearly any condition in vitro and during infections. Expanding upon published and available microarray and genomic data, analysis of the DNA and RNA sequences demonstrated that various sequences could be used for sensitive and specific reagents for tuberculosis-complex organisms. For example, TaqMan and molecular beacon probes are appropriate approaches for design of probes for this purpose. However, it will be understood that nearly any nucleotide recognition method could be used in a similar manner using the regions identified herein.

*Mycobacterium tuberculosis* (Mtb) BlaC is a naturally occurring class-A β-lactamase (Flores, A. R., et. al., "Genetic analysis of the β-lactamases of *Mycobacterium tuberculosis* and *Mycobacterium smegmatis* and susceptibility to β-lactam antibiotics," Microbiology 151(2):521-532

(2005), incorporated herein by reference in its entirety). BlaC is present in Mtb and all other tuberculosis-complex bacteria. The protein consists of 307 amino acids with a molecular weight of ~32 kDa. BlaC confers lactam antibiotic resistance to Mtb via hydrolysis of β-lactam antibiotics. As described below, use of the blaC RNA transcript is demonstrated as useful a tool for Mtb diagnosis. The RNA transcript can be amplified using reverse transcription, trapped, or directly amplified using various RNA-RNA amplification systems, and the like. Moreover, the described approaches could also be applied with very little modification to detecting blaC in the Mtb chromosomal DNA. The primary modification to the methodology for chromosomal detection is that DNA would be isolated and directly amplified or trapped for detection rather than RNA. Moreover, the described techniques can be applied to other bacteria from the TB-complex.

Constitutive expression can help ensure that blaC-detection is always sensitive and quantifiable, especially in the conditions mimicking the host environment prevalent during infection and latency in humans or animals. Numerous microarray data accessed from available TB databases (NCBI-GEO, etc.) demonstrate that the blaC gene is expressed constitutively when in intracellular environments, during growth in lab, and during infections, with no significant difference found between samples collected at 4 h and 24 h post-infection (Fontan, P., et al., "Global transcriptional profile of *Mycobacterium tuberculosis* during THP-1 human macrophage infection," *Infection and Immunity* 76(2):717-725 (2008), incorporated herein by reference in its entirety), under aerobic conditions (Voskuil et al., "The response of *Mycobacterium Tuberculosis* to reactive oxygen and nitrogen species," *Front. Microbiol.* 2:1-12 (2011), incorporated herein by reference in its entirety), or during an oxidative stress response (Rodriguez, G. M., et al., "ideR, an essential gene in *Mycobacterium tuberculosis*: role of IdeR in iron-dependent gene expression, iron metabolism, and oxidative stress response," Infection and Immunity 70(7):3371-3381 (2002), incorporated herein by reference in its entirety). Although none of these previous studies specifically examined blaC according to the present evaluation of these data, these observations indicate that blaC transcription is constitutive and the gene is a valuable target for development of new methods for diagnosis of TB-complex bacteria. Furthermore, the blaC gene is constitutively expressed 28 d post infection in experiments performed on BALB/c and SCID mice (Talaat, A. M., et al., "The Temporal expression profile of *Mycobacterium tuberculosis* infection in mice," Proceedings of the National Academy of Sciences of the United States of America 101(13):4602-4607 (2004)) and at least 30 d post-inoculation in a Wayne model depicting non-replicating persistence (Voskuil, M. I., et al., "*Mycobacterium tuberculosis* gene expression during adaptation to stationary phase and low-oxygen dormancy," Tuberculosis 84(3):218-227 (2004), incorporated herein by reference in its entirety) making it constitutively expressed under conditions commonly encountered by these bacteria.

Accordingly, the amino acid sequences of the BlaC protein were compared among members of the TB-complex. The BlaC amino acid sequence from Mtb was also compared against β-lactamases from other relevant pathogenic bacteria that are not part of the TB-complex. Similarly, the Mtb blaC gene sequence was compared with the β-lactamase gene sequences from other relevant pathogenic bacteria that are not part of the TB-complex. Based on these comparisons, specific sequences that differentiated Mtb and the TB-complex bacteria from other relevant pathogenic bacteria were identified and various detection reagents directed to the sequences were designed.

Demonstration of BlaC Specificity

Figure 4:
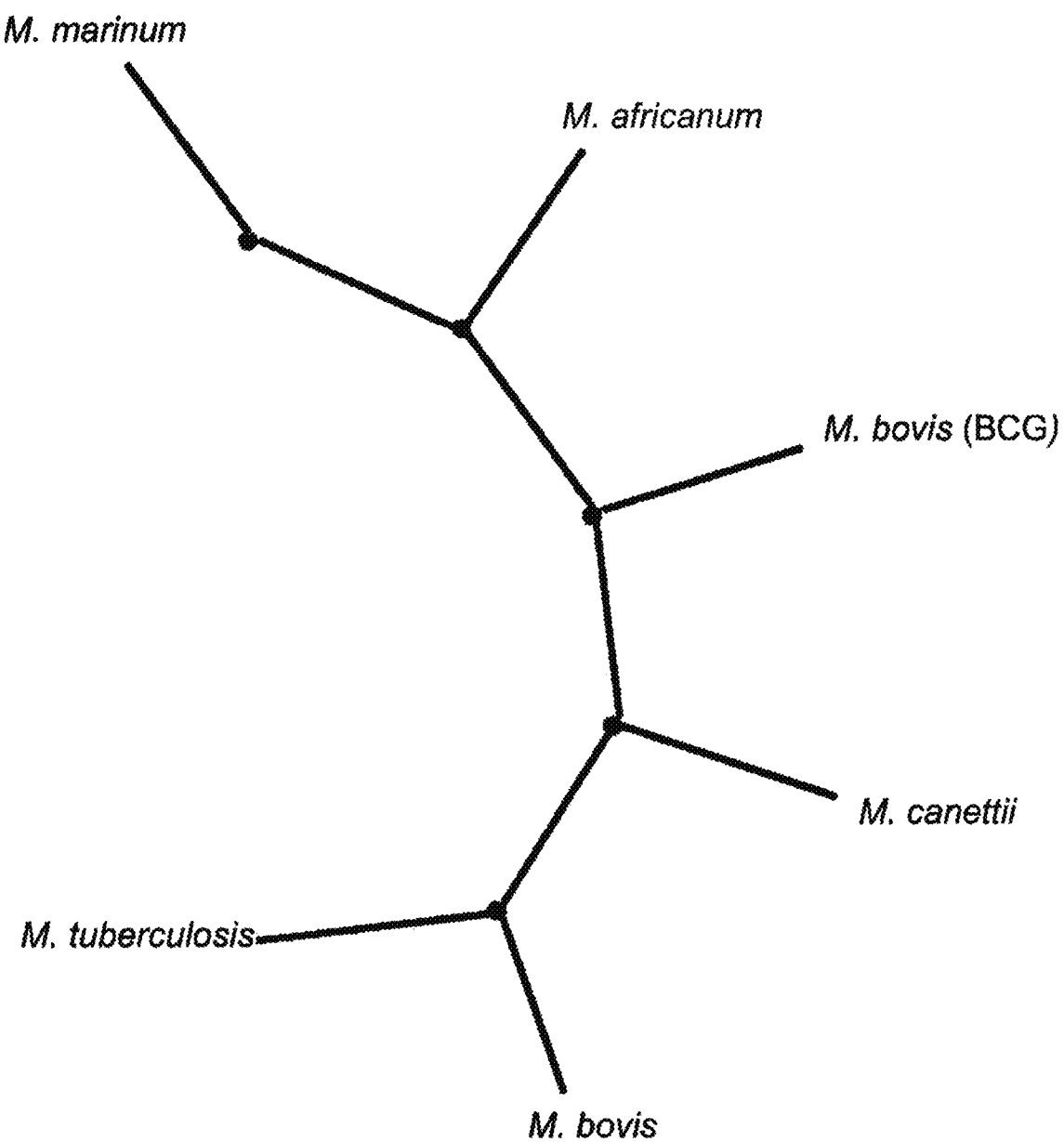
FIG. 4 is a force tree illustrating the phylogenetic relationships of *Mycobacterium* species based on the nucleotide sequences of β-lactamase. The sequences were compared between species in the TB-complex, and the most closely related *Mycobacterium* species that is not in the TB-complex, i.e., *Mycobacterium marinum*. The phylogenetic tree was generated by ClustalW2 (EMBL) using the nearest neighbor method and demonstrates that blaC is highly conserved in the TB-complex. *Mycobacterium marinum*, which is not a member of the complex, is separated from the complex by two nodes (phylogenetic distance).

The amino acid sequences of β-lactamases (BlaC) from bacteria belonging to the TB-complex, namely, *M. tuberculosis, M. bovis, M. bovis* (BCG), *M. canettii* and *M. africanum*, as well as β-lactamases (Bla) other pathogenic bacteria were obtained from the NCBI database and aligned using ClustalW2, a multiple sequence alignment tool from the European Molecular Biology Lab (EMBL). The β-lactamase (BlaC) protein showed 100% alignment identity within the TB-complex, indicating a high level of conservation. FIG. 4 illustrates the relationship of β-lactamase nucleotide sequence between the species within the TB-complex and the most closely related *Mycobacterium* that is not within the TC-complex, i.e., *Mycobacterium marinum*. This comparison demonstrates that the *M. marinum* β-lactamase has a two node distance from the TB-complex, suggesting that even the mycobacterial most closely related to the TB-complex species has β-lactamase that is not closely related to TB-complex blaC sequence. Thus, strategies to differentiate Bla (β-lactamase from non-TB-complex species) from BlaC (β-lactamase from TB-complex species) should be possible at the activity, protein and nucleotide level. FIG. 5 illustrates an alignment demonstrating that BlaC amino acid sequence is highly conserved (with 100% identity) in all TB-complex bacteria (this consensus sequence is set forth in SEQ ID NO:2). Three motifs (I, II, and III) that are known to be important for enzymatic activity are indicated in the alignment.

Figure 6:
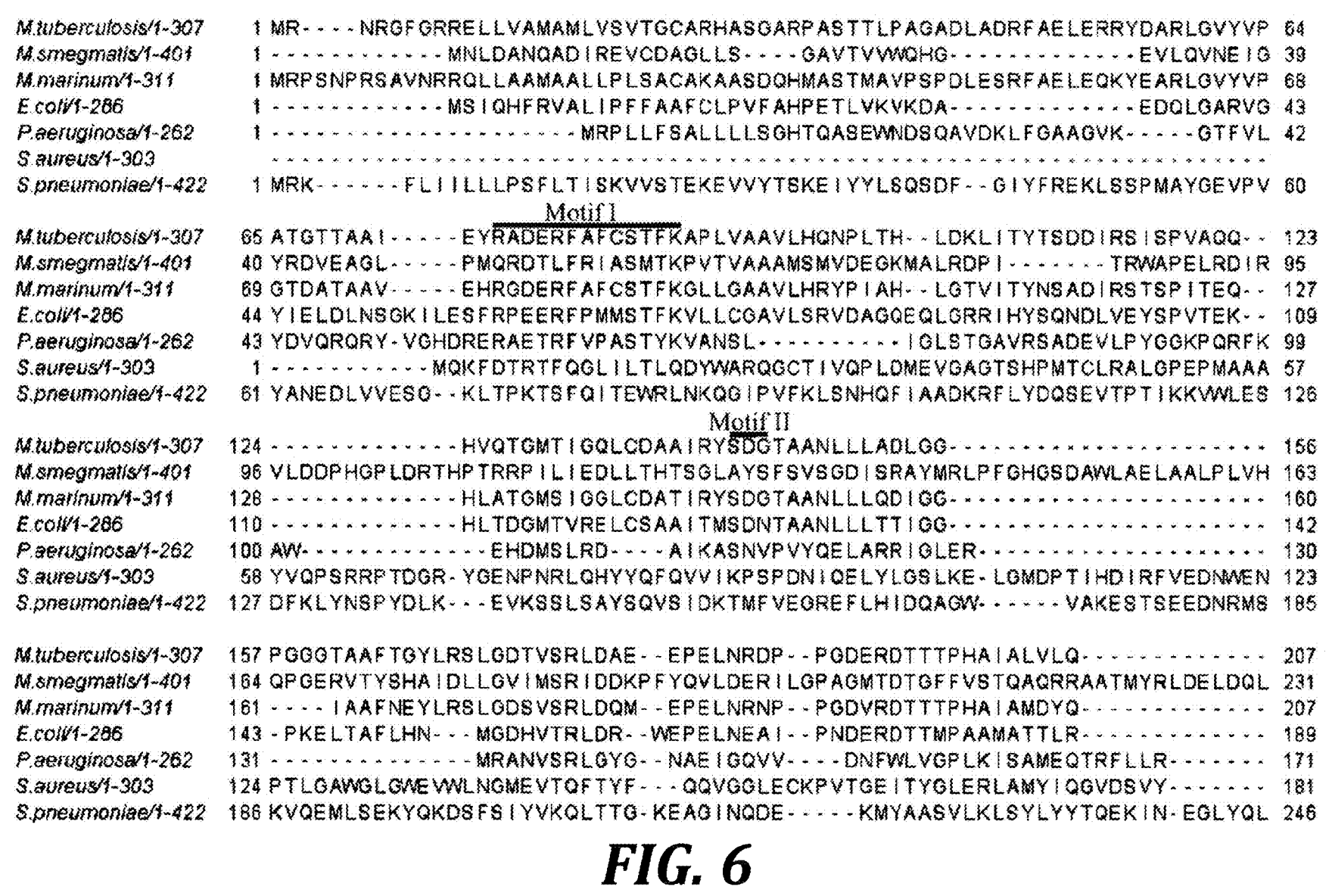

In order to determine which sequences, if any, are unique to the TB-complex BlaC, the BlaC protein sequence from Mtb was compare to the Bla protein sequences from various other bacteria using a multiple sequence alignment. This analysis, as illustrated in FIG. 6, revealed low similarity at the protein level among the compared species. Even in comparison to other mycobacterial species, low sequence similarity was observed throughout the entire BlaC amino acid sequence. This suggests that specific detection of TB-complex by virtue of unique BlaC and/or blac sequence is possible, even in the presence of numerous natural flora and other pathogens. The motifs that are conserved within the TB-complex bacteria and are necessary for the unique enzymatic activity are indicated in FIG. 6. The motif regions display the lowest amino acid similarity among the compared bacteria; there appears to be no sequenced Bla that is closely related to that present in TB-complex. In particular, even the active site of BlaC contains several glycine residues that are not present in any other bacterial species, indicating that even the active site sequences within the gene could be used as highly specific probes for TB-complex bacteria in clinical or environmental samples. In particular, all three TB-complex BlaC motifs (I, II, and III) are part of the active site, as described in more detail in Wang, F. et al., "Crystal structure and activity studies of the *Mycobacterium tuberculosis* β-lactamase reveal its critical role in resistance to β-lactam antibiotics," Antimicrobial Agents and Chemotherapy 50(8):2762-2771 (2006), incorporated herein by reference in its entirety. Briefly, the following discussion makes reference to residues as numbered in the Wang reference with an indication of the corresponding residue in SEQ ID NO:2, as disclosed herein. In all class A β-lactamases like BlaC, hydrolysis of the β-lactam substrates is achieved by a nucleophilic attack initiated by active-site serine residue Ser70 (corresponding to the serine at position 84 of SEQ ID NO:2). It has been proposed that Glu166

(corresponding to the glutamic acid at position 182 of SEQ ID NO:2), a general base in the active site, is the serine70-activating residue. Glu166 (corresponding to the glutamic acid at position 182 of SEQ ID NO:2) has been established as being critical for the deacylation of the acyl-enzyme intermediate. Ser70 (corresponding to the serine at position 84 of SEQ ID NO:2) and Lys73 (corresponding to the serine at position 87 of SEQ ID NO:2), located on α-helix H2 in the center of the active site are, also crucial and completely conserved in all class A β-lactamases. These residues are surrounded by other important residues on β-strand B3 (Lys234, Thr235, and Thr237; corresponding to the lysine, threonine, and threonine at positions 250, 251, and 253, respectively, of SEQ ID NO:2) and the loop region between H5 and H6 (Ser130 and Gly132; corresponding to the serine and glycine at positions 142 and 144, respectively, of SEQ ID NO:2), as well as the S2 loop (Glu166; corresponding to the glutamic acid at position 182 of SEQ ID NO:2). These eight residues are all involved in direct hydrogen bonding interactions with β-lactam substrates. Two bound water molecules, WAT36 and WAT65, are also highly conserved in the structures of all class A β-lactamases determined to date.

Design of blaC-Specific TaqMan® Probes

One embodiment of a PCR-based detection assay incorporates a TaqMan® probe, wherein the probe contains a fluorophore and a quencher configured such that when the probe is intact, no detectable signal is observed. As is well-understood in the art, the probe is designed to hybridize to a portion of the target. The probe is cleaved when primers are extended from either side of the target region, thus releasing the fluorophore from proximity of the quencher and resulting in detectable signal. Exemplary primer couples and probes were designed using Eurofins MWG Operon (AL, USA) software. Four primers and their respective probes were selected based on nBLAST analyses, absence of secondary structure, melting temp ($T_m$) and length of the amplicon (Table 1). Primer probe sets with a $T_m$ difference of more than 10° C. were not considered. All probes, when subjected to BLAST, showed homology to the TB complex with very low expected value (E-values), suggesting that the probability of their binding to any other bacterial DNA is highly unlikely.

TABLE 1

Exemplary TaqMan primer and probe combinations designed for specific detection of TB-complex blaC. The corresponding sequence identifier numbers (i.e., SEQ ID NO:) are indicated in parentheses.

| | Forward primer | Reverse primer | TaqMan® probe |
|---|---|---|---|
| 1 | GACGAACGGGATACCACAAC (12) | ATCCAATCGGTGAGCAGTGC (21) | TTGCCGAGAACAAGCTGCTG CAACACCA (3) |
| 2 | CATTCTGCTCCACGTTCAAG (13) | ATCGACCGAATGTCGTCAC (22) | TTTGTCCAGATGCGTGAGCG GGTTTTGGT (4) |
| 3 | CGAACGGGATACCACAACAC (14) | ATCCAATCGGTGAGCAGTGC (23) | TTGCCGAGAACAAGCTGCTG CAACACCA (5) |
| 4 | CATTCTGCTCCACGTTCAAGG (15) | TCGACCGAATGTCGTCACTG (24) | ATCAGTTTGTCCAGATGCGT GAGCGGGTTTT (6) |

Use of active site probes may have some advantage because divergence in this sequence would potentially impact activity and would be selected against evolutionarily, making the probe effective under most conditions.

Figure 7:
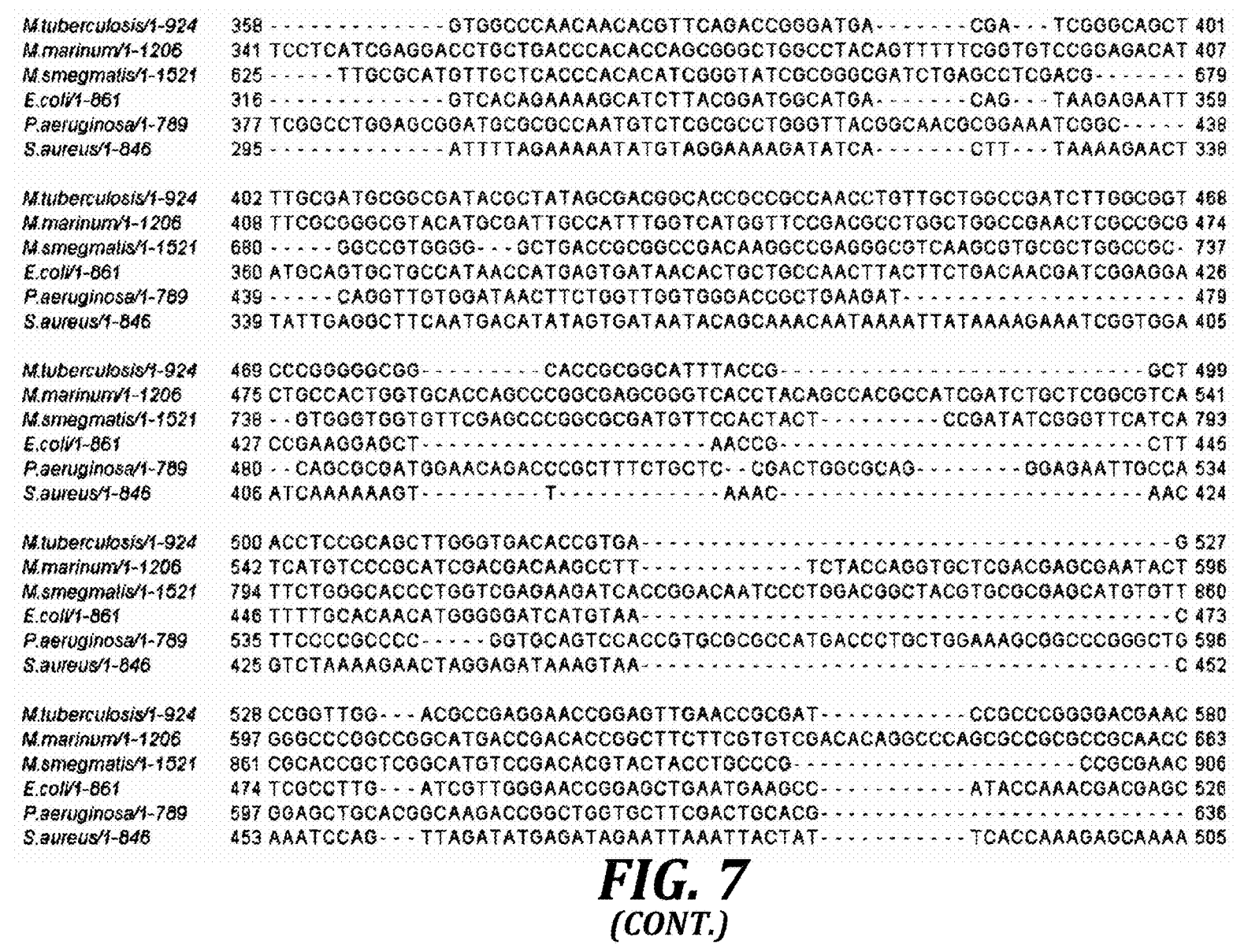

Upon the discovery that there were numerous sequences within BlaC that diverge from the sequences of other Bla proteins, polynucleic acid primers were considered for use in a detection system that would specifically target TB-complex sequence. To this end, specific details regarding the nucleotide sequences of blaC gene were sought. As an initial step in this process, an alignment was generated comparing the nucleotide sequences of the blaC gene from TB-complex bacteria with the sequences of the bla gene from a diverse set of organisms, including other Mycobacteria sp. As illustrated in FIG. 7, similar results were obtained with the nucleotide sequence as those using the protein sequence. Specifically, while conserved regions were identified that could not be used for design of probes, several regions of blaC are unique to the TB-complex gene and are not present in any other bacterial species. These observations demonstrate that the design of probes specific for TB-complex is possible, which probes can be used to evaluate the presence of these bacteria in nearly any clinical or environmental sample. The preferred parameters of probe design are that the probes are sensitive, specific and conserved throughout all TB-complex bacteria.

Design of Molecular Beacon Probes

Another embodiment of a PCR-based detection assay incorporates a molecular beacon probe. As is well-understood in the art, the molecular beacon probe contains a hairpin configuration with a loop comprising the probe sequence that is complementary to the target nucleic acid sequence. The stem of the hairpin structure is formed by complementary oligonucleotide sequences that are at the 5' and 3' end of the linear sequence. A fluorophore is covalently attached to the end of one of the stem oligonucleotides, whereas a quencher dye is covalently attached to the end of the other stem oligonucleotide. When in the initial hairpin configuration, the probe does not emit a detectable signal. However, when annealing to the target sequence, the probe linearizes permitting a sufficient distance to form between the fluorophore and quencher dyes, thus allowing a detectable signal. Such a probe can be incorporated into PCR-based amplification assays. Exemplary molecular beacon probes were designed using BeaconDesigner™ 8.0 (Premier Biosoft, CA, USA). Because the use of beacon probes can also be incorporated into PCR-based assays, amplification probes were also designed in conjunction with specific beacon probes (i.e., with forward and reverse primers that anneal 5' and 3' to the annealing site of the beacon probe). The program facilitates optimal primer and beacon probe design with the annealing temperature of the beacon being at least 9° C. above the $T_m$ of the primers. Five primer and beacon probe sets were identified (Table 2). The beacons for each set were subjected to nBLAST. The beacon showing the lowest E-value is indicated (with *) in the table and will be the probe of choice for this approach.

showing the lowest E-value and maximum query coverage is SEQ ID NO:9 (Table 2, row 3), which was used in conjunction with the primers with sequences set forth in SEQ ID NOS: 18 and 27, as the probe of choice due to its lowest similarity to non-mycobacterial sequences. Thus,

TABLE 2

Exemplary molecular beacon primers and probes designed for specific detection of TB-complex blaC. The corresponding sequence identifier numbers (i.e., SEQ ID NO:) are indicated in parentheses.

| | Forward primer | Reverse primer | Probe |
|---|---|---|---|
| 1 | CATCTGGACAA (16) | ATAGCGTATCG (25) | CGCGATCCCAGTGACGACATTCGGTGATCGCG (7) |
| 2 | TTCGCATTCTG (17) | ACTGGTGTAGG (26) | CGCGATCGCTCACGCATCTGGACAAGATCGCG (8) |
| 3 | TCGCATTCTG (18) | TGTCGTCACT (27) | CGCGATCCTCACGCATCTGGACAAACGATCGCG* (9) |
| 4 | TTCGCATTCTG (19) | ACTGGTGTAGG (28) | CGCGATCCAAAACCCGCTCACGCATGATCGCG (10) |
| 5 | ATACCACAACA (20) | GCCATCCAAT (29) | CGCGATCGAACAAGCTGCTGCAACAGATCGCG (11) |

Primers generated in this method, such as the disclosed primers, are extremely specific for TB-complex blaC nucleic acids, and are useful for either RNA or DNA amplification and/or detection. In some detection strategies, RNA can be amplified without PCR. Moreover, both DNA and cDNA may be amplified randomly prior to PCR to increase sensitivity. Additional validation of these primer sets can involve examination of their conservation in all TB-complex bacteria and particularly the numerous TB strains that have been sequenced to ensure that the final probe is specific, sensitive and highly conserved. With all three of these characteristics, a probe based on this strategy would be applicable to all conditions. In contrast, without all three of these characteristics, a probe based on this strategy would not be generally applicable to all conditions.

III. The following describes the successful use of nucleic acid primers and probes directed to the β-lactamase nucleic acid sequence to specifically detect the presence of tuberculosis-complex bacteria.

BACKGROUND

As described above in part II, β-lactamase (BlaC) can be a useful biomarker for tuberculosis-complex bacteria. As further described, in silico analysis of all available β-lactamase sequences demonstrated that β-lactamases are conserved in TB-complex bacteria, yet are unique as compared to all other non-TB-complex sequences, including eukaryotes and prokaryotes. Accordingly, the present discussion validates the concept that TB-complex bacteria can be specifically detected by virtue of the unique nucleic acid sequence.

Method and Results

BeaconDesign 8.0 was used to design optimal primer and beacon sets with the annealing temperature of the beacon being at least 9° C. above the $T_m$ of the primers. Five primer and beacon sets were identified (see Table 2, above). The beacon for each set was subjected to nBLAST, that includes all eukaryotes and prokaryotes currently sequenced for a total of over 20 million sequences and >50 billion nucleotides as of Nov. 11, 2013 (not shown). The beacon probe 3 (set forth in SEQ ID NO:9) was the best of the five beacons designed using the BeaconDesign software and was selected in conjunction with the corresponding primers (see Table 2, row 3) for synthesis, characterization, and validation in detection assays using chromosomal DNA from humans, Mtb and various bacterial pathogens, including *M. marinum, M. avium, Pseudomonas, Staphylococcus*, and others. The selected probe and primer set were ordered from Integrated DNA technologies and used for the real-time experiments.

Mycobacterial DNA was extracted from BCG cultured in 100 ml M-OADC-Tw media at 37° C. until an $OD_{600}$ of 0.8 was achieved. The cells were pelleted out by centrifugation at 3500 rpm for 15 min and re-suspended in minimal amount of saline solution (0.9%). Cell lysis was achieved by addition of 500 µL of acid washed beads in 750 µL of TE buffer per 250 µL of re-suspended pellet, followed by vortexing. Lysed cells were centrifuged at 10,000 rpm for 10 min and the supernatant was collected. RNAseA was added to the supernatant to a final concentration of 0.1 mg/mL followed by incubation at 37° C. for 1 hr in order to eliminate RNA contamination from the supernatant. Equal volumes of phenol-chloroform-isoamyl alcohol was added to the supernatant and incubated for four minutes with gentle rocking followed by centrifugation at 10,000 rpm for 10 min. The supernatant was collected and DNA was precipitated by adding 3 M NaOAc in the ratio of 1:10 and two volumes of cold ethanol. The precipitated DNA was then pelleted out by high speed centrifugation (13,000 rpm) followed by 70% ethanol washes. The DNA pellet was dissolved in TE and stored at 4° C. for further use. DNA concentration and quality of the extracted DNA was determined.

The concentration of extracted Mycobacterial DNA was estimated to be 455 ng/µl. 1:10 dilution of this sample was loaded onto an agarose gel to visually establish DNA quality (not shown).

Molecular Beacon real-time PCR was carried out using the selected set of primers and probe (see Table 2, row 3). The PCR reaction contained 10 to 100 ng of BCG DNA, 7 mmol/L final concentration of $MgCl_2$, 200 µmol/L concentration of dNTP, 2.5 U of taq DNA polymerase, 0.2 µmol/L final concentrations of the primer pair and 0.2 μmol/L final concentration of the beacon. The PCR was performed on the Applied Biosystem, step one real-time PCR system, using the following cycling conditions: 95° C. for 3 min, followed by 50 cycles of 94° C. for 20 s, 42° C. for 20 s, and 72° C. for 20 s. Each sample was loaded as duplicates for technical controls.

Figure 8:
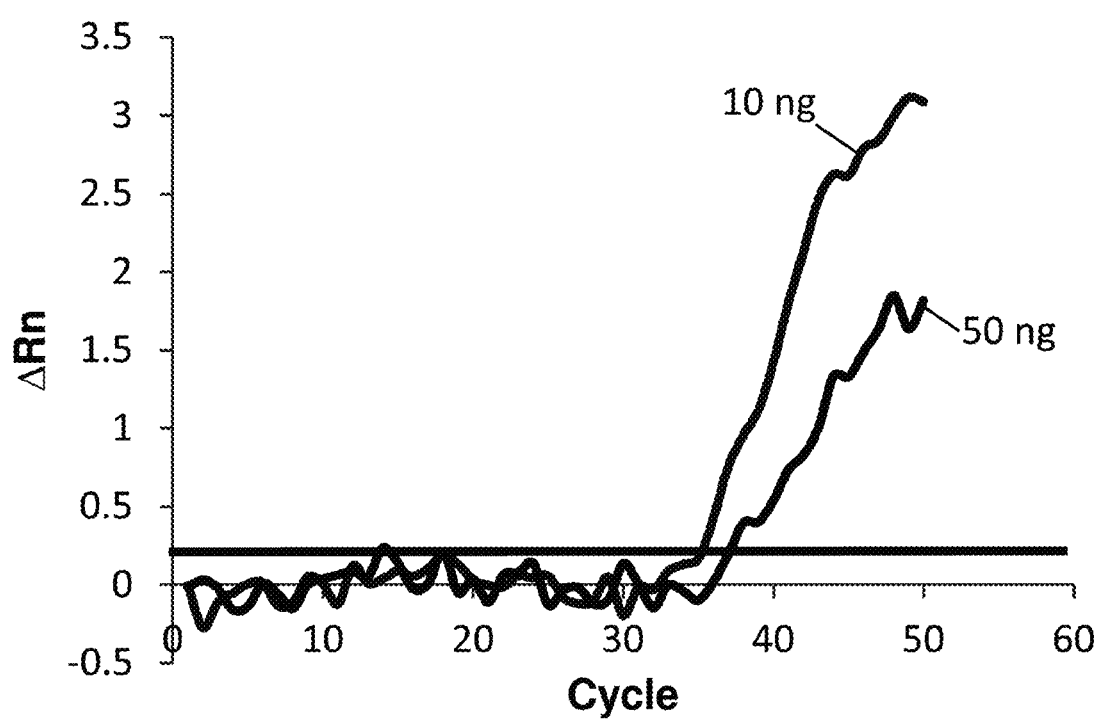
FIG. 8 graphically illustrates the amplification plots of representative 10 ng (upper line after round 35) and 50 ng (lower line after round 35) samples of template.

Real-time amplification using the beacon was carried out and the results are summarized in Table 3. A minimum of 10 ng of DNA per well was detected, which was the genomic equivalent of $2\times10^6$ Mycobacterium cells. Representative amplification plot for 10 ng and 50 ng DNA per well have been shown in FIG. 8.

TABLE 3

Cycle number at which detection was possible for various concentrations of DNA

| DNA concentration (ng) | Cycle number[a] |
|---|---|
| 10 | 35 ± 0.04 |
| 50 | 37 ± 0.3 |
| 100 | ND[b] |

[a]Number of cycles at which the fluorescence generated by the cleavage of the beacon hairpin due to amplification by the primer set was detectable above the background.
[b]Not detected Additionally, RNA was extracted and cDNA was synthesized from various bacterial samples including MRSA, *E. coli, Salmonella, Mycobacterium smegmatis, Pseudomonas* PAO1 and *Bacillus*. Briefly, the bacterial cells were lysed using TRIzol reagent (Invitrogen). RNA samples were treated with RNase-free DNase I (Promega), followed by purification using the RNeasy Mini Kit (Qiagen). The concentration of RNA was estimated using a NanoDrop ND-1000 spectrophotometer (version 3.1.0; Thermo Fisher Scientific). Reverse-transcription reactions on total RNA were performed using the First Strand cDNA Synthesis Kit (Invitrogen) with random decamers.

Real-time PCR was carried out using the synthesized cDNA and the designed Beacon. No signal was observed with cDNA corresponding to the various bacteria (not shown), suggesting that the designed probes as expected were specific for the mycobacterial complex.

To further improve the threshold for detection (e.g., to facilitate reliable and specific detection of lower amounts of TB-complex bacteria in a sample), bacterial genomic DNA yields can be enhanced through achieving enhanced bacterial cell lysis. Furthermore, an improved detection threshold can be achieved through enhanced DNA isolation and purification techniques. This is a useful improvement and consideration the observation that DNA concentrations higher than 50 ng did not give provide signal (not shown). This result implied that there was a considerable amount of impurity in the extracted DNA sample and at higher concentrations these impurities inhibited the real-time PCR assay.

CONCLUSION

It is demonstrated that nucleic acid probes and primers designed to hybridize to unique sequences of consensus blac from TB-complex bacteria facilitates the PCR-based specific detection of TB-complex bacteria and does not cross-react with other, non-TB-complex bacteria.

IV. The following describes the generation and purification of goat polyclonal antibodies that bind to BlaC protein.

The polyclonal antibodies were analyzed for utility as either a capture or detection reagent in a lateral flow detection platform.

Antibody Production

Polyclonal Goat anti-BlaC (PAC 8577) was custom made by Pacific Immunology. Briefly, pre-immune serum was first collected and then 200 μg of BlaC antigen and 200 μg of Complete Freund's Adjuvant were injected into a goat host. Five subsequent boosts of 100 μg of antigen and 100 μg of Incomplete Freund's Adjuvant took place over the next six months. About two months from the initial immunization, the first production bleed commenced, collecting approximately 300 ml of serum. An ELISA was performed on the first bleed with a titer of ~1:500,000. The subsequent production bleeds occurred about every two weeks thereafter. The second production bleed produced a serum volume of 329 ml. The third production bleed produced a serum volume of 250 ml. The serum was split into two batches and affinity purified separately to ensure isolation of all the specific antibody from the serum. Approximately 16.1 mg of affinity purified antibody were obtained and the ELISA results showed a titer of ~1:500,000. The fourth production bleed produced a serum volume of volume of 290 ml. The fifth production bleed (performed after a four-week interval) produced a serum volume of 310 ml. This bleed was also affinity purified, following the same procedure described above. Approximately 15.4 mg of purified antibody was obtained and the ELISA results showed a titer of ~1:500,000. The sixth production bleed produced a serum volume of 292 ml. This bleed was also affinity purified, using BlaC immobilized on an affinity support column. Approximately 14.4 mg of purified antibody was obtained and the ELISA results showed a titer of ~1:500,000.

Affinity purification referred to above was generally conducted by chemically immobilizing BlaC antigens on an affinity support column. When the goat serum was passed over the column, goat anti-BlaC antibodies bound to the BlaC antigens. The support was washed with additional buffer to remove non-bound components. Finally, elution buffer was added to remove goat anti-BlaC from the immobilized BlaC on the support, resulting in the releasing of goat anti-BlaC antibodies in its purified form from the original serum.

ELISA titer results represent a relative measurement of the quantity of peptide-specific antibody present in serum samples. Titer was determined by diluting the serum samples until the antibody level gave values on the plate reader approaching background levels. Titer of 1:500,000 means this is the dilution that gives a reading of approximately 0.1 O.D. above background.

Lateral Flow Assay

A preliminary BlaC Lateral Flow Assay was performed using the polyclonal Goat anti-BlaC antibody 0.7 mg/ml (PAC 8577) as both capture antibody on the test line and label antibody in the gold conjugate. The test line was striped at 0.5 mg/ml on nitrocellulose membranes. The Goat anti-BlaC antibody was conjugated to 40 nm colloidal gold particles at 6 μg per 1 ml of gold. Buffers and blocking agents were optimized for the detection of BlaC spiked in a buffer solution. At this scale, the limit of detection was 10 ng/ml of BlaC at 15 min. The preliminary lateral flow assay demonstrates excellent sensitivity, establishing that that the goat polyclonal antibody reagent can be useful in capture and detection of BlaC. Ideally, the polyclonal reagent is paired with another polyclonal antibody or specific monoclonal anti-BlaC antibody to provide excellent specificity and sensitivity in an immunoassay.

V. The following is an overview describing the successful production and analysis of monoclonal antibodies from rabbit ("RabMAb®") that specifically bind to the active BlaC enzyme of TB-complex bacteria.

OVERVIEW

Active and inactive forms of BlaC protein antigens were recombinantly produced as described above and contained His-tags to facilitate isolation/purification. The active form of BlaC is also referred to herein as KES-1A antigen, whereas the inactive antigen, referred to herein as KES-1B, is a BlaC preparation with a high proportion of enzyme demonstrating diminished enzymatic activity). KES-1B and an irrelevant His-tagged protein, referred to herein as KES-1C antigen, were used for counterscreening.

Two, 3-month old New Zealand White rabbits were subject to a pre-immunization bleed (5 mL) one day prior to immunization. The rabbits were immunized using a customized protocol of four subcutaneous injections and two production bleeds per rabbit. The first immunization included the KES-1A antigen aliquot (0.4 mg) combined with Complete Freund's Adjuvant (CFA). The subsequent injections included 0.2 mg KES-1A with incomplete Freund's Adjuvant (IFA) at 3, 5, and 7 weeks after the initial injection. The production bleeds were performed just before the last injection and at two months after the initial injection.

Serum obtained from the production bleeds were screened by ELISA to establish titers against the KES-1A (active BlaC), KES-1B (inactive BlaC), and KES-1C (irrelevant protein) antigens using Abcam standard protocols. The immunization produced good antibody titers (not shown) for the immunogen was 1:64,000. The cross-screening demonstrated very little cross-reactivity for the KES-1C (His-tagged) antigen, indicating minimal reactivity with the His-tag, and an overall lower titer against the "inactive" BlaC (his-tagged).

The rabbit with higher anti-BlaC titer was selected for splenectomy and monoclonal development. The rabbit was subject to a final immunogen boost and the spleen was harvested and splenocytes were isolated using standard protocols four days thereafter. Two hundred million lymphocyte cells were fused with 100 million fusion partner cells on two separate days and plated on twenty 96-well plates on each day. The plates were kept in tissue culture incubators under standard conditions. Cell growth was examined 2-3 weeks after fusion and fusion efficiency (calculated as the total number of wells containing hybridoma cell colonies divided by the total number of wells examined) was analyzed. A minimum of two plates were examined per fusion.

After fusion, all multiclone supernatants were screened by standard ELISA for reactivity with the BlaC protein (KES-1A) antigen. For each ELISA screen, antigens were coated at 50 ng per well, and the original rabbit bleed at 1:10,000 dilution was used as a positive control. A total of 29 ELISA positive multiclones were identified and then expanded to 24-well plates. A confirming screen was subsequently performed for all positive multiclones using the BlaC protein antigen (KES-1A), the inactive BlaC (KES-B), and the irrelevant his-tagged protein antigen (KES-1C), as described above. Fifteen multiclones were determined to show reactivity with the BlaC protein (KES-1A) antigen, and therefore were confirmed positive.

After the multiclone supernatant evaluation, three clones (i.e., 20, 22 and 27) were selected for subcloning. Subcloning was performed by limited cell dilution method, where cells were seeded into 96-well plates at a concentration of 1 cell/well, with a total of three 96-well plates per multiclone. All subclones were screened again by ELISA against the BlaC protein antigen. For each multiclone, 12 positive subclones were selected and expanded into 24-well plates. A subclone confirming ELISA screen was performed using the BlaC protein (KES-1A) antigen, the inactive BlaC (KES-1B) antigen, and the irrelevant his-tagged protein (KES-1C) antigen on the 12 positive subclone supernatants per multiclone (36 subclones total). The IgG concentration of the 36 subclone supernatants was measured by ELISA as well. All 36 subclone supernatants showed positive reactivity towards the BlaC protein antigen.

A competition ELISA was performed to better simulate antibody binding under similar conditions as during the lateral flow assay. For the competition ELISA, the plate was coated with the BlaC protein (KES-1A) antigen, and was run using a standard ELISA protocol except the subclone supernatants were incubated with either PBS, or the antigen for 1 hour in solution before being added to the antigen-coated plate. This is to better simulate how the antibody would bind the antigen in solution in a lateral flow assay. Subclones from parental clones 27 and 22 showed decreased binding to the plate when incubated with the BlaC protein (KES-1A) antigen in solution first, which indicates that these clones bind strongly to the antigen in solution. Subclones (e.g., 20-8, 22-12, and 27-11) were selected to be expanded and frozen according to the protocols described below.

The hybridoma complete growth medium included RPMI 1640 medium with 0.05 mM 2-mercaptoethanol, Abcam Media Supplement A (catalog number ab138912), containing antibiotic/antimycotic/Gentamicin), and 10% fetal bovine serum.

Hybrodima propagation was performed by centrifugation with subsequent resuspension in hybridoma complete growth medium. New cultures were established at 0.1 million cells/ml and maintained between 0.1-1 million cells/ml. Medium was changed every 3 to 6 days. Subclones were screened and determined to be negative for *Mycoplasma*.

Hybridoma cells were frozen in 90% FBS and 10% DMSO.

Monoclonal antibody production is performed by expanding the selected subclones and harvesting supernatants, as is commonly performed in the art. Purified monoclonal antibodies can be tested for IgG concentration, specific activity by ELISA, and purity by SDS-PAGE.

CONCLUSION

RabMAbs® were successfully generated against the BlaC protein. Further efforts include production of purified antibodies and screening for specific detection of BlaC protein from TB-complex bacteria as compared to the BlaC protein from non-TB-complex bacteria, the characterization of the specific epitope conferring specific recognition, and the implementation of the monoclonal antibodies in detection assay formats.

VI. The following is an overview describing the successful production and analysis of monoclonal antibodies from Mouse that specifically bind to the active BlaC enzyme of TB-complex bacteria.

Monoclonal antibodies were produced in mice that specifically bind to BlaC as compared to an irrelevant protein (TEM1). The antibodies were generated and were screened by ELISA according to the same general strategies described above in Part V for Three clones (i.e., 31A, G1 and H1) produced ample amounts of antibody that exhibited no cross-reactivity with the irrelevant TEM1 antigen, even with TEM1 at double concentration (1.0 µg/ml) when compare to BlaC 0.5 µg/ml antigen.

Accordingly, Mouse monoclonal antibodies were successfully produced that specifically bind to BlaC. Further efforts include production of purified antibodies and screening for specific detection of BlaC protein from TB-complex bacteria as compared to the BlaC protein from non-TB-complex bacteria, the characterization of the specific epitope conferring specific recognition, and the implementation of the monoclonal antibodies in detection assay formats.

VII. The following describes the successful detection of BlaC present in sputum using a lateral flow assay format incorporating the rabbit-derived monoclonal antibodies described above.

Methods

The lateral flow assay components were prepared and assembled according to the following procedures.

Nitrocellulose Membrane Preparation: Test and control lines were sprayed on Sartorius CN 95; 30 mm with 1.0 mg/ml antibody (Mouse anti-BlaC H-1, RabMab 20-8, RabMab 22-12 or RabMab 27-11) or 0.5 mg/ml Goat anti-BlaC as the test line and 0.5 mg/mL of Goat anti-Mouse, Goat anti-Rabbit, Donkey anti-Goat or the combination of three as the control line. Striping Buffer is 1×PBS pH 7.4; 0.2% Sucrose. The test line and control line were sprayed 7 mm apart using the Biodot sprayer. The test line was 11 mm from the bottom of the membrane. Membranes were striped at a rate of 1.0 µl/cm. The membranes were dried at 37° C. for 1.0 hour and stored in a desiccated foil pouch. Striped membranes were kept desiccated overnight before blocking.

Antibody Gold Conjugation Protocol: Using Slide A-Lyzer 10000 MWCO RabMab 20-8 and Mouse anti-BlaC H-1 were dialyzed in 10 mM Potassium Phosphate pH 7.4 overnight. After dialyzing, the final concentration of RabMab 20-8 was 1.0 mg/ml, and Mouse anti-BlaC H-1 was 0.715 mg/ml. Amicon Ultra-0.5 Centrifugal Filter devices were used to concentrate and dialyze Goat anti-BlaC, RabMab 22-12 and RabMab 27-11. The final concentration of Goat anti-BlaC was 13.68 mg/ml; RabMab 22-12 had the concentration of 4.48 mg/ml, and RabMab 27-11 had 3.84 mg/ml.

Colloidal Gold Solution, at room temperature, was adjusted to desirable pH for each antibody (pH 7.6 for RabMab 22-12, 8.0 for Goat anti-BlaC, 8.4 for RabMab 20-8, 8.6 for RabMab 27-11 and Mouse anti-BlaC) with fresh made 0.1M $K_2CO_3$. Then, the dialyzed antibodies were added to colloidal gold solution with vortexing. The solution was incubated for 30 minutes on a rotator at room temperature. The conjugate was blocked with 10 µl (for every 1 ml of OD 2 colloidal gold) of Conjugate Blocking Buffer (25 mM Borate Buffer; 6% BSA; 0.2% Bioterge; 0.3% Sucrose) on a rotator at room temperature for 10 minutes. The gold conjugate was centrifuged at 12000 RPM, 4° C. for 20 minutes and the supernatant discarded. The conjugate pellet was re-suspended with 0.2 ml (for every 1 ml of OD 2 colloidal gold) Conjugate Re-suspension Buffer (25 mM Borate Buffer; 1.2% BSA; 0.04% Bioterge; 0.06% Sucrose). Conjugate Blocking Buffer and Conjugate Re-suspension Buffer with pH 7.8 were added to gold conjugate solution pH 7.6 and 8.0; those with pH 8.6 were added to gold solution pH 8.6. OD of gold conjugate was checked using a spectrophotometer and adjusted to 10-12. The gold conjugate was stored at 4° C. until use.

Membrane blocking: Striped membrane CN 95 was placed into Lateral Flow Blocking solution (25 mM KP04; 0.2% Casein; 0.5% Boric Acid; 0.02% Sucrose; 0.1% Surfactant 10-G; 0.5% PVA) with the orientation of the test line at the bottom of the nitrocellulose and the control line on the top of the nitrocellulose. The blocking solution was allowed to wick up to the top of the membrane. The membrane was removed from the blocking solution and placed in a finger rack to dry at 37° C. for 1 hour. Blocked membranes were placed in a desiccated plastic bag and store in a dry room.

Glass fiber blocking: 300 mm Millipore G041 glass fibers were saturated with LF blocking buffer using a P-1000 pipette. After 15 minutes, the fibers were transferred to a paper towel. After one minute, the fibers were place on the finger rack to dry at 37° C. for an hour. Blocked glass fibers were put in a plastic bag with desiccators and store in a dry room.

Gold Conjugate Pad Preparation (for dried conjugate pad testing method): The OD (10 to 12) gold conjugate was prepared by adding 10% Sucrose and 5% Trehalose to the conjugate. The gold conjugate was dispensed by pipetting at the rate of 1 µL/mm on 4 mm assembled test strips. The test strips were dried at 37° C. for 1 hour, packed in a desiccated foil pouch, and stored in a dry room.

Test Strip Lamination: Striped nitrocellulose membrane was laminated onto vinyl backing card. The wick pad was placed on the top portion of backing overlapping the membrane by 2 mm. The 10 mm conjugate pad was overlapped onto the membrane by 2 mm. The sample pad was placed on top of the conjugate pad with a 15 mm overlap from the bottom of backing card.

Test Strip Cutting: Assembled cards were cut into 4 mm strips using Biodot CM4000 cutter.

The BlaC lateral flow assay was tested according to the following procedures.

General assay testing: 70 µL of running buffer (negative control) or diluted sample in running buffer (positive control) was pipetted into sample pad. The running buffer contained 1×PBS; 0.05% BSA; 0.1% Triton X-100; 0.2% Tween-20. The test line intensity after the 15th minute was observed and evaluated.

Wet testing method: 3 µL of gold conjugate and 30 µL of sample or buffer (negative control) was pipetted into a well of a micro plate and mixed. Test strips that did not have conjugate and sample pads were allowed to sit in the well for 15 minutes. The test line intensity was observed and evaluated.

Dried down conjugate method: Pipetted 4 µL of gold conjugate onto conjugate pad of each strip. Dried the strips at 37° ° C. for 1 hour.

Antibody pairing: Each antibody was striped on CN95 membrane and gold conjugation was performed. Each antibody was experimented (paired) against itself and other antibodies using the generated membranes and gold conjugates.

Results

To determine optimal pH for the new anti-BlaC RabMAb® antibodies, the gold conjugation protocol was performed using a pH range of colloidal gold from 7.2 to 9.0, with 0.2 of increment. For each pH gold conjugate solution, the concentration of antibodies was 6 µg/ml. 5.0 µL of each final gold conjugate solution was spotted on G041 glass fiber and dried at 37° C. for 30 minutes.

Generally, the optimal pH of a gold conjugate would be the lowest pH that, after drying, exhibits the best cherry red color on the glass fiber. This indicates there is little to no aggregation of the gold-antibody conjugate. The optimal pH of the various antibodies were observed to be pH 8.4 (RabMab 20-8), pH 7.6 (RabMab 22-12), and pH 8.6 (RabMab 27-11).

Antibody pairs were screened among Goat anti-BlaC, Mouse anti-BlaC H1, RabMab 20-8, RabMab 22-12, RabMab 27-11, to determine which pair(s) yield(s) useful signal intensities. All pair combinations were performed, such that each pair member served as a detection antibody (i.e., gold-conjugated) and a capture antibody (striped on a "test line" (TL). The gold conjugation protocol described above was performed to prepare each antibody. The capture antibodies were striped on CN95 membrane. For control, 0.5 mg/ml Donkey anti-Goat, Goat anti-Rabbit, Goat anti-Mouse, or combinations of these control capture antibodies were striped on a control line (CL). Membranes were blocked and BlaC was applied in the wet testing method (described above).

Figure 9:
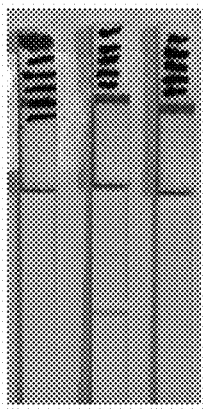
FIG. 9 provides illustrative test strips run using the wet method using Goat anti-BlaC as an immobilized capture antibody and RabMab 22-12 as a gold conjugated detection antibody. From left to right: running buffer as negative control, 50 ng/ml, and 3 ng/ml BlaC. 0.5 mg/ml Donkey anti-Goat, Goat anti-Rabbit, Goat anti-Mouse, or combinations of these control capture antibodies were striped on a control line (CL) to indicate that binding conditions were proper.
Figure 10:
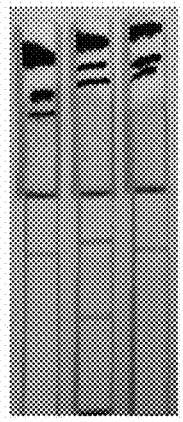
FIG. 10 provides illustrative test strips run using the wet method using RabMab 20-8 as an immobilized capture antibody and RabMab 27-11 as a gold conjugated detection antibody. From left to right: running buffer as negative control, 50 ng/ml, and 3 ng/ml BlaC. 0.5 mg/ml Donkey anti-Goat, Goat anti-Rabbit, Goat anti-Mouse, or combinations of these control capture antibodies were striped on a control line (CL) to indicate that binding conditions were proper.

Fifteen pairs of antibodies yield observed signals on test lines (TL). Criteria of determining good pair(s) of antibodies included: negative control stays negative (no TL observed); 50 ng/ml and 3 ng/ml BlaC have strong signal intensities. A pair of Goat anti-BlaC as a capture and RabMab 22-12 as a conjugate meets the criteria. See FIG. 9. As illustrated in FIG. 9, the negative control remained negative (left strip), the signal intensity of 50 ng/ml BlaC (middle strip, lower band) is 7 and that of 3 ng/ml BlaC is shadow (right strip, lower band). Another pair of antibodies matching the criteria is RabMab 20-8 as a capture and RabMab 27-11 as a conjugate. See FIG. 10, which also illustrates no lines for the negative control, the 50 ng/ml BlaC is 7 of the signal intensity (middle strip, lower band), and 3 ng/ml BlaC shows shadows of that signal (right strip, lower band).

General observations include that the strips had pinkish backgrounds with some exhibiting aggregation at the bottom. This was attributed to the wet method not containing 5% Trehalose and 10% Sucrose to stabilize and flow smoothly on test strips.

For negative control, weak test line signals (the intensity from +/− to VF) were observed on some strips. Furthermore, test strips without conjugate and sample pads do not eliminate non-specific binding very well; as a result, some feint signals were observed.

Suboptimal coloring was also observed in some cases where bold red lines at the control line (CL) position were not observed because antibodies in the gold-conjugate solutions were not compatible or did not bind well to antibodies at test line (TL) position. For example, where the RabMab 22-12 antibody served as the gold conjugate and was paired with Goat anti-Rabbit antibody was striped on the on control line (CL), the positive control signal was weak. Although these two antibodies are compatible binding partners, they did not bind well together as would be expected. In other combinations, the gold-conjugated antibody (e.g., Goat anti-BlaC) was paired with an incompatible antibody on the control line (CL), such as Goat anti-Rabbit (instead of the control Donkey anti-Goat). Because these were not compatible antibodies, a CL signal was not a bold red line. However, in cases using Mouse anti-BlaC H-1, and the three RabMab antibodies, optimal control coloring was observed because the control lines consisted of both Goat anti-Mouse and Goat anti-Rabbit antibodies.

Cross reactivity to other β-lactamase (Bla) proteins was evaluated for RabMab 22-12 and RabMab 27-11 (serving as the gold-conjugated detection antibody). RabMab 22-12 was paired with goat anti-BlaC as the capture antibody and RabMab 27-11 was paired with RabMab 20-8 as the capture antibody and the test line (TL). Gold conjugation, membrane striping, blocking, and dried down testing were performed as described above using BlaC and five difference β-lactamase (Bla) proteins (at 1 μg/ml and 500 ng/ml).

Only BlaC-positive control samples yielded positive results at test line (TL) positions, while the other β-lactamase samples did not produce positive signals (not shown). Therefore, no cross activity occurred between the two antibody pairs (Goat anti-BlaC/RabMab 22-12 and RabMab 20-8/RabMab 27-11) and four different β-lactamases (AG Scientific LN: 1163, AG Scientific LN: 2467, Novus Biological and OXA-48).

It is noted that the gold conjugate solutions for dried down conjugate method consisted of 5% Trehalose and 10% Sucrose. As a result, the conjugates stabilized and flowed smoothly on test strips. Thus, all strips had clear backgrounds, and did not exhibit any precipitated particles during test running. In addition, the control lines (CL) of test strips for pairing of Goat anti-BlaC (capture) and RabMab 22-12 (conjugated detection) antibodies were bold red lines. However, the control lines from the pairing of RabMab 20-8 (capture) and RabMab 27-11 (conjugated detection) antibodies were fade red lines because RabMab 27-11 did not bind well with Goat anti-Rabbit antibody used at the control line (CL). A weak control line notwithstanding, the red control line indicates the strip works properly.

The negative control samples remained negative because the test strips were assembled with conjugate and sample pads such that non-specific binding was not observed.

Signal intensity was assessed for chosen antibody pairs with a series of BlaC concentrations. Gold conjugation, striping blocking, and dried down testing method protocols were generally followed as described above for increasing concentrations of BlaC.

The pairing of RabMab 20-8 (capture) and RabMab 27-11 (conjugated detection) antibodies detected the presence of BlaC at the concentration of 9 ng/ml (not shown). The pairing of Goat anti-BlaC (capture) and RabMab 22-12 (conjugated detection) antibodies detected the presence of BlaC at the concentration of 3 ng/ml.

It is noted that the gold conjugate solutions for dried down conjugate method consisted of 5% Trehalose and 10% Sucrose. As a result, the conjugates stabilized and flowed smoothly on test strips. Thus, all strips had clear backgrounds, and did not exhibit any precipitated particles during test running. In addition, the control lines of test strips from the pairing of Goat anti-BlaC (capture) and RabMab 22-12 were bold red lines. However, the control lines from the pairing of RabMab 20-8 (capture) and RabMab 27-11 (conjugated detection) were faded red lines because RabMab 27-11 did not bind well with Goat anti-Rabbit antibody, which was striped at the control line (CL). A weak control line notwithstanding, the red control line indicates the strip works properly.

Negative control samples remained negative because test strips were assembled with conjugate and sample pads, such that non-specific binding was not observed.

DISCUSSION

Regarding antibody pair screening, the two best antibody pairs from a total 25 pairs were Goat anti-BlaC as a capture reagent paired with RabMab 22-12 as a conjugated detection reagent, and RabMab 20-8 as a capture reagent paired with RabMab 27-11 as a conjugated detection reagent. RabMab 20-8, RabMab 22-12, RabMab 27-11 and Mouse anti-BlaC H-1 did not pair to themselves. RabMab 22-12 did not pair well with RabMab 27-11, RabMab 22-12 and RabMab 27-11 (as capture antibodies) did not pair well with Mouse anti-BlaC H-1 and RabMab 20-8 (as conjugated detection antibodies), respectively.

Regarding cross reactivity, Goat anti-BlaC/RabMab 22-12 and RabMab 20-8/RabMab 27-11 pair did not exhibit any cross activities with β-lactamases from other, non-TB complex sources (AG Scientific LN: 1163, AG Scientific LN: 2467, Novus Biological and OXA-48).

Regarding signal intensity, the pair of RabMab 20-8 and RabMab 22-12 detects the presence of BlaC at the concentration of 9 ng/ml. The pair of Goat anti-BlaC and RabMab 27-11 detects the presence of BlaC at the concentration of 3 ng/ml. The test strip format demonstrated the capacity for optimization to produce clear assay background and minimized (or no) precipitated detection particles.

Accordingly, these results demonstrated the successful development of lateral flow assays incorporating pairs of anti-BlaC antibodies that demonstrate accurate and sensitive detection of BlaC markers in a relevant biological sample.

VIII. The following describes an additional embodiment of a lateral flow assay that was successful in detecting BlaC in sputum.

Methods

Assay strips were assembled. As a preliminary step, detection reagent was generated by generating antibody-gold conjugates, as described above, using 6 μg/mL with the RabMab 27-11 clone at pH 8.6. The conjugate sample was adjusted to an OD of 10 and 10% sucrose and 5% trehalose were added. The gold conjugate was striped onto G041 10 mm glass fiber conjugate pad (Millipore) and blocked with LF blocking buffer at 12 μL/cm. The pad was dried at 37° C. for 1 hour and kept desiccated overnight before use. Membrane striping was performed on CN95 nitrocellulose membrane using Goat anti-Rabbit (Lampire Biological Labs) and Donkey anti-Goat (Lampire Biological Labs; LN: 09C21103) antibodies in a final concentration of 1 mg/mL. Test line was striped with Goat-anti BlaC at a concentration of 1 mg/mL (the antibody was concentrated from 0.7 mg/mL to 13.5 mg/mL before striping). The membrane was dried at 37° C. for 1 hour and kept desiccated overnight before use. The CN95 membrane, wick pad (EMI 30250), and conjugate pad (G041), were assembled onto a backing card (G&L; PN: GL-57065; LN: 1100603/1030805) and cut into 4 mm wide strips. Such assemblies (assay strips) could be used immediately or stored in desiccated environment for long term. For sample preparation, 50 mL of digestion buffer (0.2 M citrate, 50 mM TCEP, 0.3% fish gelatin, 0.1% Proclin, pH 6.0) was prepared. Specifically, 2.941 g of citric acid and 0.716 g were added to about 40 mL of DI water and stirred until completely dissolved. 1.5 mL of 10% fish gelatin and 0.515 mL of Proclin 950 were added to the solution. The pH was titrated up to 6.0 with 10 N NaOH and QS to 50 mL with DI water and with final pH confirmed at RT.

3 mL of digestion buffer was added to 3 g sputum (1:1 ratio). The sample was vortexed and allowed to digest for 30 minutes. The sample was filtered through a 5 um filter (Whatman Sum GD/X Filter, Cat #6870-2550 (25 mm diameter)) and filtrate was collected.

BlaC was spiked in sputum sample at final concentrations of 0.5 ng/mL, 1 ng/mL, 2 ng/mL, 5 ng/mL, 10 ng/mL, 20 ng/mL, 50 ng/mL, 100 ng/mL, 200 ng/mL, 500 ng/mL, and 1000 ng/mL. The remainder of the unspiked sputum filtrate was filtered through a 0.2 um filter (Whatman 0.2 um GD/X Filter, Cat #6870-1302 (13 mm diameter)). The filtrate was collected and spiked with BlaC at the concentrations indicated above for the single-pass filtrate. 100 uL of samples were pipetted onto each well on the 96-microplate plate. Individual strips were dipped into the sample wells and stopped running after 15 minutes by removing wick pad, conjugate pad, and sample pad from strips. The strips were inserted into an Axxin reader (Axxin, Fairfield, Australia) for quantitation.

The CL and TL intensities from the Axxin quantitation for the 5 μm sputum filtrate spiked with varying concentrations of BlaC are provided in Table 23. The TL readings are illustrated graphically in FIG. 37. The CL and TL intensities from the Axxin quantitation for the 0.2 μm sputum filtrate spiked with varying concentrations of BlaC are provided in Table 24. The TL readings are illustrated graphically in FIG. 38.

Results

Figure 11A:
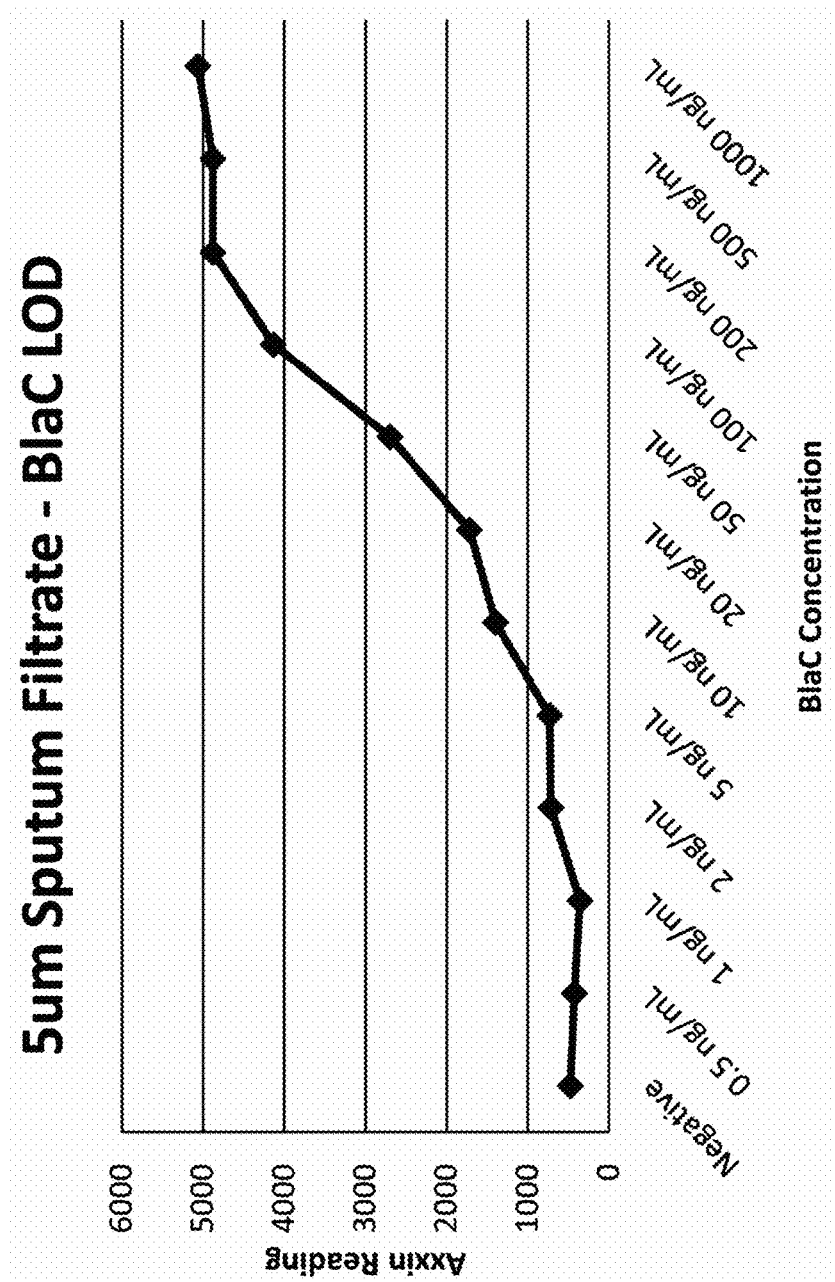
FIG. 11A graphically illustrates the Axxin readings of BlaC as determined from 5 μm filtered and spiked sputum.
Figure 11B:
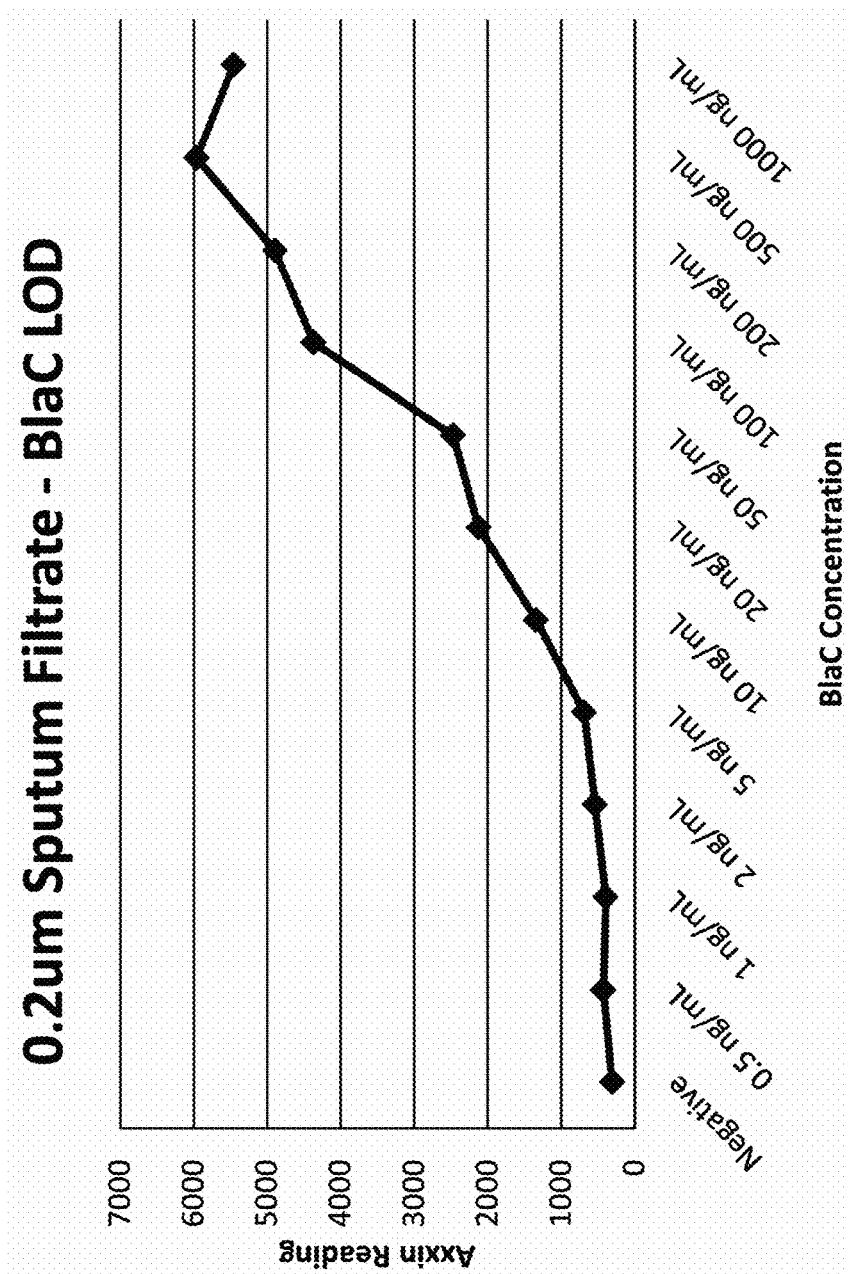
FIG. 11B graphically illustrates the Axxin readings of BlaC as determined from 0.2 μm filtered and spiked sputum.

The intensities of control line (CL) and test line (TL) signals as determined by the Axxin reader are set forth in Tables 4 and 5 for the sputum samples filtered with 5 μm (first pass) and 5 μm followed by 0.2 μm (second pass) membranes, respectively. The TL intensities obtained from each filtrate are also graphically illustrated in FIGS. 11A and 11B.

TABLE 4

5 μm sputum filtrate (first pass) readings spiked with varying concentrations of BlaC

| Concentration | CL Intensity | TL Intensity |
| --- | --- | --- |
| Negative | 12890 | 472 |
| 0.5 ng/mL | 12905 | 428 |
| 1 ng/mL | 12813 | 356 |
| 2 ng/mL | 13610 | 715 |
| 5 ng/mL | 13465 | 730 |
| 10 ng/mL | 13491 | 1395 |
| 20 ng/mL | 12033 | 1718 |
| 50 ng/mL | 11807 | 2696 |
| 100 ng/mL | 12525 | 4131 |
| 200 ng/mL | 11753 | 4876 |
| 500 ng/mL | 9949 | 4876 |
| 1000 ng/mL | 10797 | 5061 |

TABLE 5

0.2 μm sputum filtrate (second pass) readings spiked with varying concentrations of BlaC

| Concentration | CL Intensity | TL Intensity |
| --- | --- | --- |
| Negative | 10895 | 309 |
| 0.5 ng/mL | 13388 | 426 |
| 1 ng/mL | 13713 | 394 |
| 2 ng/mL | 14015 | 542 |
| 5 ng/mL | 12332 | 689 |
| 10 ng/mL | 12182 | 1344 |
| 20 ng/mL | 11775 | 2122 |
| 50 ng/mL | 10297 | 2471 |
| 100 ng/mL | 11989 | 4367 |
| 200 ng/mL | 11991 | 4895 |
| 500 ng/mL | 11755 | 5959 |
| 1000 ng/mL | 11074 | 5456 |

Both 5 urn (first pass) and 5 um/0.2 urn (second pass) sputum filtrates show similar performance and results for detection of BlaC in the sputum using the test strips and Axxin reader. Sensitivity was as low as 2 ng/mL of BlaC final concentration in each sample, demonstrating the utility of the antibody reagents and test apparatus.

IX. The following describes an assay demonstrating a successful detection of BlaC in a saliva sample using the lateral flow assay.

Saliva collection was performed by placing sponge (America Filtrona sponge) in mouth for ten minutes to absorb saliva. Once saturated, the sponge was placed in a 5 mL syringe, and squeezed to collect saliva in a 2 mL dolphin tube. The saliva was spiked with BlaC at a range of concentrations. The spiked saliva was mixed with running buffer (10 mM Tris, 1% Tween-20, pH 7.2) at 1:1 ratio and vortexed to mix to provide final concentrations of BlaC of 0.5 ng/mL, 1 ng/mL, 2 ng/mL, 5 ng/mL, 10 ng/mL, 20 ng/mL, 50 ng/mL, 100 ng/mL, 200 ng/mL, 500 ng/mL, and 1000 ng/mL. 100 µL saliva-buffer mix was pipetted and run on strips (generated and assembled as described above). Results were read after 15 minutes using an Axxin reader.

Results

The intensities of control line (CL) and test line (TL) signals as determined by the Axxin reader are set forth in Table 6 for the saliva samples. The TL intensities indicated in Table 6 are also graphically illustrated in FIG. 12.

TABLE 6 intensity readings for saliva spiked with varying concentrations of BlaC

| Concentration | CL Intensity | TL Intensity |
|---|---|---|
| Negative | 7483 | 344 |
| 0.5 ng/mL | 8463 | 394 |
| 1 ng/mL | 7729 | 635 |
| 2.5 ng/mL | 7684 | 505 |
| 5 ng/mL | 7601 | 571 |
| 7 ng/mL | 7856 | 663 |
| 10 ng/mL | 7326 | 626 |
| 12 ng/mL | 7308 | 706 |
| 15 ng/mL | 7729 | 724 |
| 20 ng/mL | 6918 | 826 |
| 25 ng/mL | 7155 | 1167 |
| 30 ng/mL | 6280 | 945 |
| 35 ng/mL | 7338 | 1173 |
| 40 ng/mL | 6812 | 1172 |
| 45 ng/mL | 7866 | 1491 |
| 50 ng/mL | 7229 | 1492 |
| 75 ng/mL | 7406 | 1628 |
| 100 ng/mL | 6385 | 1572 |
| 200 ng/mL | 8014 | 2199 |
| 500 ng/mL | 6225 | 1943 |
| 1000 ng/mL | 6524 | 2229 |

These results demonstrated that the disclosed anti-BlaC antibodies and non-optimized lateral flow assay design can be used to successfully detect BlaC antigen in saliva at a concentration at least as low as 0.5 ng/mL.

X. The following describes ELISA assays demonstrating the use of antibody reagent pairings that successfully detect recombinant and purified wild-type BlaC, including additional assays to optimize antibody concentrations and other reaction parameters. The assays also demonstrate lack of cross-reactivity to other antigens (i.e., have high specificity for BlaC).

General ELISA Methods

Coating antibodies were diluted in sodium carbonate buffer (0.1 M Sodium Carbonate pH 9.5) to desired concentration and 100 uL were added to each well on a polycarbonate plate. The plate was incubated with the antibodies for 2 hours at 37° C. or overnight at 4° C. After incubation, the plate was washed 3× with PBS-Tw (1×PBS+0.1% Tween 20, pH 7.4). Antigen was diluted to the desired concentration with 1×PBS (pH 7.4). 100 uL of antigen was added to each well and incubated at 37° C. for 90 minutes. After incubation, the plate was washed 3× with PBS-Tw. The selected detection antibody diluted with PBS-Tw to desired concentration. 100 uL of the detection antibody was added to each well and incubated for 1 hour at 37° C. After incubation, the plates was washed 3× with PBS-Tw. The HRP-conjugated antibody was diluted to the desired titer with PBS-Tw. 100 uL was added to each well and incubated for 30 minutes at 37° C. After incubation, the plate was washed 2× with PBS-Tw, then another 2× with PBS. 100 uL of TMB substrate was added to each well and the plate was incubated in the dark for 10-15 minutes. 50 uL of IN sulfuric acid was added to stop the reaction. The plate was read at 450 nm with 630 nm as the reference wavelength.

Results

1) ELISA Pairing Mouse Anti-BlaC mAb and Anti-BlaC Goat Polyclonal or Anti-BlaC Rabbit IgG An initial screen was performed using 10 μg/mL Mouse anti-BlaC mAb (from clone G1, as described above in part VI) as the coating (i.e., capture antibody) and 10 μg/mL anti-BlaC goat polyclonal (obtained by affinity purification) or 10 μg/mL purified anti-BlaC rabbit IgG (polyclonal) as the detection antibody. The bound detection antibody was monitored using HRP-conjugated Ab at a titer of 1:8000 (rabbit) and 1:4000 (goat). It is noted that the original concentration of HRP-rabbit and HRP-mouse are twice that of HRP-goat, so titer for rabbit (or mouse) and goat is generally used at 2:1 ratio to adjust for this difference of concentration. BSA was used as a control. Recombinant BlaC (rBlaC) was produced as described above. Wild type BlaC was purified from 7H9 cultures at 3 μg/mL (as the initial wtBlaC purification). "Sauton" refers to the supernatant from the growth medium in which *M. tuberculosis* was cultured, whereas Sauton (Broth (−)) is a negative control medium with no *M. tuberculosis* cultured therein. Any positive or enhanced signal from the Sauton sample in contrast to the blank Sauton sample indicates the detection of wild-type BlaC excreted by the *M. tuberculosis* grown in the culture.

The results of the ELISA assays are set forth in Table 7.

TABLE 7

ELISA using Mouse anti-BlaC mAb (G1 clone) as capture antibody and either anti-BlaC goat polyclonal or purified anti-BlaC rabbit IgG as detection antibody for various antigens

| Antigen | Detection: Goat pAb | Detection: Rabbit pAb |
|---|---|---|
| 0.1% BSA | 0.883 | 0.139 |
| 0.1% BSA | 0.679 | 0.139 |
| rBlaC (100 ng/mL) | 1.43 | 1.493 |
| rBlaC (500 ng/mL) | 1.951 | 1.514 |
| wt BlaC (1:10 dilut) | 1.263 | 0.677 |
| wt BlaC (1:100 dilut) | 1.382 | 0.781 |
| Sauton (OD: 1.0) | 1.548 | 1.116 |
| Sauton (Broth (−)) | 0.926 | 0.151 |

These results demonstrate that the combination of Mouse anti-BlaC mAb (G1 clone) and either anti-BlaC goat polyclonal or anti-BlaC rabbit IgG antibodies is useful to detect both recombinant and wild-type BlaC. Furthermore, BlaC is detectable from the supernatant of *M. tuberculosis*, further indicating the utility of these reagents for the detection of TB-complex bacteria from a sample.

2) ELISA Pairing Anti-BlaC Rabbit IgG with Three Mouse Anti-BlaC mAbs

An expanded screen was performed using 10 μg/mL and 20 μg/mL of Mouse anti-BlaC mAb (from clone G1, H1, and 31A, as described above in part VI) as the coating ("C" i.e., capture antibody) and 10 μg/mL purified anti-BlaC rabbit polyclonal IgG Ab as the detection antibody ("D"). The bound detection antibody was monitored using HRP-conjugated Ab at a titer of 1:8000 (rabbit). BSA and Sauton (−) were used as controls. rBlaC, wtBlaC, and Sauton (BlaC+), as described above in part (1), were used as antigen.

The results of the ELISA assays are set forth in Table 8.

TABLE 8

ELISA pairing anti-BlaC rabbit IgG (D) with three Mouse anti-BlaC mAbs (C)

|  | D: 10 ug/mL C: G1 10 ug/mL | D: 10 ug/mL C: H1 10 ug/mL | D: 10 ug/mL C: 31A 10 ug/mL | D: 10 ug/mL C: G1 20 ug/mL | D: 10 ug/mL C: H1 20 ug/mL | D: 10 ug/mL C: 31A 20 ug/mL |
|---|---|---|---|---|---|---|
| 0.1% BSA | 0.905 | 1.139 | 0.912 | 0.946 | 1.26 | 0.902 |
| 0.1% BSA | 0.849 | 0.93 | 0.774 | 0.893 | 1.131 | 0.863 |
| rBlaC, 20 ng/mL | >3.0 | >3.0 | >3.0 | >3.0 | >3.0 | >3.0 |
| rBlaC, 50 ng/mL | >3.0 | >3.0 | >3.0 | >3.0 | >3.0 | >3.0 |
| wtBlaC, 1:10 dilut | 2.48 | 2.938 | 2.214 | 2.574 | >3.0 | 2.075 |
| wtBlaC, 1:100 dilut | 2.434 | >3.0 | 2.213 | 2.681 | 2.973 | 2.161 |
| Sauton (+), OD 1.0 | >3.0 | >3.0 | >3.0 | >3.0 | >3.0 | >3.0 |
| Sauton (−), Broth | 1.065 | 1.225 | 1.008 | 1.029 | 1.576 | 1.281 |

These results indicate that all three Mouse monoclonal antibodies (i.e., from clones G1, H1, and 31A) were effective in pairing with anti-BlaC rabbit IgG as a detection antibody for specifically detecting recombinant and wild-type BlaC as compared to BSA control. Furthermore, these reagents were effective in detecting BlaC in the growth medium from *M. tuberculosis* culture.

3) Antibody Titer Assay

An antibody titer assay was performed using varying amounts (10 μg/mL, 5 μg/mL, 2.5 μg/mL, and 1.25 μg/mL) of Mouse anti-BlaC mAb (from clone G1, as described above in part VI) as the coating ("C" i.e., capture antibody) and varying amounts (10 μg/mL, 5 μg/mL, and 2.5 μg/mL) of purified anti-BlaC rabbit IgG as the detection antibody ("D"). The bound detection antibody was monitored using HRP-conjugated Ab at a titer of 1:10,000 (rabbit). BSA and Sauton (−) were used as controls. rBlaC, wtBlaC, and Sauton (BlaC+), as described above in part (1), were used as antigen.

The results of the ELISA assays are set forth in Table 9.

TABLE 9

ELISA titer assay using varying amounts of Mouse anti-BlaC mAb (C) and anti-BlaC rabbit IgG (D)

| | 0.1% BSA | 0.1% BSA | rBlaC, 20 ng/mL | rBlaC, 50 ng/mL | wtBlaC, 1:10 dilut | wtBlaC, 1:100 dilut | Sauton (+), OD 1.0 | Sauton (−), Broth |
|---|---|---|---|---|---|---|---|---|
| D: 10 ug/m C: 10 ug/mL | 0.728 | 0.794 | >3.0 | >3.0 | 2.263 | 2.256 | >3.0 | 0.978 |
| D: 5 ug/mL C: 10 ug/mL | 0.498 | 0.502 | >3.0 | >3.0 | 1.556 | 1.616 | >3.0 | 0.605 |
| D: 2.5 ug/mL C: 10 ug/mL | 0.313 | 0.319 | >3.0 | >3.0 | 1.022 | 1.008 | >3.0 | 0.361 |
| D: 10 ug/mL C: 5 ug/mL | 0.755 | 0.679 | >3.0 | >3.0 | 2.138 | 2.189 | >3.0 | 0.922 |
| D: 5 ug/mL C: 5 ug/mL | 0.548 | 0.412 | >3.0 | >3.0 | 1.398 | 1.573 | >3.0 | 0.597 |
| D: 2.5 ug/mL C: 5 ug/mL | 0.305 | 0.268 | >3.0 | >3.0 | 0.968 | 0.959 | >3.0 | 0.394 |
| D: 10 ug/mL C: 2.5 ug/mL | 0.763 | 0.654 | >3.0 | >3.0 | 2.189 | 2.249 | >3.0 | 0.809 |
| D: 5 ug/mL C: 2.5 ug/mL | 0.443 | 0.395 | >3.0 | >3.0 | 1.33 | 1.212 | >3.0 | 0.57 |
| D: 2.5 ug/mL C: 2.5 ug/mL | 0.243 | 0.265 | >3.0 | >3.0 | 0.85 | 0.798 | 2.854 | 0.322 |
| D: 10 ug/mL C: 1.25 ug/mL | 0.582 | 0.56 | >3.0 | >3.0 | 1.368 | 1.691 | >3.0 | 0.727 |
| D: 5 ug/mL C: 1.25 ug/mL | 0.341 | 0.294 | >3.0 | >3.0 | 0.795 | 0.812 | >3.0 | 0.471 |
| D: 2.5 ug/mL C: 1.25 ug/mL | 0.182 | 0.178 | 2.877 | >3.0 | 0.449 | 0.468 | 2.189 | 0.272 |

These results demonstrate that even at the lowest tested antibody concentrations for both the capture (coating) and detection antibodies (see column 12), the ELISA assay was able to specifically detect recombinant and wild-type BlaC.

4) Antibody Titer Assay, Continued

A further antibody titer assay was performed using varying amounts (0.6 μg/mL, 0.3 μg/mL, and 0.15 μg/mL) of Mouse anti-BlaC mAb (from clones G1, H1, and 31A, as described above in part VI) as the coating ("C" i.e., capture antibody) and 2.5 μg/mL of purified anti-BlaC rabbit IgG polyclonal Ab as the detection antibody ("D"). The bound detection antibody was monitored using HRP-conjugated Ab at a titer of 1:12,000 (rabbit). PBS, BSA and Sauton (−) were used as controls. rBlaC, and Sauton (BlaC+), as described above in part (1), were used as antigen.

The results of the ELISA assays are set forth in Table 10.

able to specifically detect BlaC over blank and irrelevant protein controls.

5) Antibody Titer Assay, Continued

A further antibody titer assay was performed using varying amounts (0.6 μg/mL and 0.3 μg/mL) of Mouse anti-BlaC mAb (from clones G1, H1, and 31A, as described above in part VI) as the coating ("C" i.e., capture antibody) and 2.5 μg/mL of purified anti-BlaC Goat or rabbit anti-BlaC serum (polyclonal serum at 8 week post-immunization) as the detection antibody ("D"). The bound detection antibody was monitored using HRP-conjugated Ab at a titer of 1:10,000 (rabbit) or 1:5,000 (goat). PBS, BSA and Sauton (−) were

TABLE 10

ELISA titer assay using varying amounts of Mouse anti-BlaC mAb (C) and 2.5 μg/mL of purified anti-BlaC rabbit IgG polyclonal Ab as the detection antibody (D)

|  | PBS-T | PBS-T | 0.1% BSA | 0.1% BSA | rBlaC 2 ng/mL | rBlaC 5 ng/mL | Sauton (+), OD 1.0 | Sauton (−), Broth |
|---|---|---|---|---|---|---|---|---|
| C: G1 0.6 ug/mL | 0.128 | 0.148 | 0.104 | 0.098 | 0.208 | 0.23 | 1.504 | 0.155 |
| C: H1 0.6 ug/mL | 0.159 | 0.164 | 0.134 | 0.107 | 0.288 | 0.496 | 1.53 | 0.156 |
| C: 31A 0.6 ug/mL | 0.161 | 0.204 | 0.104 | 0.092 | 0.266 | 0.363 | 1.461 | 0.16 |
| C: G1 0.3 ug/mL | 0.106 | 0.108 | 0.088 | 0.088 | 0.164 | 0.217 | 1.843 | 0.12 |
| C: H1 0.3 ug/mL | 0.135 | 0.124 | 0.11 | 0.097 | 0.165 | 0.261 | 1.68 | 0.125 |
| C: 31A 0.3 ug/mL | 0.121 | 0.12 | 0.085 | 0.084 | 0.18 | 0.248 | 1.657 | 0.147 |
| C: G1 0.15 ug/mL | 0.098 | 0.105 | 0.075 | 0.071 | 0.134 | 0.196 | 1.526 | 0.089 |
| C: H1 0.15 ug/mL | 0.095 | 0.1 | 0.093 | 0.073 | 0.171 | 0.214 | 1.484 | 0.203 |
| C: 31A 0.15 ug/mL | 0.096 | 0.095 | 0.067 | 0.068 | 0.161 | 0.209 | 1.527 | 0.12 |

These results demonstrate that even at the lowest tested antibody concentrations for both the capture (coating) and detection antibodies (see column 12), the ELISA assay was used as controls. rBlaC, wtBlaC, and Sauton (BlaC+), as described above in part (1), were used as antigen.

The results of the ELISA assays are set forth in Table 11.

TABLE 11

ELISA titer assay using varying amounts of Mouse anti-BlaC mAb from clones G1, H1, and 31A (C) and 2.5 ug/mL of purified anti-BlaC Goat or rabbit anti-BlaC serum as the detection antibody (D)

|  | PBS-T | PBS-T | 0.1% BSA | 0.1% BSA | rBlaC 2 ng/mL | rBlaC 5 ng/mL | Sauton (+), OD 1.0 | Sauton (−), Broth |
|---|---|---|---|---|---|---|---|---|
| D: Goat; C: G1 (0.6 μg/mL) | 2.416 | 2.42 | 1.513 | 1.779 | 2.413 | 2.444 | 2.179 | 2.201 |
| D: Goat; C: H1 (0.6 μg/mL) | >3.0 | >3.0 | 2.374 | 2.403 | >3.0 | >3.0 | >3.0 | >3.0 |
| D: Goat; C: 31A (0.6 μg/mL) | 2.009 | 2.019 | 1.351 | 1.275 | 1.936 | 1.909 | 1.868 | 1.837 |
| D: Goat; C: G1 (0.3 μg/mL) | 1.453 | 1.352 | 0.941 | 0.892 | 1.292 | 1.403 | 1.432 | 1.247 |
| D: Goat; C: H1 (0.3 μg/mL) | 1.634 | 1.892 | 1.111 | 1.161 | 1.648 | 1.814 | 1.661 | 1.674 |
| D: Goat; C: 31A (0.3 μg/mL) | 1.05 | 1.01 | 0.701 | 0.742 | 1.058 | 1.238 | 1.136 | 1.022 |
| D: Rab; C: G1 (0.6 μg/mL) | 0.375 | 0.362 | 0.16 | 0.199 | 0.402 | 0.457 | 0.626 | 0.357 |
| D: Rab; C: H1 (0.6 μg/mL) | 0.397 | 0.397 | 0.209 | 0.188 | 0.438 | 0.647 | 1.441 | 0.402 |

TABLE 11-continued

ELISA titer assay using varying amounts of Mouse anti-BlaC mAb from clones
G1, H1, and 31A (C) and 2.5 ug/mL of purified anti-BlaC Goat or rabbit anti-BlaC serum
as the detection antibody (D)

|  | PBS-T | PBS-T | 0.1% BSA | 0.1% BSA | rBlaC 2 ng/mL | rBlaC 5 ng/mL | Sauton (+), OD 1.0 | Sauton (−), Broth |
|---|---|---|---|---|---|---|---|---|
| D: Rab; C: 31A (0.6 µg/mL) | 0.34 | 0.309 | 0.215 | 0.214 | 0.411 | 0.449 | 0.629 | 0.37 |
| D: Rab; C: G1 (0.3 µg/mL) | 0.358 | 0.364 | 0.155 | 0.165 | 0.402 | 0.409 | 0.553 | 0.401 |
| D: Rab; C: H1 (0.3 µg/mL) | 0.461 | 0.556 | 0.252 | 0.224 | 0.796 | 0.925 | 0.627 | 0.652 |
| D: Rab; C: 31A (0.3 µg/mL) | 0.216 | 0.339 | 0.181 | 0.151 | 0.378 | 0.343 | 0.544 | 0.269 |

These results demonstrate that some combinations of the capture and detection antibodies (i.e., anti-BlaC Goat or rabbit anti-BlaC serum), at the lowest tested antibody concentrations retained the ability to specifically detect BlaC over blank and irrelevant protein controls. However, other combinations were unable to reliably provide a noticeable detectable signal improvement over the controls.

6) ELISA Assay Using Mouse Anti-BlaC mAb and Low HRP Titer

An ELISA assay was performed using varying amounts (0.15 µg/mL and 0.075 µg/mL) of Mouse anti-BlaC mAb (from clones G1, H1, and 31A, as described above in part VI) as the coating ("C" i.e., capture antibody) and 2.5 µg/mL of purified anti-BlaC rabbit IgG polyclonal Ab as the detection antibody ("D"). The bound detection antibody was monitored using HRP-conjugated Ab at a titer of 1:9,000 (rabbit). PBS, BSA and Sauton (−) were used as controls. rBlaC, wtBlaC, and Sauton (BlaC+), as described above in part (1), were used as antigen.

The results of the ELISA assays are set forth in Table 12.

As illustrated in Table 12, the decreasing levels of BlaC in the Sauton antigen were still detectable using all of the antibody combinations over the blank Sauton antigen control until the antigen-positive Sauton mixture reached $10^3$ CFU/ml. Furthermore, these results generally demonstrate that most combinations of the capture and detection antibodies, even at the lowest tested concentrations, retained the ability to specifically detect BlaC over blank and irrelevant protein controls. However, other combinations were unable to reliably provide a noticeable detectable signal improvement over the controls.

7) ELISA Assay Using Mouse Anti-BlaC mAb Paired with and 2.5 µg/mL of Purified Anti-BlaC Rabbit IgG An ELISA assay was performed using varying amounts (0.15 µg/mL and 0.075 µg/mL) of Mouse anti-BlaC mAb (from clones G1, H1, and 31A, as described above in part VI) as the coating ("C" i.e., capture antibody) and 2.5 µg/mL of purified anti-BlaC rabbit IgG polyclonal Ab as the detection antibody ("D"). The bound detection antibody was monitored using HRP-conjugated Ab at a titer of 1:12,000

TABLE 12

ELISA titer assay using varying amounts of Mouse anti-BlaC mAb from clones
G1, H1, and 31A (C) and 2.5 µg/mL of purified anti-BlaC rabbit IgG as the detection
antibody (D)

| Antigen | C: G1 0.15 ug/mL | C: H1 0.15 µg/mL | C: 31A 0.15 µg/mL | C: G1 0.075 µg/mL | C: H1 0.075 µg/mL | C: 31A 0.075 µg/mL |
|---|---|---|---|---|---|---|
| PBS-T | 0.327 | 0.176 | 0.18 | 0.176 | 0.22 | 0.166 |
| PBS-T | 0.183 | 0.157 | 0.186 | 0.176 | 0.318 | 0.204 |
| 0.1% BSA | 0.141 | 0.13 | 0.125 | 0.144 | 0.239 | 0.156 |
| 0.1% BSA | 0.141 | 0.124 | 0.132 | 0.189 | 0.162 | 0.186 |
| rBlaC 5 ng/mL | 0.396 | .0449 | 0.385 | 0.193 | 0.436 | 0.387 |
| rBlaC 2 ng/mL | 0.296 | 0.244 | 0.214 | 0.391 | 0.241 | 0.21 |
| rBlaC 1 ng/mL | 0.195 | 0.231 | 0.206 | 0.245 | 0.321 | 0.18 |
| Sauton (+), OD 0.8 | 2.561 | 2.737 | 2.743 | 0.204 | 2.916 | 2.561 |
| Sauton (+), OD 0.5 or ~$10^7$ CFU/ml | 0.983 | 1.243 | 1.122 | 2.741 | 1.138 | 1.096 |
| Sauton (+), $10^5$ CFU/ml | 0.242 | 0.194 | 0.199 | 1.298 | 0.306 | 0.151 |
| Sauton (+), $10^3$ CFU/ml | 0.156 | 0.172 | 0.152 | 0.159 | 0.196 | 0.138 |
| Sauton (−), Broth | 0.197 | 0.168 | 0.169 | 0.174 | 0.158 | 0.15 |

(rabbit). PBS, BSA and Sauton (−) were used as controls. rBlaC, wtBlaC, and Sauton (BlaC+), as described above in part (1), were used as antigen.

The results of the ELISA assays are set forth in Table 13.

TABLE 13

ELISA titer assay using varying amounts of Mouse anti-BlaC mAb from clones G1, H1, and 31A (C) and 2.5 ug/mL of purified anti-BlaC rabbit IgG as the detection antibody (D)

| Antigen | C: G1 0.15 ug/mL | C: H1 0.15 μg/mL | C: 31A 0.15 μg/mL | C: G1 0.075 μg/mL | C: H1 0.075 μg/mL | C: 31A 0.075 μg/mL |
|---|---|---|---|---|---|---|
| PBS-T | 0.115 | 0.152 | 0.15 | 0.16 | 0.152 | 0.209 |
| PBS-T | 0.132 | 0.151 | 0.129 | 0.15 | 0.165 | 0.164 |
| 0.1% BSA | 0.086 | 0.109 | 0.118 | 0.113 | 0.122 | 0.466 |
| 0.1% BSA | 0.085 | 0.126 | 0.085 | 0.13 | 0.164 | 0.152 |
| rBlaC 5 ng/mL | 0.275 | 0.285 | 0.275 | 0.247 | 0.424 | 0.279 |
| rBlaC 2 ng/mL | 0.216 | 0.198. | 0.173 | 0.181 | 0.193 | 0.182 |
| rBlaC 1 ng/mL | 0.164 | 0.17 | 0.154 | 0.157 | 0.15 | 0.145 |
| Sauton (+), OD 0.8 | 1.738 | 1.561 | 2.003 | 2.095 | 1.806 | 2.801 |
| Sauton (+), OD 0.5 or ~$10^7$ CFU/ml | 0.761 | 0.692 | 0.709 | 0.922 | 0.874 | 0.984 |
| Sauton (+), 10 CFU/ml | 0.131 | 0.2 | 0.162 | 0.124 | 0.284 | 0.143 |
| Sauton (+), 103 CFU/ml | 0.135 | 0.131 | 0.156 | 0.127 | 0.247 | 0.121 |
| Sauton (−), Broth | 0.154 | 0.151 | 0.161 | 0.149 | 0.133 | 0.14 |

As illustrated in Table 13, the decreasing levels of BlaC in the Sauton antigen were still detectable using all of the antibody combinations over the blank Sauton antigen control until the antigen-positive Sauton mixture reached $10^3$ CFU/ml. However, it is noted that the BlaC antigen was still detectable in the most dilute BlaC-positive Sauton antigen using the H1 Mouse mAb as the capture reagent. Furthermore, these results demonstrate that some combinations of the capture and detection antibodies, even at the lowest tested antibody concentrations, retained the ability to specifically detect BlaC over blank and irrelevant protein controls. However, other combinations were unable to reliably provide a noticeable detectable signal improvement over the controls.

Figure 13:
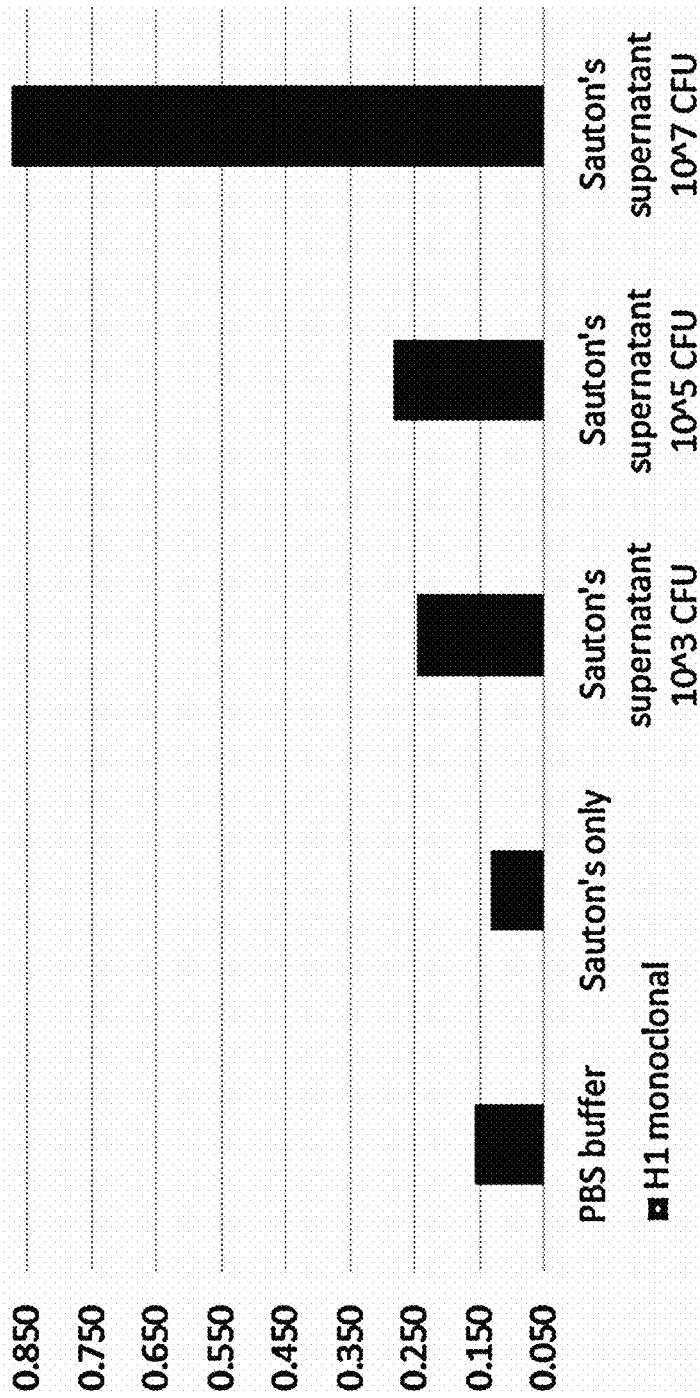
FIG. 13 graphically illustrates an exemplary primer pair, namely Mouse anti-BlaC H1 mAb as capture antibody and purified anti-BlaC rabbit (polyclonal) IgG as detection antibody, that successfully detected the presence of BlaC from the Sauton's medium supernatant from a culture of varying densities of *Mycobacterium tuberculosis*. Samples of PBS buffer and Sauton's medium only were used as controls.
Figure 14:
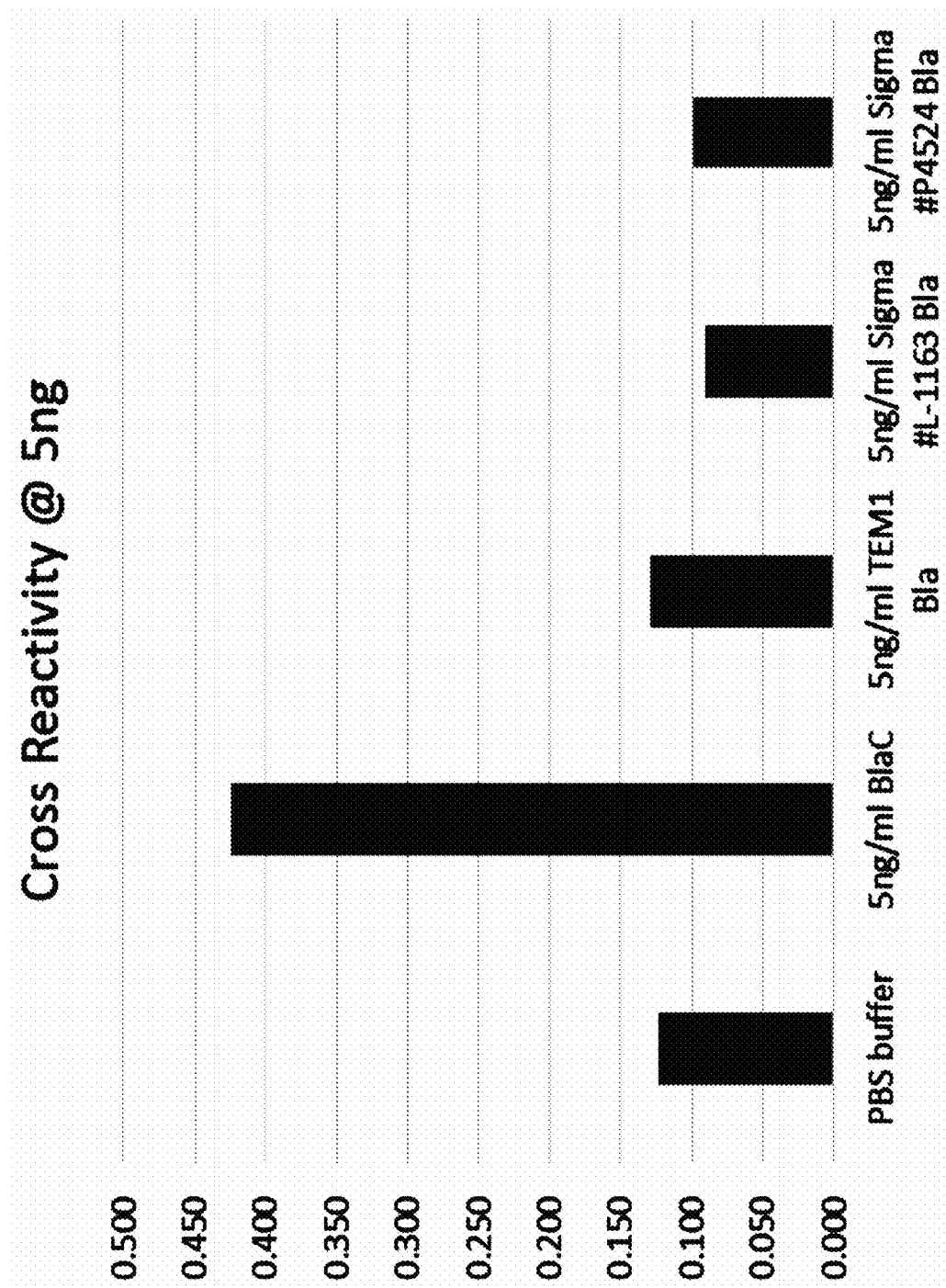
FIG. 14 graphically illustrates the lack of cross reactivity between the disclosed anti-BlaC reagents and related, non TB-complex β lactamase proteins.
Figure 15:
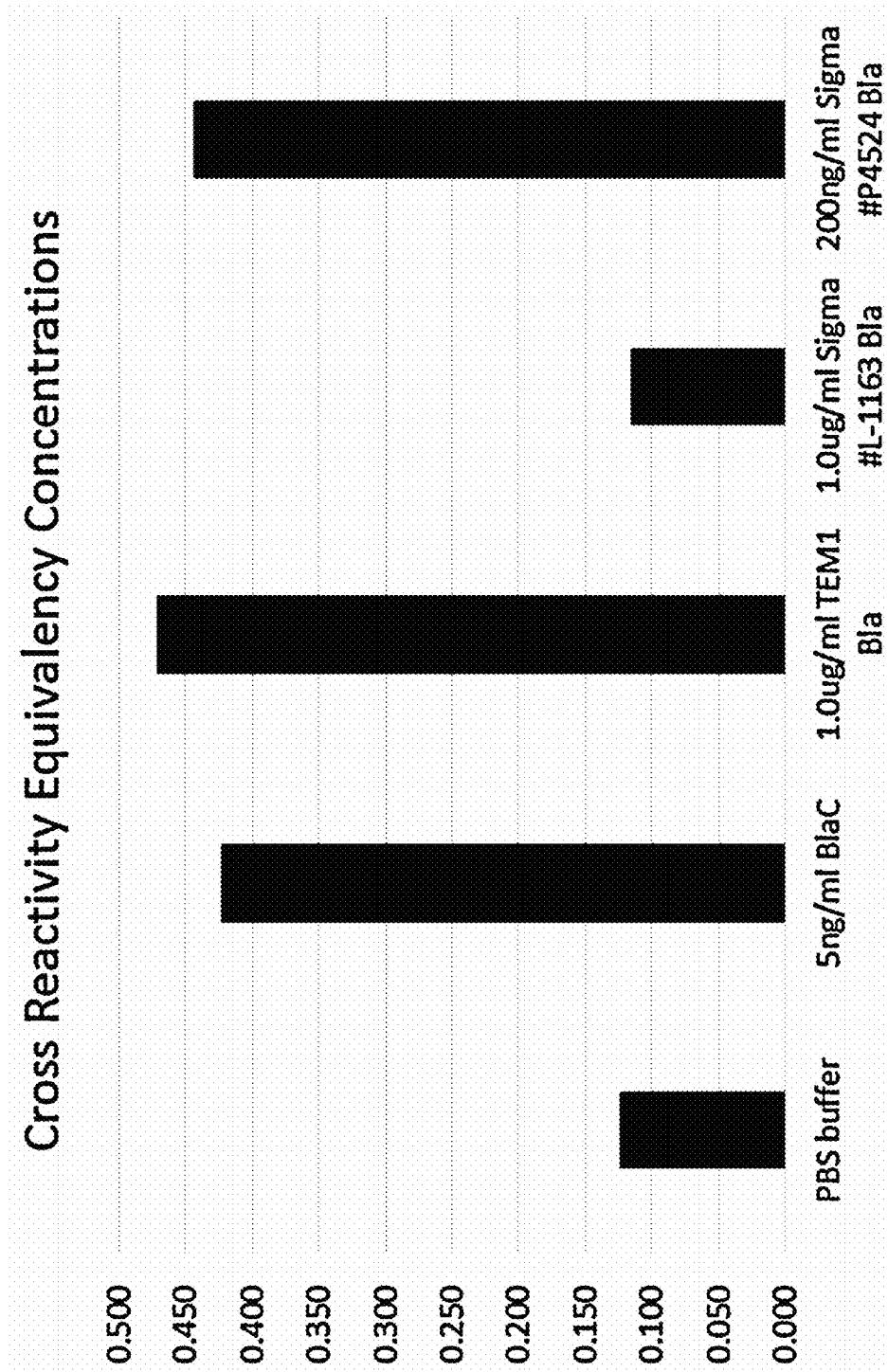
FIG. 15 graphically illustrates the amount of non TB-complex β lactamase proteins required to produce an equivalent signal to 5 ng/mL BlaC.

Furthermore, FIG. 13 graphically illustrates the signal intensity for the Mouse anti-BlaC H1 mAb in detecting the BlaC present in the negative controls as compared to the BlaC positive Sauton antigen samples. As indicated in the graph, the combination of the H1 mAb with the purified anti-BlaC rabbit (polyclonal) IgG detection antibody provided a good difference between negative control and the minimal presence (i.e., $10^3$ CFU) of M. tuberculosis in the Sauton's culture medium. This contributes to the other assay results, which in combination indicate that at least 11 different pairs from three monoclonal antibodies and four polyclonal antibodies can provide sensitive detection of wild-type and recombinant BlaC.

8) ELISA Assay Using Mouse Anti-BlaC Paired with and 1.0 μg/mL of Affinity Purified Anti-BlaC Goat Polyclonal Ab An ELISA assay was performed using varying amounts (0.15 μg/mL and 0.075 μg/mL) of Mouse anti-BlaC mAb (from clones G1, H1, and 31A, as described above in part VI) as the coating ("C" i.e., capture antibody) and 1.0 μg/mL of Goat affinity purified anti-BlaC (affinity purified) polyclonal antibody as the detection antibody ("D"). The bound detection antibody was monitored using HRP-conjugated Ab at a titer of 1:12,000 (rabbit). PBS, BSA and Sauton (−) were used as controls. rBlaC, wtBlaC, and Sauton (BlaC+), as described above in part (1), were used as antigen.

The results of the ELISA assays are set forth in Table 14.

TABLE 14

ELISA titer assay using varying amounts of Mouse anti-BlaC mAb from clones G1, H1, and 31A (C) and 1.0 ug/mL of affinity purified anti-BlaC Goat polyclonal as the detection antibody (D)

| Antigen | C: G1 0.15 ug/mL | C: H1 0.15 μg/mL | C: 31A 0.15 μg/mL | C: G1 0.075 μg/mL | C: H1 0.075 μg/mL | C: 31A 0.075 μg/mL |
|---|---|---|---|---|---|---|
| PBS-T | 0.42 | 0.461 | 0.332 | 0.227 | 0.237 | 0.249 |
| PBS-T | 0.446 | 0.482 | 0.349 | 0.262 | 0.224 | 0.203 |
| 0.1% BSA | 0.34 | 0.33 | 0.24 | 0.16 | 0.167 | 0.146 |
| 0.1% BSA | 0.333 | 0.33 | 0.258 | 0.159 | 0.182 | 0.139 |
| rBlaC 1 ng/mL | 0.587 | 0.65 | 0.53 | 0.91 | 0.481 | 0.411 |
| rBlaC 2 ng/mL | 0.73 | 0.869 | 0.798 | 0.644 | 0.683 | 0.609 |

TABLE 14-continued ELISA titer assay using varying amounts of Mouse anti-BlaC mAb from clones
G1, H1, and 31A (C) and 1.0 ug/mL of affinity purified anti-BlaC Goat polyclonal as the
detection antibody (D)

| Antigen | C: G1 0.15 ug/mL | C: H1 0.15 µg/mL | C: 31A 0.15 µg/mL | C: G1 0.075 µg/mL | C: H1 0.075 µg/mL | C: 31A 0.075 µg/mL |
|---|---|---|---|---|---|---|
| rBlaC 5 ng/mL | 0.137 | 1.341 | 1.307 | 1.198 | 1.222 | 1.235 |
| Sauton (+), OD 0.8 | 1.164 | 1.636 | 1.132 | 1.174 | 1.088 | 1.559 |
| Sauton (+), OD 0.5 or ~$10^7$ CFU/ml | 0.71 | 0.718 | 0.77 | 0.766 | 0.598 | 0.628 |
| Sauton (+), $10^5$ CFU/ml | 0.586 | 0.384 | 0.311 | 0.21 | 0.224 | 0.18 |
| Sauton (+), $10^3$ CFU/ml | 0.365 | 0.405 | 0.3 | 0.204 | 0.215 | 0.356 |
| Sauton (−), Broth | 0.408 | 0.414 | 0.295 | 0.195 | 0.196 | 0.17 |

As illustrated in Table 14, the decreasing levels of BlaC in the Sauton medium were still detectable using all of the antibody combinations (with the capture antibody at 0.075 µg/mL) over the blank Sauton antigen control. Interestingly, when the capture antibodies were coated at the higher concentration, the lowest Sauton (+) signal was indistinguishable from the blank Sauton medium. Furthermore, all combinations of the capture and detection antibodies, even at the lowest tested concentrations, retained the ability to specifically detect the lowest levels of rBlaC over blank and irrelevant protein controls.

9) ELISA Assay Using Mouse Anti-BlaC mAb as Detection Antibodies Paired with Various Polyclonal Antibodies as Capture Reagent An ELISA assay was performed using 0.15 µg/mL various anti-BlaC polyclonal antibodies (i.e., affinity purified goat, purified goat IgG, rabbit serum ("A&M"; 8-week post immunization bleed), and rabbit Abcam) as the coating ("C" i.e., capture antibody) and 2.5 µg/mL of Mouse anti-BlaC mAb (from clones G1, H1, and 31A, as described above in part VI) as the detection antibody ("D"). The bound detection antibody was monitored using HRP-conjugated Ab at a titer of 1:12,000 (mouse). PBS, BSA and Sauton (−) were used as controls. rBlaC, wtBlaC, and Sauton (BlaC+), as described above in part (1), were used as antigen.

The results of the ELISA assays are set forth in Table 15.

TABLE 15

ELISA titer assay using 2.5 ug/mL of Mouse anti-BlaC mAb from clones G1, H1, and
31A (D) and 0.15 ug/mL of various anti-BlaC polyclonal reagents as the
detection antibody (C)

| | PBS-T | PBS-T | 0.1% BSA | 0.1% BSA | rBlaC 5 ng/mL | rBlaC 2 ng/mL | Sauton (+), OD 0.8 | Sauton (−), Broth |
|---|---|---|---|---|---|---|---|---|
| D: Goat Aff C: G1 | 0.074 | 0.086 | 1.627 | 1.78 | 1.912 | 0.879 | 0.634 | 0.071 |
| D: Goat IgG C: G1 | 0.106 | 0.092 | 1.768 | 1.85 | 1.85 | 0.953 | 0.609 | 0.136 |
| D: A&M rab C: G1 | 0.087 | 0.089 | 1.617 | 1.661 | 1.793 | 0.885 | 0.646 | 0.077 |
| D: Abcam rab C: G1 | 0.09 | 0.081 | 1.668 | 1.851 | 2.03 | 0.939 | 0.604 | 0.076 |
| D: Goat Aff C: H1 | 0.1074 | 0.12 | 0.399 | 0.422 | 1.599 | 0.712 | 0.599 | 0.172 |
| D: Goat IgG C: H1 | 0.138 | 0.103 | 0.364 | 0.384 | 1.426 | 0.64 | 0.399 | 0.114 |
| D: A&M rab C: H1 | 0.1 | 0.103 | 0.352 | 0.381 | 1.426 | 0.67 | 0.373 | 0.109 |
| D: Abcam rab C: H1 | 0.11 | 0.099 | 0.366 | 0.36 | 1.523 | 0.729 | 0.441 | 0.111 |
| D: Goat Aff C: 31A | 0.17 | 0.17 | >3.0 | >3.0 | 0.68 | 0.402 | 0.387 | 0.181 |
| D: Goat IgG C: 31A | 0.139 | 0.135 | >3.0 | >3.0 | 0.521 | 0.353 | 0.395 | 0.149 |
| D: A&M rab C: 31A | 0.133 | 0.135 | >3.0 | >3.0 | 0.482 | 0.315 | 0.405 | 0.127 |
| D: Abcam rab C: 31A | 0.144 | 0.147 | >3.0 | >3.0 | 0.553 | 0.331 | 0.495 | 0.144 |

As illustrated in Table 15, all assays incorporating a Mouse anti-BlaC monoclonal antibody as a detection antibody in combination with a polyclonal reagent as the capture antibody provided significantly higher BlaC signal in the BlaC (+) Sauton's medium and BlaC antigen groups over the blank Sauton medium and PBS control. This demonstrates, in connection with the above assays, that the monoclonal antibodies are useful in a variety of formats including when used as immobilized capture reagents or as detection reagents that can flow across a strip.

10) ELISA Cross-Reactivity Assay Comparing ELISA Detection of BlaC and Non TB-Complex β-Lactamases To test the cross reactivity of an assay using effective detection and capture reagents, the best concentration conditions from part (7), above, were used. Mouse anti-BlaC monoclonal antibodies from clones G1, H1, and 31A were used as the coat (i.e., "capture" (C)) reagent in ranges from 0.15 to 0.075 μg/mL. Purified anti-IgG rabbit polyclonal reagent was used as the detection antibody ("D") at 2.5 μg/mL. Any bound detection antibody was quantified using HRP-conjugated Ab at a titer of 1:12,000 (rabbit). Assays were run for TEM-1, a non TB-complex β-lactamase (Texas A&M University) produced from *E. coli*, a non TB-complex β-lactamase Type II (Sigma), and a non TB-complex β-lactamase Type IV from *Enterobacter cloacae* (Sigma). Specifically, the three non TB-complex β-lactamases were each applied at concentrations of 1 μg/mL, 500 ng/mL, 200 ng/mL, 100 ng/mL, 50 ng/mL, 20 ng/mL 10 ng/mL, and 5 ng/mL. Tests were conducted in PBS using the non-optimized ELISA formats otherwise described above.

The results were compared with the prior results obtained from *M. tuberculosis* (i.e., TB complex BlaC) in equivalent ELISA conditions. No cross reactivity of the assay (incorporating Mouse anti-BlaC mAbs and purified rabbit IgG anti-Blac polyclonal reagent) was observed for any of the non TB-complex β-lactamase. FIG. 14 graphically illustrates a representative comparison of signal observed for the different β-lactamase antigens (or PBS control) when applied at 5 ng/mL. The TB-complex BlaC provided a signal about four times background signal, whereas the non TB-complex β-lactamase did not differ from background. Comparison to the non TB-complex β-lactamases was performed to ascertain likelihood of any false positive signals and, thus, the utility of a TB diagnostic assay based on the disclosed reagents. However, it is uncertain which, or how much, if any of the β-lactamases from non TB complex bacteria might ever be present in the sputum or other biological sample obtained from a subject suspected of an infection. Accordingly, to demonstrate the amounts of the tested non TB-complex β-lactamases needed to equate to a 5 ng signal of BlaC, the maximum amount of the non TB-complex β-lactamases that produced an equivalent signal with the indicated ELISA format are represented graphically in FIG. 15. It is noted that the signal for β-lactamase Type II represents the maximum amount tested and yet still did not produce an "equivalent" signal, re-affirming a complete lack of functional cross-reactivity.

11) ELISA Optimization Assay: Mouse Anti-BlaC mAb (G1) and Amount of rBlaC Antigen An optimization ELISA was performed using from 2 μg/mL to 0.075 μg/mL Mouse anti-BlaC mAb (from clone G1, as described above in part VI) as the coating ("C" i.e., capture antibody) and 2.5 μg/mL purified rabbit anti-BlaC polyclonal Ab as the detection antibody ("D"). The bound detection antibody was monitored using HRP-conjugated Ab at a titer of 1:12,000 (rabbit). PBS and 0.25 ng/mL to 20 ng/mL recombinant BlaC, generated as described above, were used as antigen. Each antigen condition was run in duplicate.

The results of the ELISA optimization assay are set forth in Table 16.

TABLE 16

ELISA assessing titers of Mouse anti-BlaC mAb from clone G1 (C) paired with 2.5 μg/mL purified rabbit anti-BlaC polyclonal antibody as the detection antibody (D) with indicated amounts of rBlaC antigen.

| | C: 2 μg | C: 1 μg | C: 0.6 μg | C: 0.3 μg | C: 0.15 μg | C: .075 μg |
|---|---|---|---|---|---|---|
| PBS | 0.44 | 0.436 | 0.289 | 0.333 | 0.275 | 0.217 |
| PBS | 0.432 | 0.462 | 0.343 | 0.404 | 0.287 | 0.245 |
| rBlaC 0.25 ng/mL | 0.473 | 0.386 | 0.354 | 0.319 | 0.282 | 0.252 |
| rBlaC 0.25 ng/mL | 0.435 | 0.417 | 0.435 | 0.33 | 0.306 | 0.28 |
| rBlaC 0.5 ng/mL | 0.521 | 0.467 | 0.42 | 0.337 | 0.325 | 0.278 |
| rBlaC 0.5 ng/mL | 0.56 | 0.492 | 0.402 | 0.322 | 0.309 | 0.27 |
| rBlaC 1 ng/mL | 0.722 | 0.514 | 0.406 | 0.34 | 0.359 | 0.282 |
| rBlaC 1 ng/mL | 0.684 | 0.571 | 0.44 | 0.398 | 0.353 | 0.709 |
| rBlaC 2.5 ng/mL | 0.959 | 0.872 | 0.617 | 0.464 | 0.541 | 0.408 |
| rBlaC 2.5 ng/mL | 0.914 | 0.775 | 0.588 | 0.464 | 0.438 | 0.359 |
| rBlaC 5 ng/mL | 1.554 | 1.339 | 0.962 | 0.742 | 0.709 | 0.564 |
| rBlaC 5 ng/mL | 1.532 | 0.481 | 0.903 | 0.729 | 0.666 | 0.593 |
| rBlaC 10 ng/mL | >3 | 2.638 | 1.425 | 0.734 | 0.466 | 0.385 |
| rBlaC 10 ng/mL | >3 | 2.565 | 1.14 | 0.801 | 0.471 | 0.395 |
| rBlaC 20 ng/mL | >3 | >3 | 2.941 | 2.451 | 2.434 | 2.099 |
| rBlaC 20 ng/mL | >3 | >3 | >3 | 2.48 | 2.307 | 1.855 |

Table 16 illustrates the signal resulting from varying levels of capture antibody (Mouse anti-BlaC mAb from clone G1) and varying amounts of antigen.

12) ELISA Optimization Assay: Mouse Anti-BlaC mAb (H1) and Amount of rBlaC Antigen An optimization ELISA was performed using from 2 μg/mL to 0.075 μg/mL Mouse anti-BlaC mAb (from clone G1, as described above in part VI) as the coating ("C" i.e., capture antibody) and 2.5 μg/mL purified rabbit anti-BlaC polyclonal antibody as the detection antibody ("D"). The bound detection antibody was monitored using HRP-conjugated Ab at a titer of 1:12,000 (rabbit). PBS and 0.25 ng/mL to 20 ng/mL recombinant BlaC, generated as described above, were used as antigen. Each antigen condition was run in duplicate.

The results of the ELISA optimization assay are set forth in Table 17.

TABLE 17

ELISA assessing titers of Mouse anti-BlaC mAb from clone H1 as the capture antibody (C) paired with 2.5 µg/mL purified rabbit anti-BlaC polyclonal antibody as the detection antibody (D) with indicated amounts of rBlaC antigen.

|  | C: 2 µg | C: 1 µg | C: 0.6 µg | C: 0.3 µg | C: 0.15 µg | C: .075 µg |
|---|---|---|---|---|---|---|
| PBS | 0.598 | 0.56 | 0.456 | 0.36 | 0.261 | 0.244 |
| PBS | 0.547 | 0.516 | 0.421 | 0.308 | 0.295 | 0.85 |
| rBlaC 0.25 ng/mL | 0.612 | 0.539 | 0.422 | 0.321 | 0.329 | 0.24 |
| rBlaC 0.25 ng/mL | 0.645 | 0.615 | 0.446 | 0.49 | 0.356 | 0.228 |
| rBlaC 0.5 ng/mL | 0.639 | 0.595 | 0.439 | 0.315 | 0.308 | 0.288 |
| rBlaC 0.5 ng/mL | 0.709 | 0.601 | 0.415 | 0.503 | 0.312 | 0.293 |
| rBlaC 1 ng/mL | 0.738 | 0.696 | 0.495 | 0.335 | 0.257 | 0.27 |
| rBlaC 1 ng/mL | 0.704 | 0.736 | 0.505 | 0.328 | 0.327 | 0.282 |
| rBlaC 2.5 ng/mL | 1.072 | 1.056 | 0.774 | 0.548 | 0.405 | 0.385 |
| rBlaC 2.5 ng/mL | 1.08 | 1.095 | 0.757 | 0.463 | 0.433 | 0.394 |
| rBlaC 5 ng/mL | 1.674 | 1.668 | 1.177 | 0.707 | 0.646 | 0.592 |
| rBlaC 5 ng/mL | 1.789 | 1.688 | 1.177 | 0.705 | 0.629 | 0.553 |
| rBlaC 10 ng/mL | >3 | >3 | 2.311 | 0.893 | 0.554 | 0.37 |
| rBlaC 10 ng/mL | >3 | >3 | 2.487 | 0.752 | 0.495 | 0.375 |
| rBlaC 20 ng/mL | >3 | >3 | >3 | 2.428 | 2.06 | 1.715 |
| rBlaC 20 ng/mL | >3 | >3 | >3 | 2.606 | 1.928 | 1.526 |

Table 17 illustrates the signal resulting from varying levels of capture antibody (Mouse anti-BlaC mAb from clone H1) and varying amounts of antigen.

13) ELISA Optimization Assay: TCEP

An optimization ELISA was performed where the antigen solution was subject to the treatment with varying amounts of TCEP (tris(2-carboxyethyl)phosphine), which is a reducing agent that breaks disulfide bond, to determine the effect of such reduction/denaturization on the ability for the Mouse anti-BlaC mAbs and partner reagents to detect BlaC. Between 20 mM and 40 mM TCEP, at varying ng/mL, were tested. The ELISAs used 0.15 µg/mL and 0.075 µg/mL of Mouse anti-BlaC mAb (from clones G1, H1, and 31A, as described above in part VI) as the coating ("C" i.e., capture antibody) and 2.5 µg/mL purified rabbit anti-BlaC polyclonal antibody as the detection antibody ("D"). The bound detection antibody was monitored using HRP-conjugated Ab at a titer of 1:12,000 (rabbit). PBS and recombinant BlaC, generated as described above, were used as antigen.

The results of the ELISA optimization assay are set forth in Table 18.

TABLE 18

ELISA assessing titers of TCEP on the ability of Mouse anti-BlaC mAb from clones G1, H1, and 31A as the capture antibody (C), paired with 2.5 µg/mL purified rabbit anti-BlaC polyclonal antibody as the detection antibody (D), to detect BlaC antigen.

|  | C: G1 0.15 µg/mL | C: H1 0.15 µg/mL | C: 31A 0.15 µg/mL | C: G1 .075 µg/mL | C: H1 .075 µg/mL | C: 31A .075 µg/mL |
|---|---|---|---|---|---|---|
| 20 mM TCEP | 0.048 | 0.048 | 0.052 | 0.054 | 0.059 | 0.054 |
| 20 mM TCEP 5 ng/mL | 0.088 | 0.089 | 0.065 | 0.074 | 0.077 | 0.082 |
| 20 mM TCEP 10 ng/mL | 0.082 | 0.109 | 0.083 | 0.106 | 0.091 | 0.093 |
| 20 mM TCEP 20 ng/mL | 0.102 | 0.116 | 0.133 | 0.124 | 0.123 | 0.121 |
| 30 mM TCEP | 0.093 | 0.067 | 0.049 | 0.07 | 0.057 | 0.074 |
| 30 mM TCEP 5 ng/mL | 0.06 | 0.065 | 0.084 | 0.075 | 0.096 | 0.067 |
| 30 mM TCEP 10 ng/mL | 0.068 | 0.09 | 0.087 | 0.094 | 0.083 | 0.094 |
| 30 mM TCEP 20 ng/mL | 0.084 | 0.083 | 0.094 | 0.12 | 0.1 | 0.133 |
| 40 mM TCEP | 0.044 | 0.068 | 0.049 | 0.062 | 0.058 | 0.079 |
| 40 mM TCEP 5 ng/mL | 0.056 | 0.06 | 0.058 | 0.071 | 0.07 | 0.062 |
| 40 mM TCEP 10 ng/mL | 0.063 | 0.07 | 0.063 | 0.076 | 0.065 | 0.073 |
| 40 mM TCEP 20 ng/mL | 0.214 | 0.093 | 0.072 | 0.083 | 0.075 | 0.122 |

Table 18 illustrates the effect of varying amounts of TCEP on the ability of the Mouse anti-BlaC mAbs to pair with purified rabbit anti-BlaC polyclonal antibody to detect BlaC.

14) ELISA Optimization Assay: DTT

An optimization ELISA was performed where the antigen solution was subject to the treatment with varying amounts of DTT (dithiothreitol), which is a strong reducing agent that breaks disulfide bond, to determine the effect of such reduction/denaturization on the ability for the Mouse anti-BlaC mAbs and partner reagents to detect BlaC. Between 0.05% and 0.2% DTT, at varying ng/mL, were tested. The ELISAs used 0.15 µg/mL and 0.075 µg/mL of Mouse anti-BlaC mAb (from clones G1, H1, and 31A, as described above in part VI) as the coating ("C" i.e., capture antibody) and 2.5 µg/mL purified rabbit anti-BlaC polyclonal antibody as the detection antibody ("D"). The bound detection antibody was monitored using HRP-conjugated Ab at a titer of 1:12,000 (rabbit). PBS and recombinant BlaC, generated as described above, were used as antigen.

The results of the ELISA optimization assay are set forth in Table 19.

TABLE 19

ELISA assessing titers of DTT on the ability of Mouse anti-BlaC mAb from clones G1, H1, and 31A as the capture antibody (C), paired with 2.5 µg/mL purified rabbit anti-BlaC polyclonal antibody as the detection antibody (D), to detect BlaC antigen.

| | C: G1 0.15 µg/mL | C: H1 0.15 µg/mL | C: 31A 0.15 µg/mL | C: G1 .075 µg/mL | C: H1 .075 µg/mL | C: 31A .075 µg/mL |
|---|---|---|---|---|---|---|
| 0.05% DTT | 0.501 | 0.086 | 0.06 | 0.072 | 0.058 | 0.063 |
| 0.05% DTT 5 ng/mL | 0.066 | 0.076 | 0.168 | 0.074 | 0.076 | 0.064 |
| 0.05% DTT 10 ng/mL | 0.062 | 0.081 | 0.072 | 0.098 | 0.074 | 0.065 |
| 0.05% DTT 20 ng/mL | 0.091 | 0.068 | 0.084 | 0.08 | 0.069 | 0.07 |
| 0.1% DTT | 0.052 | 0.057 | 0.064 | 0.062 | 0.061 | 0.056 |
| 0.1% DTT 5 ng/mL | 0.051 | 0.072 | 0.058 | 0.069 | 0.065 | 0.059 |
| 0.1% DTT 10 ng/mL | 0.054 | 0.072 | 0.066 | 0.065 | 0.058 | 0.058 |
| 1% DTT 20 ng/mL | 0.067 | 0.074 | 0.07 | 0.103 | 0.075 | 0.072 |
| 0.2% DTT | 0.047 | 0.059 | 0.058 | 0.064 | 0.069 | 0.057 |
| 0.2% DTT 5 ng/mL | 0.052 | 0.06 | 0.055 | 0.066 | 0.062 | 0.056 |
| 0.2% DTT 10 ng/mL | 0.054 | 0.066 | 0.076 | 0.062 | 0.727 | 0.194 |
| 0.2% DTT 20 ng/mL | 0.06 | 0.067 | 0.072 | 0.1 | 0.066 | 0.074 |

Table 19 illustrates the effect of varying amounts of DTT on the ability of the Mouse anti-BlaC mAbs to pair with purified rabbit anti-BlaC polyclonal antibody to detect BlaC.

15) ELISA Optimization Assay: Purification of BlaC by Q Column

An optimization ELISA was performed where various amounts of BlaC antigen purified by Q column, which is based on ion exchange, were used to determine the effect of such isolation on the ability for the Mouse anti-BlaC mAbs and partner reagents to detect the rBlaC. The ELISAs used 0.15 µg/mL and 0.075 µg/mL of Mouse anti-BlaC mAb (from clones G1, H1, and 31A, as described above in part VI) as the coating ("C" i.e., capture antibody) and 2.5 µg/mL purified rabbit anti-BlaC polyclonal antibody as the detection antibody ("D"). The bound detection antibody was monitored using HRP-conjugated Ab at a titer of 1:12,000 (rabbit). PBS and between 10 ng/mL and 500 ng/mL Q column-purified rBlaC were used as antigen.

The results of the ELISA optimization assay are set forth in Table 20.

TABLE 20

ELISA Q column antigen purification on the ability of Mouse anti-BlaC mAb from clones G1, H1, and 31A as the capture antibody (C), paired with 2.5 µg/mL purified rabbit anti-BlaC polyclonal antibody as the detection antibody (D), to detect BlaC antigen.

| | C: G1 0.15 µg/mL | C: H1 0.15 µg/mL | C: 31A 0.15 µg/mL | C: G1 .075 µg/mL | C: H1 .075 µg/mL | C: 31A .075 µg/mL |
|---|---|---|---|---|---|---|
| PBS | 0.127 | 0.13 | 0.138 | 0.14 | 0.137 | 0.156 |
| PBS | 0.147 | 0.129 | 0.124 | 0.143 | 0.194 | 0.161 |

TABLE 20-continued

ELISA Q column antigen purification on the ability of Mouse anti-BlaC mAb
from clones G1, H1, and 31A as the capture antibody (C), paired with 2.5 µg/mL purified
rabbit anti-BlaC polyclonal antibody as the detection antibody (D), to detect BlaC
antigen.

|  | C: G1<br>0.15 µg/mL | C: H1<br>0.15 µg/mL | C: 31A<br>0.15 µg/mL | C: G1<br>.075 µg/mL | C: H1<br>.075 µg/mL | C: 31A<br>.075 µg/mL |
|---|---|---|---|---|---|---|
| BlaC 10 ng/mL | 0.161 | 0.163 | 0.188 | 0.141 | 0.137 | 0.131 |
| BlaC 10 ng/mL | 0.168 | 0.575 | 0.16 | 0.149 | 0.146 | 0.141 |
| BlaC 20 ng/mL | 0.166 | 0.144 | 0.16 | 0.155 | 0.154 | 0.171 |
| BlaC 20 ng/mL | 0.211 | 0.148 | 0.165 | 0.146 | 0.218 | 0.166 |
| BlaC 50 ng/mL | 0.182 | 0.318 | 0.172 | 0.232 | 0.193 | 0.142 |
| BlaC 50 ng/mL | 0.529 | 0.167 | 0.18 | 0.168 | 0.171 | 0.144 |
| BlaC 100 ng/mL | 0.171 | 0.165 | 0.174 | 0.154 | 0.178 | 0.207 |
| BlaC 100 ng/mL | 0.161 | 0.18 | 0.197 | 0.169 | 0.164 | 0.149 |
| BlaC 200 ng/mL | 0.149 | 0.147 | 0.274 | 0.158 | 0.152 | 0.141 |
| BlaC 200 ng/mL | 0.148 | 0.137 | 0.15 | 0.151 | 0.173 | 0.304 |
| BlaC 500 ng/mL | 0.144 | 0.188 | 0.162 | 0.258 | 0.21 | 0.151 |
| BlaC 500 ng/mL | 0.166 | 0.199 | 0.165 | 0.176 | 0.165 | 0.15 |

Table 20 illustrates the effect Q column purification of rBlaC protein on the ability of the Mouse anti-BlaC mAbs to pair with purified rabbit anti-BlaC polyclonal antibody to detect the rBlaC.

16) ELISA Optimization Assay: Purification of BlaC by Phenyl Sepharose

An optimization ELISA was performed where various amounts of BlaC antigen purified by phenyl sepharose, which is based on hydrophobic interactions, were used to determine the effect of such isolation on the ability for the Mouse anti-BlaC mAbs and partner reagents to detect the rBlaC. The ELISAs used 0.15 μg/mL and 0.075 μg/mL of Mouse anti-BlaC mAb (from clones G1, H1, and 31A, as described above in part VI) as the coating ("C" i.e., capture antibody) and 2.5 μg/mL purified rabbit anti-BlaC polyclonal antibody as the detection antibody ("D"). The bound detection antibody was monitored using HRP-conjugated Ab at a titer of 1:12,000 (rabbit). PBS and between 10 ng/mL and 500 ng/mL phenyl sepharose-purified rBlaC were used as antigen.

The results of the ELISA optimization assay are set forth in Table 21.

TABLE 21

ELISA phenyl sepharose antigen purification on the ability of Mouse anti-BlaC mAb from clones G1, H1, and 31A as the capture antibody (C), paired with 2.5 μg/mL purified rabbit anti-BlaC polyclonal antibody as the detection antibody (D), to detect BlaC antigen.

| | C: G1 0.15 μg/mL | C: H1 0.15 μg/mL | C: 31A 0.15 μg/mL | C: G1 .075 μg/mL | C: H1 .075 μg/mL | C: 31A .075 μg/mL |
|---|---|---|---|---|---|---|
| PBS | 0.153 | 0.142 | 0.179 | 0.139 | 0.15 | 0.121 |
| PBS | 0.14 | 0.134 | 0.13 | 0.138 | 0.135 | 0.305 |
| BlaC 10 ng/mL | 0.188 | 0.164 | 0.208 | 0.176 | 0.18 | 0.168 |
| BlaC 10 ng/mL | 0.159 | 0.143 | 0.205 | 0.159 | 0.167 | 0.141 |
| BlaC 20 ng/mL | 0.156 | 0.166 | 0.144 | 0.172 | 0.134 | 0.156 |
| BlaC 20 ng/mL | 0.222 | 0.183 | 0.217 | 0.162 | 0.152 | 0.186 |
| BlaC 50 ng/mL | 0.145 | 0.139 | 0.134 | 0.212 | 0.134 | 0.149 |
| BlaC 50 ng/mL | 0.219 | 0.257 | 0.15 | 0.144 | 0.166 | 0.127 |
| BlaC 100 ng/mL | 0.164 | 0.173 | 0.176 | 0.139 | 0.194 | 0.154 |
| BlaC 100 ng/mL | 0.193 | 0.218 | 0.189 | 0.144 | 0.16 | 0.128 |
| BlaC 500 ng/mL | 0.225 | 0.346 | 0.198 | 0.188 | 0.145 | 0.157 |
| BlaC 500 ng/mL | 0.273 | 0.67 | 0.285 | 0.164 | 0.185 | 0.171 |

Table 21 illustrates the effect Q column purification of rBlaC protein on the ability of the Mouse anti-BlaC mAbs to pair with purified rabbit anti-BlaC polyclonal antibody to detect the rBlaC.

CONCLUSION

The assays disclosed in this section demonstrate that the antibody reagents generated as described above are useful for specifically detecting BlaC, whether recombinant or wild-type, in biological samples. The assays can be designed with optimized concentrations and pairing of reagents to promote high sensitivity and specificity, thus providing improved methods and devices for detecting the presence of TB-complex bacteria.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of detecting and treating the presence of tuberculosis-complex bacterial infection in a subject, the method comprising:

determining the presence or amount of anti-tuberculosis-complex β-lactamase (BlaC) antibody in a biological sample obtained from the subject, wherein the presence or amount of anti-BlaC antibody in the biological sample is indicative of the presence of tuberculosis-complex bacterial infection in the subject, and treating the subject indicated to have a tuberculosis-complex bacterial infection.

2. The method of claim 1, wherein the presence of anti-tuberculosis-complex BlaC antibody in the biological sample is determined by an assay comprising the steps:

(a) contacting the biological sample with at least one polypeptide with an amino acid sequence that has at least 90% sequence identity to any six or more contiguous amino acids of SEQ ID NO:2; and (b) detecting the formation of a complex between the antibody in the sample and the polypeptide.

3. The method of claim 1, further comprising comparing the determined amount of anti-tuberculosis-complex BlaC antibody to a reference standard, where an amount of anti-tuberculosis-complex BlaC antibody detected in the biological sample greater than the reference standard is indicative of the presence of tuberculosis-complex bacteria in the subject.

4. The method of claim 3, wherein the reference standard is an analogous biological sample from a subject that does not have tuberculosis-complex bacteria.

5. The method of claim 1, wherein the tuberculosis-complex bacteria are from one or more of the species selected from the group consisting of: *Mycobacterium tuberculosis, Mycobacterium bovis, Mycobacterium bovis-Bacillus* Calmette-Guerin (BCG), *Mycobacterium africanum, Mycobacterium microti, Mycobacterium canettii, Mycobacterium pinnipedii,* and *Mycobacterium* mungi.

6. The method of claim 1, wherein the subject is a mammal.

7. The method of claim 1, wherein the subject is human.

8. The method of claim 1, wherein the biological sample is selected from the group consisting of blood, serum, sputum, saliva, breath, feces, urine, spinal fluid, mucus or tissue sample.

9. The method of claim 2, wherein the polypeptide is attached to a substrate.

10. The method of claim 9, wherein the substrate is a particle, a filter, or a well.

11. The method of claim 9, wherein the attachment is through a linker.

12. The method of claim 2, wherein the polypeptide is detectably labeled.

13. The method of claim 3, wherein the reference standard is determined from a biological sample obtained from the subject at or prior to the commencement of treatment for a tuberculosis infection.

14. The method of claim 2, wherein the at least one polypeptide has an amino acid sequence that has at least 95% sequence identity to any six or more contiguous amino acids of SEQ ID NO:2.

15. The method of claim 2, wherein the at least one polypeptide has an amino acid sequence that has at least 95% sequence identity to any 15 or more contiguous amino acids of SEQ ID NO:2.

16. The method of claim 2, wherein the at least one polypeptide comprises amino acids corresponding to amino acids at positions 75 to 87 of SEQ ID NO:2, at amino acids at positions 142 to 144 of SEQ ID NO:2, and/or at amino acids at positions 249 to 252 of SEQ ID NO:2.

* * * * *